United States Patent
Wening et al.

(10) Patent No.: US 10,624,862 B2
(45) Date of Patent: Apr. 21, 2020

(54) TAMPER-RESISTANT DOSAGE FORM CONTAINING ETHYLENE-VINYL ACETATE POLYMER

(71) Applicant: GRÜNENTHAL GMBH, Aachen (DE)

(72) Inventors: Klaus Wening, Köln (DE); Lutz Barnscheid, Mönchengladbach (DE); Sebastian Schwier, Aachen (DE); Anja Geißler, Stolberg (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 14/327,671

(22) Filed: Jul. 10, 2014

(65) Prior Publication Data

US 2015/0017250 A1 Jan. 15, 2015

(30) Foreign Application Priority Data

Jul. 12, 2013 (EP) ..................... 13176303

(51) Int. Cl.

| | |
|---|---|
| A61K 31/135 | (2006.01) |
| A61K 31/137 | (2006.01) |
| A61K 9/14 | (2006.01) |
| A61K 9/16 | (2006.01) |
| A61K 9/20 | (2006.01) |
| B29C 51/00 | (2006.01) |
| B29K 23/00 | (2006.01) |
| B29K 105/00 | (2006.01) |
| B29C 48/05 | (2019.01) |
| B29C 48/00 | (2019.01) |

(52) U.S. Cl.
CPC .......... *A61K 31/135* (2013.01); *A61K 9/146* (2013.01); *A61K 9/1635* (2013.01); *A61K 9/2031* (2013.01); *A61K 31/137* (2013.01); *B29C 51/002* (2013.01); *B29C 48/0011* (2019.02); *B29C 48/05* (2019.02); *B29K 2023/083* (2013.01); *B29K 2105/0085* (2013.01)

(58) Field of Classification Search
None
See application file for complete search history.

(56) References Cited

U.S. PATENT DOCUMENTS

| | | | |
|---|---|---|---|
| 2,524,855 | A | 10/1950 | Schnider et al. |
| 2,806,033 | A | 9/1957 | Lewenstein et al. |
| (Continued) | | | |

FOREIGN PATENT DOCUMENTS

| | | | |
|---|---|---|---|
| AR | 046994 | A1 | 12/2004 |
| AR | 045353 | A1 | 10/2005 |
| (Continued) | | | |

OTHER PUBLICATIONS

Machine translation, WO 2005/102286 (2005).*
(Continued)

*Primary Examiner* — Bethany P Barham
*Assistant Examiner* — Barbara S Frazier
(74) *Attorney, Agent, or Firm* — Norris McLaughlin, P.A.

(57) ABSTRACT

The invention relates to a tamper-resistant, oral pharmaceutical dosage form comprising a pharmacologically active ingredient having psychotropic action and an ethylene-vinyl acetate (EVA) polymer which provides resistance against solvent extraction, resistance against grinding, and resistance against dose-dumping in aqueous ethanol.

14 Claims, 8 Drawing Sheets

(56) References Cited

U.S. PATENT DOCUMENTS

| | | |
|---|---|---|
| 2,987,445 A | 6/1961 | Levesque |
| 3,332,950 A | 7/1967 | Blumberg et al. |
| 3,370,035 A | 2/1968 | Ogura et al. |
| 3,652,589 A | 3/1972 | Flick et al. |
| 3,658,259 A | 4/1972 | Ledergerber et al. |
| 3,806,603 A | 4/1974 | Gaunt et al. |
| 3,865,108 A | 2/1975 | Hartop |
| 3,941,865 A | 3/1976 | Miller et al. |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,200,704 A | 4/1980 | Stanley et al. |
| 4,207,893 A | 6/1980 | Michaels |
| 4,262,017 A | 4/1981 | Kuipers et al. |
| 4,343,789 A | 8/1982 | Kawata et al. |
| 4,353,887 A | 10/1982 | Hess et al. |
| 4,404,183 A | 9/1983 | Kawata et al. |
| 4,427,681 A | 1/1984 | Munshi et al. |
| 4,427,778 A | 1/1984 | Zabriskie |
| 4,457,933 A | 7/1984 | Gordon et al. |
| 4,462,941 A | 7/1984 | Lee et al. |
| 4,473,640 A | 9/1984 | Combie et al. |
| 4,483,847 A | 11/1984 | Augart |
| 4,485,211 A | 11/1984 | Okamoto |
| 4,529,583 A | 7/1985 | Porter |
| 4,599,342 A | 7/1986 | La Hann |
| 4,603,143 A | 7/1986 | Schmidt |
| 4,612,008 A | 9/1986 | Wong et al. |
| 4,629,621 A | 12/1986 | Snipes |
| 4,667,013 A | 5/1987 | Reichle |
| 4,690,822 A | 9/1987 | Uemura |
| 4,711,894 A | 12/1987 | Wenzel et al. |
| 4,713,243 A | 12/1987 | Schiraldi et al. |
| 4,744,976 A | 5/1988 | Snipes et al. |
| 4,764,378 A | 8/1988 | Keitn et al. |
| 4,765,989 A | 8/1988 | Wong et al. |
| 4,774,074 A | 9/1988 | Snipes |
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,954,346 A | 9/1990 | Sparta et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinity |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,194 A | 4/1993 | Edgren et al. |
| 5,200,197 A | 4/1993 | Wright et al. |
| 5,211,892 A | 5/1993 | Gueret |
| 5,225,417 A | 7/1993 | Dappen |
| 5,227,157 A | 7/1993 | Mc Ginity et al. |
| 5,229,164 A | 7/1993 | Pins et al. |
| 5,273,758 A | 12/1993 | Royce |
| 5,326,852 A | 7/1994 | Fujikake |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludgwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Graudums et al. |
| 5,811,126 A | 9/1998 | Krishnamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,914,132 A | 6/1999 | Kelm et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A | 7/2000 | Baichwal |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,235,825 B1 | 2/2001 | Yoshida et al. |
| 6,228,863 B1 | 5/2001 | Palermo et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,251,430 B1 | 6/2001 | Zhang et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,322,811 B1 | 11/2001 | Verma et al. |
| 6,322,819 B1 | 11/2001 | Burnside et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,384,020 B1 | 5/2002 | Flanner et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,455,052 B1 | 9/2002 | Marcussen et al. |
| 6,461,644 B1 | 10/2002 | Jackson et al. |
| 6,488,939 B1 | 12/2002 | Zeidler et al. |

(56) References Cited

U.S. PATENT DOCUMENTS

| | | |
|---|---|---|
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breitenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,946,146 B2 | 9/2005 | Mulye |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |
| 7,842,307 B2 | 11/2010 | Oshlack et al. |
| 7,851,482 B2 | 12/2010 | Dung et al. |
| 7,932,258 B2 | 4/2011 | Petereit et al. |
| 7,939,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric |
| 8,101,630 B2 | 1/2012 | Kumar et al. |
| 8,114,383 B2 | 2/2012 | Bartholomaeus et al. |
| 8,114,384 B2 | 2/2012 | Arkenau et al. |
| 8,114,838 B2 | 2/2012 | Marchionni |
| 8,192,722 B2 | 6/2012 | Arkenau-Maric et al. |
| 8,202,542 B1 | 6/2012 | Mehta et al. |
| 8,309,060 B2 | 11/2012 | Bartholomeus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Maric et al. |
| 8,858,963 B1 | 10/2014 | Devarakonda et al. |
| 8,901,113 B2 | 12/2014 | Leech et al. |
| 9,044,758 B2 | 6/2015 | Niwa et al. |
| 9,192,578 B2 | 11/2015 | McGinity et al. |
| 9,463,165 B2 | 10/2016 | Shimatani et al. |
| 9,629,807 B2 | 4/2017 | Arkenau-Maric et al. |
| 9,675,610 B2 | 6/2017 | Bartholomaeus et al. |
| 9,737,490 B2 | 8/2017 | Barnscheid et al. |
| 9,750,701 B2 | 9/2017 | Jans et al. |
| 9,855,263 B2 | 1/2018 | Wening et al. |
| 9,884,022 B2 | 2/2018 | Deshmukh et al. |
| 9,925,146 B2 | 3/2018 | Barnscheid et al. |
| 10,130,591 B2 | 11/2018 | Bartholomäus et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0187192 A1 | 2/2002 | Joshi et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1 | 9/2002 | Iyer et al. |
| 2002/0176888 A1 | 11/2002 | Bartholomaeus et al. |
| 2002/0192277 A1 | 12/2002 | Oshlack et al. |
| 2003/0008409 A1 | 1/2003 | Spearman et al. |
| 2003/0017532 A1 | 1/2003 | Biswas et al. |
| 2003/0021546 A1 | 1/2003 | Sato |
| 2003/0044458 A1 | 3/2003 | Wright et al. |
| 2003/0044464 A1 | 3/2003 | Ziegler et al. |
| 2003/0059397 A1 | 3/2003 | Hughes |
| 2003/0064099 A1 | 4/2003 | Oshlack et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chen et al. |
| 2003/0077327 A1 | 4/2003 | Durig et al. |
| 2003/0091630 A1 | 5/2003 | Louie-Helm et al. |
| 2003/0092724 A1 | 5/2003 | Huaihung et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0158265 A1 | 8/2003 | Radhakrishnan et al. |
| 2003/0175326 A1 | 9/2003 | Thombre |
| 2003/0198677 A1 | 10/2003 | Pryce Lewis et al. |
| 2003/0015814 A1 | 11/2003 | Krull et al. |
| 2003/0215508 A1 | 11/2003 | Davis et al. |
| 2003/0224051 A1 | 12/2003 | Fink et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0049079 A1 | 3/2004 | Murray et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0170680 A1 | 9/2004 | Oshlack et al. |
| 2004/0185105 A1 | 9/2004 | Berner et al. |
| 2004/0213845 A1 | 10/2004 | Sugihara |
| 2004/0213848 A1 | 10/2004 | Li et al. |
| 2004/0253310 A1 | 12/2004 | Fischer et al. |
| 2005/0015730 A1 | 1/2005 | Gunturi et al. |
| 2005/0031546 A1 | 2/2005 | Bartholomaeus et al. |
| 2005/0058706 A1 | 3/2005 | Bartholomaeus et al. |
| 2005/0063214 A1 | 3/2005 | Takashima |
| 2005/0079138 A1 | 4/2005 | Chickering, III et al. |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaeus et al. |
| 2005/0181046 A1 | 8/2005 | Oshlack et al. |
| 2005/0186139 A1 | 8/2005 | Bartholomaeus et al. |
| 2005/0191244 A1 | 9/2005 | Bartholomaeus et al. |
| 2005/0191352 A1 | 9/2005 | Hayes |
| 2005/0192333 A1 | 9/2005 | Hinze et al. |
| 2005/0214223 A1 | 9/2005 | Bartholomaeus et al. |
| 2005/0220877 A1 | 10/2005 | Patel |
| 2005/0222188 A1 | 10/2005 | Chapman et al. |
| 2005/0236741 A1 | 10/2005 | Arkenau et al. |

(56) References Cited

U.S. PATENT DOCUMENTS

| | | |
|---|---|---|
| 2005/0245556 A1 | 11/2005 | Brogman et al. |
| 2005/0266084 A1 | 12/2005 | Li et al. |
| 2005/0271594 A1 | 12/2005 | Groenewoud |
| 2006/0002859 A1 | 1/2006 | Arkenau et al. |
| 2006/0002860 A1 | 1/2006 | Bartholomaus et al. |
| 2006/0004034 A1 | 1/2006 | Hinze et al. |
| 2006/0009478 A1 | 1/2006 | Friedman et al. |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomeus et al. |
| 2006/0193914 A1 | 8/2006 | Ashworth et al. |
| 2006/0194759 A1 | 8/2006 | Eidelson |
| 2006/0194826 A1 | 8/2006 | Oshlack et al. |
| 2006/0204575 A1 | 9/2006 | Feng et al. |
| 2006/0240105 A1 | 10/2006 | Devane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1 | 3/2007 | Arkenau-Maric et al. |
| 2007/0048373 A1 | 3/2007 | Chastain et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |
| 2007/0259045 A1 | 11/2007 | Mannion et al. |
| 2007/0264326 A1 | 11/2007 | Guimberteau et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0014228 A1 | 1/2008 | Darmuzey et al. |
| 2008/0020032 A1 | 1/2008 | Crowley et al. |
| 2008/0063725 A1 | 3/2008 | Guimberteau et al. |
| 2008/0069871 A1 | 3/2008 | Vaughn et al. |
| 2008/0075669 A1 | 3/2008 | Soscia et al. |
| 2008/0075768 A1 | 3/2008 | Vaughn et al. |
| 2008/0081290 A1 | 4/2008 | Wada et al. |
| 2008/0085304 A1 | 4/2008 | Baichwal et al. |
| 2008/0131503 A1 | 6/2008 | Holm et al. |
| 2008/0145429 A1 | 6/2008 | Leyenecker et al. |
| 2008/0152595 A1 | 6/2008 | Emigh et al. |
| 2008/0181932 A1 | 7/2008 | Bortz et al. |
| 2008/0207757 A1 | 8/2008 | Mickle |
| 2008/0220079 A1 | 9/2008 | Chen |
| 2008/0233178 A1* | 9/2008 | Reidenberg ........ A61K 9/7061 424/449 |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0260836 A1 | 10/2008 | Boyd |
| 2008/0280975 A1 | 11/2008 | Badul |
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317695 A1 | 12/2008 | Everaert et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | McKenna et al. |
| 2009/0087486 A1 | 4/2009 | Krumme |
| 2009/0117191 A1 | 5/2009 | Brown Miller et al. |
| 2009/0143478 A1 | 6/2009 | Richardson et al. |
| 2009/0155357 A1 | 6/2009 | Muhuri |
| 2009/0202634 A1 | 8/2009 | Jans et al. |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0258066 A1 | 10/2009 | Venkatesh et al. |
| 2009/0317355 A1 | 12/2009 | Roth et al. |
| 2009/0318395 A1 | 12/2009 | Schramm et al. |
| 2010/0015223 A1 | 1/2010 | Cailly-Dufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Anderson et al. |
| 2010/0221322 A1 | 9/2010 | Bartholomaus et al. |
| 2010/0239667 A1 | 9/2010 | Hemmingsen et al. |
| 2010/0249045 A1 | 9/2010 | Babul |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2010/0316712 A1 | 12/2010 | Nangia et al. |
| 2011/0020451 A1 | 1/2011 | Bartholomaus et al. |
| 2011/0038930 A1 | 2/2011 | Barnscheid et al. |
| 2011/0077238 A1 | 3/2011 | Leech et al. |
| 2011/0082214 A1 | 4/2011 | Faure et al. |
| 2011/0092515 A1 | 4/2011 | Qiu et al. |
| 2011/0097404 A1 | 4/2011 | Oshlack et al. |
| 2011/0129535 A1 | 6/2011 | Mantelle |
| 2011/0135731 A1 | 6/2011 | Kao et al. |
| 2011/0159100 A1 | 6/2011 | Anderson et al. |
| 2011/0187017 A1 | 8/2011 | Haupts |
| 2011/0223244 A1 | 9/2011 | Liversidge et al. |
| 2011/0245783 A1* | 10/2011 | Stinchcomb ........ A61K 9/7092 604/290 |
| 2011/0262496 A1 | 10/2011 | Desai |
| 2011/0020454 A1 | 11/2011 | Lamarca Casado |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnsched et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0277319 A1 | 11/2012 | Steigerwald et al. |
| 2012/0321716 A1 | 12/2012 | Vachon et al. |
| 2013/0017262 A1 | 1/2013 | Mullen et al. |
| 2013/0022654 A1 | 1/2013 | Deshmukh et al. |
| 2013/0028970 A1 | 1/2013 | Schwier et al. |
| 2013/0028972 A1 | 1/2013 | Schwier et al. |
| 2013/0059010 A1 | 3/2013 | Henry et al. |
| 2013/0090349 A1 | 4/2013 | Geibler et al. |
| 2013/0129825 A1 | 5/2013 | Billoet et al. |
| 2013/0129826 A1 | 5/2013 | Geibler et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomäus et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |

(56) References Cited

U.S. PATENT DOCUMENTS

| | | |
|---|---|---|
| 2014/0010874 A1 | 1/2014 | Sackler |
| 2014/0034885 A1 | 2/2014 | Leech |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau Maric et al. |
| 2014/0112989 A1 | 4/2014 | Bartholomäus et al. |
| 2014/0170079 A1 | 6/2014 | Arkenau Maric et al. |
| 2014/0186440 A1 | 7/2014 | Han et al. |
| 2014/0271848 A1 | 9/2014 | Guido et al. |
| 2014/0275143 A1 | 9/2014 | Devarakonda et al. |
| 2014/0356426 A1 | 12/2014 | Barnscheid et al. |
| 2014/0356428 A1 | 12/2014 | Barnscheid et al. |
| 2014/0378498 A1 | 12/2014 | Devarakonda et al. |
| 2015/0017250 A1 | 1/2015 | Wenig et al. |
| 2015/0030677 A1 | 1/2015 | Adjei et al. |
| 2015/0064250 A1 | 3/2015 | Ghebre-Sellassie et al. |
| 2015/0079150 A1 | 3/2015 | Fischer et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0190348 A1 | 7/2015 | Haksar et al. |
| 2015/0313850 A1 | 11/2015 | Krishnamurthi et al. |
| 2015/0374630 A1 | 12/2015 | Arkenau Maric et al. |
| 2016/0089439 A1 | 3/2016 | Rajagopalan |
| 2016/0175256 A1 | 6/2016 | Bartholomaeus et al. |
| 2016/0184297 A1 | 6/2016 | Arkenau-Maric et al. |
| 2016/0256456 A1 | 9/2016 | Caruso et al. |
| 2016/0263037 A1 | 9/2016 | Arkenau Maric et al. |
| 2016/0346274 A1 | 12/2016 | Vaka et al. |
| 2016/0361308 A1 | 12/2016 | Bartholomaeus et al. |
| 2016/0367549 A1 | 12/2016 | Bartholomaeus et al. |
| 2017/0027886 A1 | 2/2017 | Bartholomaeus et al. |
| 2017/0112766 A1 | 4/2017 | Wenig et al. |

FOREIGN PATENT DOCUMENTS

| | | |
|---|---|---|
| AR | 049562 A1 | 8/2006 |
| AR | 049839 A1 | 9/2006 |
| AR | 053304 A1 | 5/2007 |
| AR | 054222 A1 | 6/2007 |
| AR | 054328 A1 | 6/2007 |
| AU | 769807 B2 | 3/2001 |
| AU | 2003237944 A1 | 12/2003 |
| AU | 2003274071 A1 | 5/2004 |
| AU | 2003279317 A1 | 5/2004 |
| AU | 2003278133 A1 | 6/2004 |
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006210145 A1 | 8/2006 |
| AU | 2006210145 B2 | 8/2006 |
| AU | 2009207796 A1 | 7/2009 |
| AU | 2009243681 A1 | 11/2009 |
| AU | 2009299810 B2 | 4/2010 |
| AU | 2006311116 B2 | 1/2013 |
| BR | PI0413318 A | 10/2006 |
| BR | PI0413361 A | 10/2006 |
| BR | PI0513300 A | 5/2008 |
| BR | PI0606145 A2 | 2/2009 |
| CA | 0722109 A | 11/1965 |
| CA | 2577233 A1 | 10/1997 |
| CA | 2650637 A1 | 10/1997 |
| CA | 2229621 A1 | 3/1998 |
| CA | 2317747 A1 | 7/1999 |
| CA | 2343234 A1 | 3/2000 |
| CA | 2352874 A1 | 6/2000 |
| CA | 2414349 | 1/2002 |
| CA | 2456322 A1 | 2/2003 |
| CA | 2502965 A1 | 5/2004 |
| CA | 2503155 | 5/2004 |
| CA | 2534925 A1 | 2/2005 |
| CA | 2534932 A1 | 2/2005 |
| CA | 2489855 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 A5 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CL | 437.-2013 | 3/2012 |
| CN | 87102755 A | 10/1987 |
| CN | 1135175 A | 11/1996 |
| CN | 1473562 A | 2/2004 |
| CN | 1980643 A | 4/2005 |
| CN | 101010071 A | 6/2005 |
| CN | 1671475 A | 9/2005 |
| CN | 101022787 A | 1/2006 |
| CN | 1863513 A | 11/2006 |
| CN | 1863514 A | 11/2006 |
| CN | 1917862 A | 2/2007 |
| CN | 1942174 A | 4/2007 |
| CN | 101011395 A | 8/2007 |
| CN | 101027044 A | 8/2007 |
| CN | 101057849 A | 10/2007 |
| CN | 101484135 A | 11/2007 |
| CN | 101091721 A | 12/2007 |
| CN | 101111232 A | 1/2008 |
| CN | 101175482 A | 2/2008 |
| CN | 101370485 A | 2/2009 |
| CN | 101394839 A | 3/2009 |
| CN | 101578096 A | 11/2009 |
| CN | 101652128 A | 2/2010 |
| CN | 102413835 A | 4/2012 |
| CN | 102821757 A | 12/2012 |
| DE | 2530563 A1 | 1/1977 |
| DE | 4229085 A1 | 3/1994 |
| DE | 4309528 A1 | 9/1994 |
| DE | 4446470 A1 | 6/1996 |
| DE | 69400215 T2 | 10/1996 |
| DE | 19522899 C1 | 12/1996 |
| DE | 2808505 A1 | 1/1997 |
| DE | 19753534 A1 | 6/1999 |
| DE | 19800689 C1 | 7/1999 |
| DE | 19800698 A1 | 7/1999 |
| DE | 19822979 A1 | 12/1999 |
| DE | 69229881 T2 | 12/1999 |
| DE | 19855440 A1 | 6/2000 |
| DE | 19856147 A1 | 6/2000 |
| DE | 19940740 A1 | 3/2001 |
| DE | 19960494 A1 | 6/2001 |
| DE | 10036400 A1 | 6/2002 |
| DE | 69429710 T2 | 8/2002 |
| DE | 10250083 A1 | 12/2003 |
| DE | 10250084 A1 | 5/2004 |
| DE | 10250087 A1 | 5/2004 |
| DE | 10250088 A1 | 5/2004 |
| DE | 10336400 A1 | 3/2005 |
| DE | 10361596 A1 | 9/2005 |
| DE | 102004019916 A1 | 11/2005 |
| DE | 102004020220 A1 | 11/2005 |
| DE | 102004032049 A1 | 1/2006 |
| DE | 102004032051 A1 | 1/2006 |
| DE | 102005005446 A1 | 8/2006 |
| DE | 102005005449 A1 | 8/2006 |
| DE | 102004032103 A1 | 9/2006 |
| DE | 102007011485 A1 | 9/2008 |

(56) References Cited

FOREIGN PATENT DOCUMENTS

| | | |
|---|---|---|
| DK | 1658055 T3 | 7/2007 |
| DK | 1658054 T3 | 10/2007 |
| DK | 1515702 T3 | 1/2009 |
| EC | SP066345 A | 8/2006 |
| EP | 0008131 A1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 |
| EP | 0226061 A2 | 6/1987 |
| EP | 0228417 A1 | 7/1987 |
| EP | 0229652 A2 | 7/1987 |
| EP | 0232877 A2 | 8/1987 |
| EP | 0239973 A2 | 10/1987 |
| EP | 0240906 A2 | 10/1987 |
| EP | 0261616 A2 | 3/1988 |
| EP | 0261616 A3 | 3/1988 |
| EP | 0270954 A1 | 6/1988 |
| EP | 0277289 A1 | 8/1988 |
| EP | 0293066 A2 | 11/1988 |
| EP | 0328775 A1 | 8/1989 |
| EP | 0358105 A1 | 3/1990 |
| EP | 0228417 B1 | 9/1990 |
| EP | 0229652 B1 | 10/1991 |
| EP | 0477135 A1 | 3/1992 |
| EP | 0277289 B1 | 4/1992 |
| EP | 0293066 B1 | 4/1993 |
| EP | 0270954 B1 | 5/1993 |
| EP | 0544144 A1 | 6/1993 |
| EP | 0583726 A2 | 2/1994 |
| EP | 0598606 A1 | 5/1994 |
| EP | 0636370 A1 | 2/1995 |
| EP | 0641195 A1 | 3/1995 |
| EP | 0647448 A1 | 4/1995 |
| EP | 0654263 A1 | 5/1995 |
| EP | 0661045 A1 | 7/1995 |
| EP | 0675710 A1 | 10/1995 |
| EP | 0682945 A2 | 11/1995 |
| EP | 0693475 A1 | 1/1996 |
| EP | 0820693 A1 | 1/1996 |
| EP | 0696598 A1 | 2/1996 |
| EP | 0216453 B1 | 3/1996 |
| EP | 0583726 B1 | 11/1996 |
| EP | 0756480 A1 | 2/1997 |
| EP | 0760654 A1 | 3/1997 |
| EP | 0780369 A1 | 6/1997 |
| EP | 0785775 A1 | 7/1997 |
| EP | 0761211 A1 | 12/1997 |
| EP | 0809488 A1 | 12/1997 |
| EP | 0820698 A1 | 1/1998 |
| EP | 0820753 A2 | 1/1998 |
| EP | 0857062 A2 | 8/1998 |
| EP | 0864324 A1 | 9/1998 |
| EP | 0864326 A2 | 9/1998 |
| EP | 0598606 B1 | 6/1999 |
| EP | 0675710 B1 | 8/1999 |
| EP | 0980894 A1 | 2/2000 |
| EP | 0988106 A1 | 3/2000 |
| EP | 1014941 A1 | 7/2000 |
| EP | 1070504 A1 | 1/2001 |
| EP | 1127871 A1 | 8/2001 |
| EP | 1138321 A2 | 10/2001 |
| EP | 1152026 A1 | 11/2001 |
| EP | 1138321 A3 | 1/2002 |
| EP | 1166776 A2 | 1/2002 |
| EP | 1201233 A1 | 5/2002 |
| EP | 0661045 B1 | 7/2002 |
| EP | 1250045 A2 | 10/2002 |
| EP | 1251120 A1 | 10/2002 |
| EP | 1293127 A2 | 3/2003 |
| EP | 1293195 A1 | 3/2003 |
| EP | 1293196 A2 | 3/2003 |
| EP | 1127871 B1 | 10/2003 |
| EP | 1201233 B1 | 12/2004 |
| EP | 1251120 B1 | 12/2004 |
| EP | 1492506 B1 | 1/2005 |
| EP | 1166776 B1 | 2/2005 |
| EP | 1502592 A1 | 2/2005 |
| EP | 1658054 A1 | 2/2005 |
| EP | 1658055 A1 | 2/2005 |
| EP | 1515702 B1 | 3/2005 |
| EP | 1527775 A1 | 4/2005 |
| EP | 1558221 A1 | 8/2005 |
| EP | 1558257 A1 | 8/2005 |
| EP | 1560585 B1 | 8/2005 |
| EP | 1611880 A2 | 1/2006 |
| EP | 1658054 B1 | 5/2006 |
| EP | 1138321 B1 | 1/2007 |
| EP | 1740161 A2 | 1/2007 |
| EP | 1658055 B1 | 3/2007 |
| EP | 1765303 A1 | 3/2007 |
| EP | 1786403 A1 | 5/2007 |
| EP | 1558221 B1 | 6/2007 |
| EP | 1813276 A1 | 8/2007 |
| EP | 1842533 A2 | 10/2007 |
| EP | 1845955 A1 | 10/2007 |
| EP | 1845956 A1 | 10/2007 |
| EP | 1859789 A1 | 11/2007 |
| EP | 1980245 A1 | 10/2008 |
| EP | 1897545 A1 | 12/2008 |
| EP | 2131830 A2 | 12/2009 |
| EP | 2246063 A1 | 11/2010 |
| EP | 2249811 A1 | 11/2010 |
| EP | 2273983 A1 | 1/2011 |
| EP | 2402004 A2 | 1/2012 |
| ES | 2336571 T3 | 12/2004 |
| ES | 2260042 T3 | 11/2006 |
| ES | 2285497 T3 | 11/2007 |
| ES | 2288621 T3 | 1/2008 |
| ES | 2289542 T3 | 2/2008 |
| ES | 2315505 T3 | 4/2009 |
| GA | 2082573 C | 5/1993 |
| GB | 1147210 A | 4/1969 |
| GB | 1567727 A | 5/1980 |
| GB | 2047095 A | 11/1980 |
| GB | 2057878 A | 4/1981 |
| GB | 2238478 A | 6/1991 |
| HR | 20070456 T3 | 6/2007 |
| HR | 20070272 T3 | 11/2007 |
| JP | S36-022895 | 11/1961 |
| JP | S55162714 A | 12/1980 |
| JP | S5659708 A | 5/1981 |
| JP | S56169622 A | 12/1981 |
| JP | S62240061 A | 10/1987 |
| JP | H0249719 A | 2/1990 |
| JP | 03-501737 A | 4/1991 |
| JP | H0517566 A | 1/1993 |
| JP | H06507645 A | 9/1994 |
| JP | 08053331 A | 2/1996 |
| JP | 8-505076 A | 6/1996 |
| JP | H09508410 A | 8/1997 |
| JP | H1057450 A | 3/1998 |
| JP | H10251149 A | 9/1998 |
| JP | 2000513333 A | 10/2000 |
| JP | 2002524150 A | 8/2002 |
| JP | 2002-275175 A | 9/2002 |
| JP | 2003113119 A | 4/2003 |
| JP | 2003125706 A | 5/2003 |
| JP | 2003526598 A | 9/2003 |
| JP | 2004143071 A | 5/2004 |
| JP | 2004530676 A | 10/2004 |
| JP | 2005506965 A | 3/2005 |
| JP | 2005515152 A | 5/2005 |
| JP | 2005534664 A | 11/2005 |
| JP | 2006506374 A | 2/2006 |
| JP | 2007501201 A | 1/2007 |
| JP | 2007501202 A | 1/2007 |
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 2009523833 A | 6/2009 |
| JP | 2009524626 A | 7/2009 |

(56) References Cited

FOREIGN PATENT DOCUMENTS

| | | | |
|---|---|---|---|
| JP | 2009531453 A | 9/2009 |
| JP | 2009536927 A | 10/2009 |
| JP | 2009537456 A | 10/2009 |
| JP | 2010505949 A | 2/2010 |
| JP | 2010527285 A | 8/2010 |
| JP | 2010534204 A | 11/2010 |
| JP | 2011504455 A | 2/2011 |
| JP | 2011506493 A | 3/2011 |
| JP | 2011510034 A | 3/2011 |
| JP | WO 2011/059074 A1 | 5/2011 |
| JP | 2012515735 A | 7/2012 |
| JP | 2012528845 A | 11/2012 |
| JP | 2013523804 A | 6/2013 |
| JP | 2013155124 A | 8/2013 |
| JP | 2013536810 A | 9/2013 |
| JP | 2014505736 A | 3/2014 |
| JP | 2014528437 A | 10/2014 |
| JP | 6085307 B2 | 2/2017 |
| JP | 2013523780 A | 6/2017 |
| KR | 1020060069832 A | 6/2006 |
| KR | 20070039041 A | 4/2007 |
| KR | 20070111510 A | 11/2007 |
| KR | 20090085312 A | 8/2009 |
| KR | 20100111303 A | 10/2010 |
| KR | 20110016921 A | 2/2011 |
| MX | 2007000008 A | 3/2007 |
| MX | 2007000009 A | 3/2007 |
| MX | 2007009393 A | 8/2007 |
| MX | 2010008138 A | 8/2010 |
| MX | 2010012039 A | 11/2010 |
| NO | 20061054 A | 3/2006 |
| NO | 20070578 A | 1/2007 |
| NO | 20074412 A | 11/2007 |
| NZ | 528302 A | 2/2007 |
| PT | 1699440 E | 12/2004 |
| PT | 1658054 E | 5/2006 |
| PT | 1658055 E | 7/2007 |
| PT | 1515702 E | 12/2008 |
| RU | 2131244 C1 | 6/1999 |
| RU | 2198197 C2 | 2/2003 |
| RU | 2220715 C2 | 1/2004 |
| RU | 2328275 C2 | 5/2004 |
| RU | 2396944 C2 | 7/2004 |
| RU | 2326654 C2 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| RU | 2567723 C2 | 11/2015 |
| SI | 1515702 T1 | 4/2009 |
| SI | 1699440 T1 | 11/2009 |
| SK | 10612003 A3 | 1/2004 |
| SU | 1759445 A1 | 9/1992 |
| TW | I254634 B | 5/2006 |
| WO | WO 1980/000841 A1 | 5/1980 |
| WO | WO 1989/005624 A1 | 6/1989 |
| WO | WO 1990/003776 A1 | 4/1990 |
| WO | WO 1993/006723 A1 | 4/1993 |
| WO | WO 93/10765 A1 | 6/1993 |
| WO | WO 1993/010758 A1 | 6/1993 |
| WO | WO 1993/011749 A1 | 6/1993 |
| WO | WO 1993/023017 A1 | 11/1993 |
| WO | WO 1994/006414 A1 | 3/1994 |
| WO | WO 1994/008567 A1 | 4/1994 |
| WO | WO 1995/017174 A1 | 6/1995 |
| WO | WO 1995/020947 A1 | 8/1995 |
| WO | WO 1995/022319 A1 | 8/1995 |
| WO | WO 1995/030422 A1 | 11/1995 |
| WO | WO 1996/000066 A1 | 1/1996 |
| WO | WO 1996/003979 A1 | 2/1996 |
| WO | WO 1996/014058 A1 | 5/1996 |
| WO | WO 1997/000673 A1 | 1/1997 |
| WO | WO 1997/033566 A2 | 9/1997 |
| WO | WO 1997/049384 A1 | 12/1997 |
| WO | WO 1998/035655 A3 | 2/1998 |
| WO | WO 1998/020073 A2 | 5/1998 |
| WO | WO 1998/028598 A1 | 7/1998 |
| WO | WO 1998/035655 A2 | 8/1998 |
| WO | WO 1998/051758 A1 | 11/1998 |
| WO | WO 1999/012864 A1 | 3/1999 |
| WO | WO 1999/032120 A1 | 7/1999 |
| WO | WO 1999/044591 A1 | 9/1999 |
| WO | WO 1999/045887 A2 | 9/1999 |
| WO | WO 1999/048481 A1 | 9/1999 |
| WO | WO 00/15261 A1 | 3/2000 |
| WO | WO 2000/013647 A1 | 3/2000 |
| WO | WO 2000/033835 A1 | 6/2000 |
| WO | WO 2000/040205 A2 | 7/2000 |
| WO | WO 2001/008661 A2 | 2/2001 |
| WO | WO 2001/012230 A1 | 2/2001 |
| WO | WO 2001/015667 A1 | 3/2001 |
| WO | WO 2001/052651 A2 | 7/2001 |
| WO | WO 2001/058451 A1 | 8/2001 |
| WO | WO 2001/097783 A1 | 12/2001 |
| WO | WO 2002/026061 A1 | 4/2002 |
| WO | WO 2002/026262 A2 | 4/2002 |
| WO | WO 2002/026928 A1 | 4/2002 |
| WO | WO 2002/035991 A2 | 5/2002 |
| WO | WO 2002/071860 A2 | 9/2002 |
| WO | WO 2002/088217 A1 | 11/2002 |
| WO | WO 2002/094254 A2 | 11/2002 |
| WO | WO 2003/006723 A1 | 1/2003 |
| WO | WO 2003/007802 A2 | 1/2003 |
| WO | WO 2003/013433 A2 | 2/2003 |
| WO | WO 2003/013476 A1 | 2/2003 |
| WO | WO 2003/013479 A1 | 2/2003 |
| WO | WO 2003/013538 A1 | 2/2003 |
| WO | WO 2003/015531 A2 | 2/2003 |
| WO | WO 2003/018015 A1 | 3/2003 |
| WO | WO 2003/024426 A1 | 3/2003 |
| WO | WO 2003/024430 A1 | 3/2003 |
| WO | WO 2003/053417 A2 | 3/2003 |
| WO | WO 2003/026624 A1 | 4/2003 |
| WO | WO 2003/026743 A2 | 4/2003 |
| WO | WO 2003/028698 A1 | 4/2003 |
| WO | WO 2003/028990 A1 | 4/2003 |
| WO | WO 2003/031546 A1 | 4/2003 |
| WO | WO 2003/035029 A1 | 5/2003 |
| WO | WO 2003/035053 A1 | 5/2003 |
| WO | WO 2003/035054 A1 | 5/2003 |
| WO | WO 2003/035177 A2 | 5/2003 |
| WO | WO 2003/039561 A1 | 5/2003 |
| WO | WO 2003/049689 A2 | 6/2003 |
| WO | WO 2003/068392 A1 | 8/2003 |
| WO | WO 2003/070191 A1 | 8/2003 |
| WO | WO 2003/092648 A1 | 11/2003 |
| WO | WO 2003/094812 A1 | 11/2003 |
| WO | WO 2003/105808 A1 | 12/2003 |
| WO | WO 2004/004693 A1 | 1/2004 |
| WO | WO 2004/043967 A1 | 2/2004 |
| WO | WO 2004/026262 A2 | 4/2004 |
| WO | WO 2004/026263 A2 | 4/2004 |
| WO | WO 2004/026280 A2 | 4/2004 |
| WO | WO 2004/037222 A2 | 5/2004 |
| WO | WO 2004/037230 A1 | 5/2004 |
| WO | WO 2004/037259 A1 | 5/2004 |
| WO | WO 2004/037260 A1 | 5/2004 |
| WO | WO 2004/043449 A1 | 5/2004 |
| WO | WO 2004/066910 A2 | 8/2004 |
| WO | WO 2004/078212 A1 | 9/2004 |
| WO | WO 2004/084869 A1 | 10/2004 |
| WO | WO 2004/093801 A2 | 11/2004 |
| WO | WO 2004/093819 A2 | 11/2004 |
| WO | WO 2004/098567 A2 | 11/2004 |
| WO | WO 2004/100894 A2 | 11/2004 |
| WO | WO 2005/002553 A1 | 1/2005 |
| WO | WO 2005/016313 A1 | 2/2005 |
| WO | WO 2005/016314 A1 | 2/2005 |
| WO | WO 2005/032524 A2 | 4/2005 |
| WO | WO 2005/041968 A2 | 5/2005 |
| WO | WO 2005/053587 A1 | 6/2005 |
| WO | WO 2005/053656 A1 | 6/2005 |
| WO | WO 2005/055981 A2 | 6/2005 |

(56) References Cited

FOREIGN PATENT DOCUMENTS

| | | |
|---|---|---|
| WO | WO 2005/060942 A1 | 7/2005 |
| WO | WO 2005/063214 A1 | 7/2005 |
| WO | WO 2005/065646 A2 | 7/2005 |
| WO | WO 2005/066183 A1 | 7/2005 |
| WO | WO 2005/079760 A1 | 9/2005 |
| WO | WO 2005/102286 A1 | 11/2005 |
| WO | WO 2005/102294 A3 | 11/2005 |
| WO | WO 2005/105036 A1 | 11/2005 |
| WO | WO 2006/102294 A2 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/002884 B1 | 3/2006 |
| WO | WO 2006/024881 A2 | 3/2006 |
| WO | WO 2006/039692 A2 | 4/2006 |
| WO | WO 2006/058249 A2 | 6/2006 |
| WO | WO 2006/082097 A1 | 8/2006 |
| WO | WO 2006/082099 A1 | 8/2006 |
| WO | WO 2006/105615 A1 | 10/2006 |
| WO | WO 2006/0128471 A2 | 12/2006 |
| WO | WO 2007/005716 A2 | 1/2007 |
| WO | WO 2007/008752 A2 | 1/2007 |
| WO | WO 2007/014061 A2 | 2/2007 |
| WO | WO 2007/048233 A1 | 5/2007 |
| WO | WO 2007/053698 A2 | 5/2007 |
| WO | WO 2007/085024 A2 | 7/2007 |
| WO | WO 2007/085024 A3 | 7/2007 |
| WO | WO 2007/093642 A2 | 8/2007 |
| WO | WO 2007/103105 A2 | 9/2007 |
| WO | WO 2007/103286 A2 | 9/2007 |
| WO | WO 2007/112273 A2 | 10/2007 |
| WO | WO 2007/112285 A2 | 10/2007 |
| WO | WO 2007/112286 A2 | 10/2007 |
| WO | WO 2007/131357 A1 | 11/2007 |
| WO | WO 2007/138466 A2 | 12/2007 |
| WO | WO 2007/149438 A2 | 12/2007 |
| WO | WO 2008/023261 A1 | 2/2008 |
| WO | WO 2008/033523 A1 | 3/2008 |
| WO | WO 2008/045060 A1 | 4/2008 |
| WO | WO 2008/069941 A2 | 6/2008 |
| WO | WO 2008/086804 A1 | 7/2008 |
| WO | WO 2008/107149 A2 | 9/2008 |
| WO | WO 2008/107149 A3 | 9/2008 |
| WO | WO 2008/109462 A2 | 9/2008 |
| WO | WO 2008/132707 A1 | 11/2008 |
| WO | WO 2008/142627 A2 | 11/2008 |
| WO | WO 2008/148798 A2 | 12/2008 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | WO 2009/092601 A1 | 7/2009 |
| WO | WO 2009/110005 A2 | 9/2009 |
| WO | WO 2009/112273 A2 | 9/2009 |
| WO | WO 2009/135680 A1 | 11/2009 |
| WO | WO 2010/022193 A2 | 2/2010 |
| WO | WO 2010/037854 A2 | 4/2010 |
| WO | WO 2010/044842 A1 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/088911 A1 | 8/2010 |
| WO | WO 2010/105672 A1 | 9/2010 |
| WO | WO 2010/140007 A2 | 12/2010 |
| WO | WO 2010/140007 A9 | 12/2010 |
| WO | WO 2010/0149169 A2 | 12/2010 |
| WO | WO 2011/008298 A2 | 1/2011 |
| WO | WO 2011/009602 A1 | 1/2011 |
| WO | WO 2011/009603 A1 | 1/2011 |
| WO | WO 2011/009604 A1 | 1/2011 |
| WO | WO 2011/095314 A2 | 8/2011 |
| WO | WO 2011/095314 A3 | 8/2011 |
| WO | WO 2011/124953 A2 | 10/2011 |
| WO | WO 2011/124953 A3 | 10/2011 |
| WO | WO 2011/128630 A2 | 10/2011 |
| WO | WO 2011/141241 A1 | 11/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/085657 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/025449 A1 | 3/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/167735 A1 | 11/2013 |
| WO | WO 2014/032741 A1 | 3/2014 |
| WO | WO 2014/059512 A1 | 4/2014 |
| WO | WO 2014/140231 A1 | 9/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/048597 A1 | 4/2015 |
| WO | WO 2015/103379 A1 | 7/2015 |
| WO | WO 2015/120201 A1 | 8/2015 |
| WO | WO 2015/004245 A1 | 11/2015 |
| WO | WO 2017/178658 A1 | 10/2017 |

OTHER PUBLICATIONS 2.9 Methoden der pharmazeutischen Technologie, European Pharmacopeia, 143-144, 1997. (Full English translation attached).
Albertini, B. "New spray congealing atomizer for the microencapsulation of highly concentrated solid and liquid substances" European Journal of Pharmaceutics and Biopharmaceutics 69 (2008) 348-357.
Almeida, A. et al., Ethylene vinyl acetate as matrix for oral sustained release dosage forms produced via hot-melt extrusion, European Journal of Pharmaceutics and Biopharmaceutics 77 (2011) 297-305.
Almeida, A. et al., Sustained release from hot-melt extruded matrices based on ethylene vinyl acetate and polyethylene oxide, European Journal of Pharmaceutics and Biopharmaceutics 82 (2012) 526-533.
Andre et al,. "O-Demethylation of Opiod Derivatives With Methane Sulfonic Acid/Methoinine: Application to the Synthesis of Naloxone and Analogues" Synthetic Comm. 22(16), pp. 2313-2327, 1992.
Apicella A.et al., Biomaterials, vol. 14, No. 2, pp. 83-90, 1993.
Application of a modelling system in the formulation of extended release hydrophilic matrices, Reprinted from Pharmaceutical Technology Europe, Jul. 2006.
Application of Opadry II, complete film coating system, on metformin HCl extended release matrices containing Polyox water soluble resin, Colorcon Apr. 2009.
Arnold C., "Teen Abuse of Painkiller OxyContin on the Rise," www.npr.org, Dec. 19, 2005.
Augustine, R.L., Catalytic Hydrogenation of a, B-Unsaturated Ketones. III The Effect of Quantity and Type of Catalysts, J.Org Chem. 28(1), pp. 152-155, Abstract 1963.
Avis, Kenneth, Parenteral Preparations, Chapter 85. pp. 1518-1541In Remington's Pharmaceutical Sciences, 17th Ed, 1985.
Bailey, F.E., et al., "Some properties of poly(ethylene oxide)' in aqueous solution," Journal of Applied Polymer Science, vol. 1, Issue No. 1, pp. 56-62, 1959.

(56) References Cited

OTHER PUBLICATIONS

Bauer et al. Lehrbuch der Pharmazeutischen Technologie. Sixth Edition 1999. Stuttgart, pp. IX-XV, Table of contents. (Full English translation attached).
Bauer, Kurt H., et al., Coated Pharmaceutical Dosage Forms—Fundamentals, Manufacturing Techniques, Biopharmaceutical Aspects, Test Methods and Raw Materials, 1st edition, 1998, CRC Press, Medpharm Scientific Publishers, (Preface, Table of Content, List of Abbreviations, Explanation of Terms only).
Baum et al.,"The impact of the addition of naloxone on the use and abuse of pentazocine", Public Health Reports, Jul.- Aug. 1987, vol. 102, No. 4, p. 426-429.
Block, Lawrence. Medicated Applications. Chapter 88. In Remington's Pharmaceutical Sciences, 17th Ed, 1985.
Braun, et al. A study of Bite Force. Part 2: Relationship to Various cephalometric Measurements. Angel Orthodontist, vol. 65 (5) pp. 373-377, 1995.
Brown, The Dissolution Procedure: Development and Validation, heading "Study Design", "Time Points" US Pharmacopoeia (USP), vol. 31(5), General Chapter 1092, pp. 1-15, 2006.
Caraballo, Journal of Controlled Release, vol. 69, pp. 345-355, 2000.
Carbopol 71G, retrieved Mar. 10, 2014 from http://www.lubrizol.com/LifeScience/Products/Carbopol71G-NF.html.
Cawello, "Parameters for Compartment-free Pharmacokinetics—Standardization of Study Design, Data Analysis and Reporting" 1999, pp. XI-XIII (table of contents).
Committee for Proprietary Medicinal Products. Note for Guidance on the Investigation of Bioavailability and Bioequivalence. 2001. pp. 1-18.
Coppens et al., "Hypromellose, Ethylcellulose, and Polyethylene Oxide Use in Hot Melt Extrusion"; Pharmaceutical Technology. 62-70, Jan. 2005.
Cornish, P. "Avoid the Crush": hazards of medication administration in patients with dysphagia or a feeding tube, CMA Media Inc., CMAJ. 172(7), pp. 871-872, 2005.
Costa et al. "Modeling and comparison of dissolution profiles"; European Journal of Pharmaceutical Sciences 13 (2001) 123-33.
Crowley M.M. et al., "Stability of polyethylene oxide in matrix tablets prepared by hot-metl extrusion," Biomaterials 23, 2002, pp. 4241-4248.
Crowley MM, Drug Dev Ind Pharm. Sep. 2007; 33(9):909-26. (Abstract only).
Dachille et al., "High-pressure Phase Transformations in Laboratory Mechanical Mixers and Mortars", Nature, vol. 186, Apr. 2, 1960, pp. 34 and 71.
Dachille, F. et al., "High-Pressure Phase Transformation in Laboratory Mechanical Mixers and Mortars", 1960., Nature, vol. 186, pp. 1-2 (abstract).
Davies, et al; European Journal of Pharmaceutics and Biopharmaceutics, 67, 2007, pp. 268-276.
Dean, D.A., E.R. Evans, I.H. Hall, Pharmaceutical Packaging Technology, Taylor & Francis, 1st Edition, Nov. 30, 2000 (Publisher description dated Oct. 22, 2010).
Deighan, C.J. et al., Rhabdomyolysis and acute renal failure resulting from alcohol and drug abuse, Q.J.Med, vol. 93, 2000, pp. 29-33.
Dejong (Pharmaceutisch Weekblad Scientific Edition) 1987, p. 24-28.
Dexheimer, Terahertz Spectroscopy: Principles and Applications (Optical Science and Engineering Series), CRC, 1 edition 2007 (Table of content only).
Disanto, Anthony. Bioavailability and Bioequivalency Testing, Chapter 77. In Remington's Pharmaceutical Sciences, 17th Ed, 1985.
Dow Chemical Company, "Using Dow Excipients for Controlled Release of Drugs in Hydrophilic Matrix Systems", Sep. 2006, pp. 1-36.
Dow Excipients Chem. of Poly, Water Soluble—Resin 2004, pp. 1-2.
Dow Technical Data, POLYOX WSR Solid Dosage Formulation via Melt Extrusion, Feb. 2003, pp. 1-3.
Efentakis M et al. "Evaluation of High Molecular Weight Poly(Oxyethyiene) (Polyox) Polymer: Studies of Flow Properties and Release Rates of Furosemide and Captopril from controlled-Release hard Gelatin Capsules", Pharmaceutical Development and Technology, 5 (3), pp. 339-346, 2000.
Eggleston, The seat of the emetic action of various drugs: J. Pharmacol. Exp. Ther. 7, 225-253 (1915).
El-Egakey, Adel et al, "Hot extruded dosage forms Part I Technology and dissolution kinetics of polymeric matrices" Pharmacerutica Acta Helvetiae, vol. 46, pp. 31-53,Mar. 19, 1970.
El-Sherbiny I.M. et al "Preparation, characterization, swelling and in vitro drug release behaviour of poly[N-acryloylglycine-chitosan] interplymeric pH and thermally-resposive hydrogels". European Polymer Journal. vol. 41, pp. 2584-2591, 2005.
Encyclopedia of Pharmaceutical Technology, Third Edition, vol. 1, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 2, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 3, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 4, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 5, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 6, edited by James Swarbrick PharmaceuTech, Inc., Pinehurst, North Carolinia, USA (Table of Contents only), Oct. 25, 2006.
Encyclopedia of Pharmacological Technology, Informa Healthcare, 1st Ed., 1996, vol. 14 (Table of Content only).
Erskine, Jr., Clyde. Quality Assurance and Control. Chapter 83. pp. 1487-1491 in Remington's Pharmaceutical Sciences, 17th Ed, 1985.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Pharmacopoeia, Third Edition Supplement 2000, Council of Europe, Strasbourg, 2000, pp. 85-107.
European Pharmacopoeia, Third Edition, Council of Europe. Strasbourg, 1997, pp. 127-152.
European Search Report and Written Opinionfor EP Application No. 11006253.6-2112, dated Dec. 16, 2011.
European Search Report and Written Opinion for EP Application No. 11006254.4-2112, dated Dec. 16, 2011.
European Search Report and Written Opinion for EP Application No. 12002708.1-1219, dated Sep. 24, 2012.
European Search Report and Written Opinion for EP Application No. 11008131.2-1219, dated Feb. 24, 2012.
European Search Report and Written Opinion for EP Application No. 11009129.5-2112, dated Apr. 10, 2012,.
European Search Report and Written Opinion for EP Application No. 12001296.8-1219, dated Jun. 26, 2012.
European Search Report and Written Opinion for EP Application No. 12001301.6-1219, dated Jun. 26, 2012.
European Search Report and Written Opinion for EP Application No. 12003743.7-1219, dated Sep. 24, 2012.
European Search Report and Written Opinion for EP Application No. 13169658.5, dated Aug. 6, 2013.
European Search Report and Written Opinion for EP Application No. 13169659.3, dated Aug. 6, 2013.
European Search Report and Written Opinion for EP Application No. 13176309.9-1460, dated Oct. 9, 2013.
European Search Report and Written Opinion for EP Application No. 13197503.9-1460, dated Feb. 18, 2014.
European Search Report and Written Opinion for EP Application No. 13425151.1-1460, dated Mar. 11, 2014.
Evaluation of Verapamil HCI (240 mg) Extended Release Matrix Formulation Using USP Apparatus III in Biorelevant Dissolution Media. Jul. 2009.

(56) References Cited

OTHER PUBLICATIONS

Evonik Industries, Eudragit Application Guidelines, 10th Edition, 2008, (Table of Contents only).
Evonik Rohm GmbH product brochure: EUDRAGIT acrylic polymers for solid oral dosage forms (2009).
Fell J.T., et al, "Determinination of Tablet Strength by the Diametral-Compression Test" Journal of Pharmaceutical Sciences, vol. 59, No. 5, May 1970, pp. 688-691.
Follonier N. et al., "Evaluation of hot-melt extrusion as a new technique for the production of polymer-based pellets for sustained release capsules containing high loadings of freely soluble drugs," Drug Development and Industrial Pharmacy, 20(8), pp. 1323-1339, 1994.
Follonier, N. et al., "Various ways of modulating the release of dltiazem hydrochloride from hot-melt extruded sustained release pellets prepared using polymeric materials" Journal of Controlled Release 36, pp. 243-250, 1995.
Formulation of Polyox ER Matrices for a Highly Soluble Active. Colorcon Jul. 2009.
Foye, W., Principles of Medicinal Chemistry; Analgesics pp. 241-242, at 241 (1989).
Foye, W., Principles of Medicinal Chemistry; Structural Features and Pharmacologic Activity, pp. 63-66 at 65 (1989).
Freed et al., "pH Control of Nucleophilic/electrophilic oxidation", International Journal of Pharmaceutics, vol. 357, pp. 180-188 (2008).
Giles R. et al. Plastic Packaging Materials, Chapter 81. pp. 1473-1477 In Remington's Pharmaceutical Sciences, 17th Ed, 1985.
Goodman and Gilman, "The Pharmacological Basis of Therapeutics, Seventh Edition", MacMillan Publishing Company, Table of Contents. 1985.
Goodman and Gilman, 1985, 7th edition, chapter 22, 491-530.
Goodman and Gilman, 1985, 7th edition, chapter 23, 533-579.
Graham N.B., Poly(Ethylene Glycol) Chemistry: Biotechnical and Biomedical Applications, p. 263-291 Chapter 17, 1992.
Griffin W, "Classification of Surface-Active Agents by HLB" Journal of the Society of Cosmetic Chemists, Atlas Powder Company, 1949, pp. 311-326.
Griffith, et al. "Tablet Crushing and the Law: The Implications for Nursing" Professional Nurse 19(1), pp. 41-42, 2003.
Gryczke et al, "Development and evaluation of orally disintegrating tablets (ODTs) containing Ibuprofen granules prepared by hot melt extrusion", Colloids and surfaces., B, Biointerfaces, Elsevier, Amsteram, NL, vol. 86, No. 2, Apr. 5, 2011, pp. 275-284.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Guidance for Industry—Statistical Approaches to Establishing Bioequivalence, FDA, BP, Jan. 2001.
Handbook of Pharmaceutica Excipients, 1986, American Pharmaceutical Association, Washington, DC and London (Table of Content Only).
Hanning C.D.et al. "The Morphone Hydrogel Suppository. A New Sustained release Rectal Preparation", Brititsh Journal of Anaesthesia, 61, pp. 221-227, 1988.
Hartauer, Kerry J. "Influence of Peroxide Impurities in Povidone and Crospovidone on the Stability of Raloxife" Pharma. Dev & Tech, 5 (3) 303-310 (2000).
Henriest D. et al. In vitro and in vivo evalation of starch-based hot stage extruded double matrix systems. Journal of Controlled Release. 2001, vol. 75, pp. 391-400.
Hoepfner et al. Fiedler Encyclopedia of Excipients. Sixth Edition, 2007, Aulendorf, Germany; Table of Contents only.
Hong S. et al. Dissolution kinetics and physical characterization of three-layered tablet with poly(ethylene oxide) core matrix capped by Carbopol. Int.J. Pharmacol. 2008, vol. 356, pp. 121-129.
Iner gas—Wikipedia, Dec. 2009, pp. 1-3.
Investigation of a Directly Compressible Metformin HCI 500mg Extended Release Formulation Based on Hypromellose, Colorcon Jul. 2009.
James, A. "The legal and clinical implications of crushing tablet medication", Nurse Times 100(50), 28-33, 2004.
Janicki S. et al. "Slow-Release Microballs: Method of Preparation", Acta Pharm. Technol. 33 (3) 154-155, 1987.
Jannetto, P. et al, "Oxycodone: Recognition and Pharmacogenomics," Toxicology News, Mar. 2003, 1-7.
Kalant H. et al., Death im Amphetamine Users: Caues and Rates, CMA Journal, vol. 112 (Feb. 8, 1975): 299-304.
Katz N. et al. "Challenges in the development of prescription opioid abuse-deterrent formulations", Clin. J. Pain, 23(8): 648-660 (Oct. 2007).
Kim C.-J. "Drug Release from Comperssed Hydrophilic Polyox-WSR Tablets" J Pharm. Sciences 1995, 84(3): pp. 303-306.
Kim N. et al. "Preparation and Evaluation of Eudragit Gels. V. Rectal Gel preparations for Sustained Release and Avoidance of First-Pass Metabolism of Lidocaine", Chem. Pharm Bull. 1992, 40(10), 2800-2804.
King et al. Oral Solid Dosage Forms. Chapter 90. pp. 163-1632 In Remington's Pharmaceutical Sciences, 17th Ed, 1985.
King, R, "Tablets, Capsules, and Pills" Remington's Pharmaceutical Sciences, pp. 1553-1593, Ch. 89, 1980, $16^{th}$ Edition.
King, Remington's Pharmaceutical Sciences 17th ed., Chapter 78, p. 1418 (1985).
Knevel, Adelbert. Separation. Chapter 78. pp. 1432-1442 In Remington's Pharmaceutical Sciences, 17th Ed, 1985.
Kolter, K., "Compression Behaviour of Kollidon SR," APV/ APGI 2002, Florence, Apr. 11, 2002.
Kondrat, T. , "Technology dosage forms" Moscow 1991, p. 96.
Lee, Y.-S. et al., Principles of Terahertz Science and Technology (Lecture Notes in Physics), Springer; 1 edition 2008. (Table of Contents Only).
Lenindzer, A., "The molecular basis of the structure and functions of cells" Moscow 1974, p. 68.
Levina et al., "The Effect of Ultrasonic Vibration on the Compaction Characteristics of Ibuprofen" Drug Development and Industrial Pharmacy, vol. 28, No. 5, pp. 495-514, 2002.
Levina M. et al "The Effect of Ultrasonic Vibration on the Compaction Characteristics of Paracetamol", Journal of Pharmaceutical Sciences, vol. 89, No. 6, pp. 705-723, Jun. 2000.
Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
Lieberman, Herbert A., Pharmaceutical Dosage Forms, Tablets, Second Edition, Revised and Expanded, 1990. vol. 2 (Cover and Table of Content only).
Lintner, Carl. Stability of Pharmaceutical Products. Chapter 82. pp. 1478-1486 In Remington's Pharmaceutical Sciences, 17th Ed, 1985.
Liu J. et al., "Properties of Lipophilic Matrix Tables Containing Phenylpropanolamine Hydrochloride Prepared by Hot-Melt Extrusion", EJPB, 52 (2001), pp. 181-190.
Lockhart H. et al, "Packaging of Pharnaceuticals and Health Care Products"; Blackie Academic & Professional; First Edition 1996. (Table of contents only).
Longer et al. Sustained-Release Drug Delivery Systems. Chapter 92. pp. 1611-1661 In Remington's Pharmaceutical Sciences, 17th Ed, 1985.
Madorsky S.L. "Thermal degradation of Polyethylene Oxide and Polypropylene Oxide", Journal of Polymer Science, pp. 183-194 vol. 36, No. 3, Mar. 1959.
Maggi et al., "Dissolution behavior of hydrophilic matrix tablets containing two different polyethylene oxides (PEOs) for the controlled release of a water-soluble drug. Dimensionality study" Biomaterials, 2002, 23, 1113-1119.
Maggi L.et al, "High molecular weight polyethylene oxides (PEOs) as an alternative to HPMC in controlled release dosage form", 2000, International Journal of Pharmaceutics, 195 pp. 229-238.
Maggi, C.. Therapeutic Potential of Capsaicin-like Molecules. Life Sciences, vol. 51, pp. 1777-1781, 1992.
Mank R. et al., "Darstellung wirkstoffhaltiger Extrusionsformlinge auf der Basis von Thermoplasten. Teil 1: Untersuchung zur Wirkstof-

(56) References Cited

OTHER PUBLICATIONS fliberation" Pharmazie 44, H. 11, pp. 773-776, 1989. English language translation of relevant paragraph provided.
Mank R., "Darstellung wirkstoffhaltiger Extrusionsformlinge auf der Basis von Thermoplasten. Teil 2: Unersuchungen zur Optimierung der Wirkstofffreigabe" Pharmazie 45, H. 8, pp. 592-593 1990. English language translation of relevant paragraph provided.
Marques, Tablet breaking force, 2008.
Matos, Dr. Rick, Ph.D—Letter Jan. 6, 2011.
McGary, C.W.. Jr. "Degradation of Poly(ethylene Oxide)", Journal of Polymer Science vol. XLVI,1960, pp. 51-57.
McGinity et al., Hot-Melt Extrusion as a Pharmaceutical Process, American Pharmaceutical Review, vol. 4 (2), pp. 25-36, 2001.
McGinity, J.W.—Letter of Jan. 26, 2009, pp. 1-4.
McNeill M. et al. Properties controlling the diffusion and release of water-soluble solutes from poly(ethylene oxide) hydrogels. 4. Extended constant rate release from partly-coated spheres. Journal Biomat. Sci. Polymer. Ed. 1996, vol. 7, pp. 953-963.
Mesiha M.S. et al "A Screening Study of Lubricants in Wet Powder Passes Suitable for extrusio-spheronization", Drug Development and Industrial Pharmacy, 19(8), pp. 943-959, 1993.
Metformin Hydrochloride 750 mg Extended Release Tablets. Lubrizol Advanced Materials, Inc., Sep. 2010.
Metformin Hydrochloride1000 mg Extended Release Tablets, Lubrizol Advanced Materials, Inc., Nov. 20, 2009, Previous Edition Dec. 19, 2008.
Miles, R.E. et al., Terahertz Frequency Detection and Identification of Materials and Objects (NATO Science for Peace and Security Series B: Physics and Biophysics), Springer; 1 edition 2007. (Table of contents).
Miller "To crush or not to crush? What to consider before giving medications to a patent with a tube or who has trouble swallowing", Nursing, pp. 50-52, Feb. 2000.
Mises à jour cumulatives, Vidal, Jan./Oct. 2002 (full translation attached).
Mitchell, "Oral Dosage Forms That Should Not Be Crushed: 2000 Update" Hospital Pharmacy 35(5), 553-557, 2000.
Morissette et al. Adv. Drug. Del. Rev. 26 (2004), 275-300.
Moroni A. et al, "Application of Poly(Oxyethylene) Homopolymers in Sustained release Solid formulations" Drug Development and Industrial Pharmacy, 21(12) pp. 1411-1428, 1995.
Mullins, John. Ophthalmic Preparations. Chapter 87. pp. 1553-1563; In Remington's Pharmaceutical Sciences, 17th Ed, 1985.
Munjal M. et al., "Polymeric Systems for Amorphous Delta^9—Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munseil Book of Color: Glossy Collection", X-Rite, Originally published in 1966, pp. 1-7.
Nairn, J.G., Solutions, Emulsion, Suspensions and Extractives. Chapter 84. pp. 1492-1517, In Remington's Pharmaceutical Sciences, 17th Ed, 1985.
Note for Guidance on Stability Testing, EMEA, Aug. 2003, pp. 1-20.
Note for Guidance on the Investigation of Bioavailability and Bioequivalence, EMEA, London, Jul. 26, 2001 (CPMP/EWP/QWP/1401/98).
Ohnishi N. et al., Effect of the Molecular Weight of Polyethylene Glycol on the Bioavailability of Indomethacin Sustained-Release suppoositories Prepared with Solid Dispersion, Chem. Pharm, Bull, 35(8), pp. 3511-3515, 1987.
Oxicotin: Balancing Risks and Benefits, United States Senate, Hearing, Feb. 12, 2002.
Oxycodon (Oxygesic): Missbrauch, Abhaengigkeit and toedliche Folgen durch Injection zerstossener Retardtabletten, Deutsches Ärzteblatt, vol. 36, A2326-A2326, Sep. 5, 2003.
Ozeki T. et al. "Control of Medicine Release From Solid Dispersion Through Poly(ethylene oxide)-Carboxyvinylpolymer Interaction", International Journal of Pharmaceutics, 165, 1998, pp. 239-244.

Ozeki T, et al. "Controlled Release From Solid Dispersion Composed of Poly(ethylene oxide)-Carbopol Interpolymer Complex With Various Cross-Linking Degrees of Carbopol", Journal of Controlled Release. 63, 2000. pp. 287-295.
Ozeki T. et al., "Control of medicine release from solid dispersion composed of the poly(ethylene oxide)-carboxyviylpolymer interpolymer complex by varying molecular wight of poly(ethylene oxide)"Journal of Controlled Release 58, pp. 87-95, 1999.
PCT International Search Report and Written Opinion for PCT Application No. PCT/EP2014/064830 dated Aug. 6, 2014.
PCT International Search Report and Written Opinion for PCT Application No. PCT/EP2009/003290 dated Jul. 9, 2009.
PCT International Search Report and Written Opinion for PCT Application No. PCT/EP2010/004459 dated Dec. 1, 2010.
PCT International Search Report and Written Opinion for PCT Application No. PCT/EP2013/053894 dated Mar. 22, 2013.
PCT International Search Report and Written Opinion for PCT Application No. PCT/EP2013/057851 dated Jun. 12, 2013.
PCT International Search Report and Written Opinion for PCT Application No. PCT/EP2013/059728 dated Aug. 6, 2013.
PCT Second Written Opinion for PCT Application No. PCT/EP2013/053893 dated Feb. 21, 2014.
PCT Second Written Opinion for PCT Application No. PCT/EP2013/057851 dated Apr. 15, 2014.
Pentoxifylline 400 mg Extended Release Tablets, Lubrizol Advanced Materials, Inc., Mar. 3, 2011, Previous Edition Nov. 19, 2009.
Perez-Marcos, B., Usefulness of certain varieties of Carbomer in the formulation of hydrophilic furosemide matrices, International Journal of Pharmaceutics, 67 (1991) 113-121.
Pharm. Research, Official Journal of the American Association of Pharmaceutical Scientists, Oct. 1991, 8(10), S-192.
Pharm. Research, Official Journal of the American Association of Pharmaceutical Scientists, Sep. 1989, 6(9), S-98.
Phillips, G. Briggs. Sterilization. Chapter 79. pp. 1443-1454, In Remington's Pharmaceutical Sciences, 17th Ed, 1985.
Physico-mechanical Characterization of Polyox for Table Manufacture, Colorcon Jul. 2009.
Pillay V. et al. A novel approach for constant rate delivery of highly soluble bioactives from a simple monolithic system. Journal of Controlled Release. 2000, vol. 67, pp. 67-78.
Pinto, Joao F. et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).
Piringer, O.G.and A.L. Baner, Plastic Packaging: Interactions with Food and Pharmaceuticals, Wiley VCH, 2nd Completely Revised Edition, Feb. 13, 2008. (Table of Contents only).
POLYOX water soluble resins 2003. http://www.dow.com/webapps/lit/litorder.asp?filepath=polyox/pdfs/noreg/326-00002.pdf.
POLYOX water-soluble resins (DOW Mar. 2002); see http://msdssearch.dow.com/PublishedLiteratureDOWCOM/dh_0031/0901b80380031a4a.pdf?filepath=/326-00001.pdf&fromPage=GetDoc).
POLYOX WSR-303, retrieved Mar. 10, 2014 from http://www.dow.com/dowwolff/en/industrial_solutions/polymers/polyethylene.
POLYOX, Colorcon, Application Data (Apr. 2009) downloaded from http://www.colorcon.com/literature/marketing/mr/Extended%20Release/POLYOX/English/ads_PEO_Antioxidant.pdf.
Pontier, C. et al, "Use of cycles of compression to characterize the behavior of apatitic phosphate powders," Journal of the European Ceramic Society 22 (2002), 1205-1216.
Porter, S. Coating of Pharmaceutical Dosage Forms, Chapter 91. pp. 1633-1643 In Remington's Pharmaceutical Sciences, 17th Ed, 1985.
Prapaitrakul W. et al, "Release of Chlorpheniramine Maleate from Fatty Acid Ester Matrix disks Prepared by Melt-extrusion" J. Pharm. Pharmacol. 43, pp. 377-381, 1991.
Proeschel, P.A. et al., "Task-dependence of activity / bite-force Relations and its impact on estimation of chewing force from EMG"; J. Dent. Res., vol. 81, No. 7, pp. 464-468, 2002.
Purdue News, "Purdue Pharma Provides Update on Development of New Abuse-Resistant Pain Medications; FDA Cites Patient Needs as First Priority; New Drug Application Delayed," www.headaches.about.com, Jun. 18, 2002, pp. 1-6.

(56) References Cited

OTHER PUBLICATIONS

Radko S. et al., Applied ad Theoretical Electrophoresis 5, pp. 79-88, 1995.
Ravin, L. Preformulation, Chapter 76, pp. 1409-1423, In Remington's Pharmaceutical Sciences, 17th Ed, 1985.
Remington, The Science and Practice of Pharmacy, 19th ed., vol. II, p. 1457 (1995) (providing a table of DFA-approved commercially marketed salts).
Repka M. et al., Bioadhesive Properties of Hydroxypropylcellulose Topical Films Produced by Hot-Melt Extrusion, Journal of Controlled Release, 70 (2001), pp. 341-351.
Repka MA, Drug Dev Ind Pharm, Oct. 2007; 33(10):1043. (Abstract).
Riippi M. et al., The effect of compression force on surface structure, crushing strength, friability and disintegration time of erythromycin acistrate tablets, Eur J Pharm Biopharm, vol. 46, 1998, pp. 339-345.
Rippie E.G. et al, "Regulation of Dissolution Rate by Pellet Geometry" Journal of Pharmaceutical Sciences, Vo. 58, No. 4, pp. 428-431, Apr. 1969.
Rippie, E. Powders. Chapter 89, pp. 1585-1602, In Remington's Pharmaceutical Sciences, 17th Ed, 1985.
Ritschel et al. Die Tablette: Handbuch der Entwicklung, Herstellung und Qualitatssicherung. 2nd Edition, 2002 Ch 6, pp. 515-519. (Full English translation attached).
Ritschel et al. Die Tablette: Handbuch der Entwicklung, Herstellung und Qualitatssicherung. 2nd Edition, 2002, Table of content.
Rowe C et al. Handbook of Pharmaceutical Excipients. Sixth Edition. 2009, Edition Cantor Verlag Aulendorf, pp. V-IX, Table of Contents.
Rowe C et al., Handbook of Pharmaceutical Excipients, 7th Edition, 2012, Table of Contents.
Sax et al., Hawley's Condensed Chemical Dictionary, 11th ed., 1987, p. 1233, definition of "wax".
Scheirs J., et al."Characterizing the Solid-State Thermal Oxidation of Poly (ethylene oxide) Powder", pp. 2914-219, Polymer, vol. 32, No. 11, 1991.
Schier et al. "Fatality from Administration of Labetalol and Crushed Extended-Release Nifedipine" The Annals of Pharmacotherapy vol. 37, 1420-1423, Oct. 2003.
Schroeder J., et al. Granulierung hydrophober Wirkstoffe im Planetwalzenextruder, Pharm. Ind. 2003, vol. 65, No. 4, 367-372. (Full English translation attached).
Sciarra et al. Aerosols. Chapter 93., pp. 1662-1677, In Remington's Pharmaceutical Sciences, 17th Ed, 1985.
Search result conducted on http://www.unitconversion.org/force/newtons-to-kiloponds-convresion.html, on Jul. 5, 2011 (Conversion of 18.8 kiloponds to newtons).
Shivanand P et al., "Factors Affecting Release of KCI From Melt extruded Polyethylene Disks", Pharmaceutical Research, Oct. 1991, vol. 8, No. 10 p. S-192.
Siegel. P. Tonicity, Osmoticity, Osmolality, and Osmolarity. Chapter 80. pp. 1454-1472 In Remington's Pharmaceutical Sciences, 17th Ed, 1985.
Silver, J. "Painkiller OxyContin "most commonly abused prescription drug on the streets of Western Pennsylvania, Pittsburg Post-Gazette, Apr. 8, 2001.
Spassov et al., Stereochemistry of Diastereomeric 3-Dialkylaminopropanols and O-Derivatives, J.f. prakt. Chemie, 323:5, 793-800 (1981).
Sprockel O.L et al. "Permeability of Cellulose Polymers: Water Vapour Transmission Rates"., J. Pharma. Pharmacol. 42, pp. 152-157, 1990.
Sreenivasa, B. et al, Design and Evaluation of Ethylene Vinyl Acetate Sintered Matrix Tablets, Indian Journal of Pharmaceutical Sciences, Sep.-Oct. 2003, 65(5): 496-502.
Stafford J., überzogene feste Fromen, 1991, 347-68. (English translation attached).
Strang, Abuse of buprenorphie (Temgesic) by snorting, Letter to the editor, British Med. J., 302: 969 (1991).

Stringer J.L., et al "Diffusion of small molecular weight drugs in radiation-crosslinked poly(ethylene oxide) hydrogels", Journal of Controlled Release 42, pp. 195-202, 1996.
Summers et al; "Influence of Crystal Form on Tensile Strength of Compacts of Pharmaceutical Materials" Journal of Pharmaceutical Sciences, vol. 66, No. 8, Aug. 1977, pp. 1172-1175.
Swarbrick, Encyclopedia of Pharmaceutical Technology, Informa Healthcare, 1988, 1st edition, vol. 1, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 2, table of contents.
Swarbrick, Encyclopedia of Pharmaceutical Technology, Informa Healthcare, 1988, 1st edition, vol. 20, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Tablet, www.docstoc.com (2011).
Third Party Observations filed with EPO for Patent EP65805581, Feb. 2, 2009, pp. 1-8.
Thoma V.K. et al. "Bestimmung der In-vitro-Freigabe von schwach basischen Wirkstoffen aus Ratardarzneiformen", pp. 299-301, Pharm. Ind. 51, Nr. 3, 1989.
Tikhonov, A. et al, Biopharmacy, The Manual for Students of Pharmaceutical Universities and Departments, 2003, pp. 40-41, Kharkov, Ukraine (Full English translation attached).
Tipler, et al, Physics for Scientists and Engineers, vol. I, 6th Edition, pp. 234-235, 2003.
Tompkins et al., "Human abuse liability assessment of oxycodone combined with ultra-low-dose natrexone." Psychopharma., 210:471-480 (2010).
Tramadol Hydrochloride 100 mg Extended Release Tablets, Lubrizol Advanced Materials, Inc., Sep. 2010.
Tranquilan-Aranilla et al., "Kappa-carrageenan-polyethylene oxide hydrogel blends prepared by gamma irradiation," Radiation Physics and Chemistry vol. 55, pp. 127-131, 1999.
Turco et al. Intravenous Admixtures, Chapter 86. pp. 1542-1552, In Remington's Pharmaceutical Sciences, 17th Ed, 1985.
US Pharmacopoeia, Chapter 1217, Aug. 12, 2008.
Varma et al, Factors Affecting Mechanism and Kinetics of Drug Release from Matrix-Based Oral Controlled Drug Delivery Systems, Am. J. Drug Deliv. 2004: 2 (1): 43-57.
Vippagunta et al. Adv. Del. Rev. (2001), 3-26.

(56) References Cited

OTHER PUBLICATIONS

Wade and Weller, "Handbook of Pharmaceutical Excipients: 2nd Edition", The American Pharmaceutical Association and the Pharmaceutical Press, Washington and London, Table of Contents pp. v-vi, 1994.
Wagner, Pharmazeutisch Biologie—Drogen und ihre Inhaltsstoffe—Scharfstoffdrogen,2nd., revised edition, Gustav Fischer Verlag, Stuttgart-N.Y., 1982, pp. 82-92 (Full English Translation attached).
Wagner, Pharmazeutisch Biologie—Drogen und ihre Inhaltsstoffe—Scharfstoffdrogen,2nd., revised edition, Gustav Fischer Verlag, Stuttgart-N.Y., 1982,Table of Content.
Waltimo, et al, "A novel bite force recorder and maximal isometric bite force values for healthy young adults", Scandinavian Journal of Dental Research 1993; 101: 171-175.
Waltimo, et al, "Maximal bite force and its association with signs and symptoms of craniomandibular disorders in young Finnish non-patients", Acta Odontol Scand 53 (1995): 254-258.
Waterman et al., "Stabilization of Pharmaceuticals to Oxidative Degradation", Pharmaceutical Development and Technology, vol. 7(1), pp. 1-32, (2002).
Waters et al., "Intravenous Quetiapine-Cocaine Use ("Q-Ball")", Letter to the Editor, Am. J. Psychiatry, 164(1): pp. 173-174 (2007),.
Weiss, U., "Derivatives of Morphine. I 14-Dihydroxydihydromorphinone," J. Am. Chem. Soc. 77, pp. 5891-5892, Nov. 20, 1955.
Wikipedia-Dextromethorphan Aug. 12, 2013 (and attached related English-language entry dated Dec. 11, 2013).
Woodburn, K.R. et al., Vascular complications of injecting drug misuse, Br. J. of Surgery, vol. 83, 1996, pp. 1329-1334.
Wu N, et al. Mathematical modeling and in vitro study of controlled drug release via a highly swellable and dissoluble polymer matrix: polyethylene oxide with high molecular weights, J Control Release. Feb. 16, 2005;102(3):569-581.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.
Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.
Yarbrough et al, Letters to Nature "Extraordinary effects of mortar-and-pestle grinding on microstructure of sintered alumina gel", Nature 322, pp. 347-349 (Abstract only) (Jul. 24, 1986).
Yeh et al., Stability of Morphine in Aqueous Solution III: Kinetics of Morphine Degradation in Aqueous Solution, Wiley Subscription Services, Inc., Journal of Pharmaceutical Sciences, 50(1): 35-42 (1961).
Zeeshan, F and N. Bukhari, "Development and Evaluation of a Novel Modified-Release Pellet-Based Tablet System for the Delivery of Loratadine and Pseudophedrine Hydrochloride as Model Drugs," AAPS PharmaSciTech 11(2); 910-916 (available on-line May 22, 2010).
Zhang et al., "Properties of Sustained-Release Tablets Prepared by Hot-Melt Extrusion" Pharmaceutical Development and Technology, 1999, 4(2), 241-250.
Moorman-Li, R. et al, "A Review of Abuse-Deterrent Opioids for Chronic Nonmalignant Pain." Pharmacy and Therapeutics, vol. 37 No. 7, Jul. 2012, pp. 412-421.
Eudragit NE40D web page from Evonik website; downloaded Feb. 24, 2015.
Eudragit RS PO web page from Evonik website; downloaded Feb. 24, 2015.
Glyceryl behenate monograph; European Pharmacopeia 5.0; dated Jan. 2005; downloaded Feb. 24, 2015.
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.
Bruce et al, Properties of hot-melt extuded tablet formulations for the colonic delivery of 5-aminosalicylic acid, European Journal of Pharmaceutics and Biopharmaceutics, 59 (2005) 85-97.
Bingwen et al, 2008, p. 367.
PCT International Search Report and Written Opinion for PCT Application No. PCT/EP2015/060377 dated Jul. 23, 2015.
PCT International Search Report and Written Opinion for PCT Application No. PCT/EP2015/061343 dated Jul. 21, 2015.
Bingwen et al, 2008, p. 367. (full translation attached).
Extended European Search Report and Opinion for Application No. EP 15153679.4-1455, dated Jun. 30, 2015.
West, Anthony R., Solid state chemistry and its applications, Wiley, New York, 1988, pp. 358 and 365.
Monolithic: retrieved from internet: http:/merriam-webster.com/dictionary/monolithic. Retrieved on Sep. 2, 2015.
European Search Report and Written Opinion for EP Application No. 14169801.9-1455, dated Oct. 20, 2014.
European Search Report and Written Opinion for EP Application No. 14176277.3-1460, dated Dec. 15, 2014.
Dierickx et al., "Co-extrusion as manufacturing technique for fixed-dose combination mini-matrices," European Journal of Pharmaceutics and Biopharmaceutics 81 (2012), 683-689.
Oliveira et al., "Production and characterization of laminar coextrudates at room temperature in the absence of solvents," AAPS Annual Meeting and Exposition, Oct. 14-18, 2012, Chicago, USA.
Quintavalle et al., "Preparation of sustained release co-extrudates by hot-melt extrusion and mathematical modelling of in vitro/in vivo drug release profiles," European Journal of Pharmaceutical Sciences 33 (2008), 282-293.
Rosiaux et al. "Ethanol-resistant ethylcellulose/guar gum coatings—Importance for formulation parameters" European Journal of Pharmaceutics and Biopharmaceutics, vol. 85, No. 3, (Jul. 25, 2013). pp. 1250-1258.
Salomies et al., "Determination of Oxycodone Hydrochloride in Oral Solutions by High-Performance Thin-Layer Chromatography/Densitometry," Journal of AOAC International, 83:1497-1501 (2000).
Extended European Search Report and Opinion for Application No. EP 15165067.8-1455, dated Nov. 2, 2015.
Extended European Search Report and Opinion for Application No. EP 15165065.2-1455, dated Nov. 2, 2015.
Extended European Search Report and Opinion for Application No. EP 15165069.4-1455 dated Nov. 2, 2015.
Extended European Search Report and Opinion for Application No. EP 15165064.5-1455, dated Oct. 16, 2015.
Extended European Search Report and Opinion for Application No. EP 15165070.2-1455, dated Nov. 2, 2015.
Chibuzor et al. "Formulation Development and Evaluation of Drug Release Kinetics from Colon-Targeted Ibuprofen Tablets Based on Eudragit RL 100—Chitosan Interpolyelectrolyte Complexes," Hindawi Publ. Corporation ISRN Pharmaceutics, vol. 2013, Article ID 838403.
Satish et al. "Formulation and Characterization of Matrix and Triple Layer Matrix Tablets for Controlled Delivery of Tramadol Hydrochloride," International Journal of Pharmaceutical Sciences; 5(4) (2013) 458-464.
Verhoeven, et al. "Xanthan gum to tailor drug release of sustained-release ethylcellulose mini-matrices prepared via hotmelt extrusion: in vitro and in vivo valuation," European Journal of Pharmaceutics and Biopharmaceutics, 63 (2006) 320-330.
Tennant, "Simultaneous Use of Stimulants and Opioids," 2011 [online] retrieved on Jul. 7, 2016 from: http://www.practicalpainmanagement.com/treatments/pharmacological/opioids/simultaneous-use-stimulants-opioids; 7 pages.
Cuesov, Drug Production Technology, Khar'kov, 1999, pp. 351-352.
Efentakis et al, Effects of Excipients on Swellin and Drug Release from Compressed Matrices, in Drug Development and Industrial Pharmacy 23(1):107-112, Jan. 1997, Abstract.
Linz et al. "Cebranopadol: A Novel Potent Analgesic Nociception/Orphanin FQ Peptide and Opioid Receptor Agonist," J Pharmacal. Exp. Ther. 2014; 349: 535-548; available online Apr. 8, 2014.
Borquist et al., "Simulation of the release from a multiparticulate system validated by single pellet and dose release experiements," J. Controlled Release, 97: 453-465 (2004).

(56) References Cited

OTHER PUBLICATIONS

Extended European Search Report and Opinion for Application No. EP 15184634.2-1455, dated Mar. 3, 2016.
Handbuch der Kunststoff-Extrusionstechnik 1, "Grundlagen" in Chapter 1.2 "Klassifizierung von Extrudern", pp. 3-7. 1989. (Full english translation attached).
Saleem et al. "Formulation and Evaluation of Tramadol hydrochloride Rectal Suppositories," Indian J. Pharm Sci. Sep.-Oct. 2008; 70(5), 640-644.
Sidhu et al., "Watch for nonpsychotropics causing psychiatric side effects," Current Psychiatry, vol. 7, No. 4, 2008, 61-74.
The Merck Index, 14th Ed. (2006) No. 0006360 Nalefene.
The Merck Index, 14th Ed. (2006) No. 0006362 Naloxone.
The Merck Index, 14th Ed. (2006) No. 0006363 Naltrexone.
The Merck Index, 14th Ed. (2006) No. 0006959 Oxycodone.
Verhoeven et al., "Influence of polyethylene glycol/polyethylene oxide on the release characteristics of sustained-release ethylcellulose mini-matrices produced by hot-melt extrusion: in vitro and in vivo evaluations," European Journal of Pharmaceutics and Biopharmaceutics 72 (2009) 463-470.
Vynckier et al.,"Hot-melt co-extrusion for the production of fixed-dose combination products with a controlled release ethylcellulose matrix core," International Journal of Pharmaceutics 464 (2014), 65-74.
Extended European Search Report for Application No. EP 16183922.0-1460, dated Oct. 31, 2016.
Fathima, N. et al. "Drug-excipient interaction and its importance in dosage form development," Journal of Applied Pharmaceutical Science 01 (06); 2011, pp. 66-71.
Meyer et al., "Awareness Topic: Mitigating the Risks of Ethanol Induced Dose Dumping from Oral Sustained/Controlled Release Dosage Forms," FDA ACPS Meeting, Oct. 2005, p. 1-4.
Remington, Chapter 45, pp. 996-1035.
Schilling, et al., "Novel application of hot-melt extrusion for the preparation of monolithic matrices containing enteric-coated particles." International Journal of Pharmaceutics 400 (2010) 34-31.
Starch 1500, Partially Pregelatinized Maize Starch, technical data from Colorcon, Feb. 2016, 6 pages.
Decision of the United States District Court for the Southern District of New York, in In re *Endo Pharmaceuticals Inc. and Grünenthal GmbH* v. *Amneal Pharmaceuticals, LLC et al.*, Findings of Fact and Conclusions of Law, District Judge Thomas P. Griesa, New York, New York, Jan. 14, 2015.
Decision of the United States District Court for the Southern District of New York, in In re Oxycontin Antitrust Litigation, *Purdue Pharma LP* v. *Teva Pharmaceuticals*, Findings of Fact and Conclusions of Law, District Judge Sidney H. Stein, New York, New York, Jan. 14, 2014.
U.S. Court of Appeals, Federal Circuit, *Purdue Pharma L.P.* v. *Epic Pharma, LLC*, 117 USPQ2d 1733 (Fed. Cir. 2016).
Al-Angari, A. et al. "The compaction properties of polyethylene glycols," J Pharm. Pharmacol. (1985) 37:151-153.
Al-Nasassrah et al. , "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization in Polystyrene," Macromolecules 28:2944-54 (1995).
Back, D.M.et al., "Ethylene Oxide Polymers", in Kirk-Othmer Encyclopedia of Chemical Technology. 2000, John Wiley & Sons, Inc., vol. 10, 673-696.
Bailey, F.E., et al., "High Molecular Weight Polymers of Ethylene Oxide" Solution Properties Industrial and Engineering Chemistry, 1958. 50(1): 8-11.
Balogh, E., "Tastes in and Tastes of Paprika," in Taste: Proceedings of the Oxford Symposium on Food and Cookery 28 (Tom Jaine Ed. 1988, pp. 25-40.
Baumann, T., "Pain Management," Pharmacotherapy: A Pathophysiologic Approach (J.T. DiPiro et al. eds., McGraw-Hill 4th ed. 1999), Ch. 56, 1014-1026.

Baumrucker, S.J., "OxyContin, the Media, and Law Enforcement", American Journal of Hospice & Palliative Care, 18:3 (May/Jun. 2001), 154-156.
Choi, S., et al., "Development of a Directly Compressible Poly(Ethylene Oxide) Matrix for the Sustained-Release of Dihydrocodeine Bitartrate", Drug Development and Industrial Pharmacy, vol. 29, No. 10, pp. 1045-1052, 2003.
Choi, S., et al., "Hydrophilic Matrix Formulations of Dihydrocodeine Bitartrate with Polyethylene Oxide by Direct Compression," Proceedings of the 29$^{th}$ Annual Meeting of the Controlled Release Society, in collaboration with the Korea Society for Biomaterials, Minneapolis, 1$^{st}$ Edition, 2002, 984-985.
Ciccone, P. E., "Attempted Abuse of Concerta," Letters to the Editor, J. Am. Acad. Child Adolesc. Psychiatry, 41:7 (Jul. 2002).
Controversies in ADHD: A Breakfast Symposium—Concerta.
Crowley, M. et al., Pharmaceutical Applications of Hot-Melt Extrusion: Part I. Drug Dev. & Indus. Pharmacy (2007) 33:909-926.
Crowley, M. et al., "Properties of Hot-Melt Extruded CPM Tablets Using Hydrophilic Polymers," poster presentation, (2000).
Crowley, M., "Physicochemical and Mechanical Characterization of Hot-Melt Extruded Dosage Forms." Dissertation presented to the Faculty of the Graduate School of the University of Texas at Austin. (May 2003).
Crowley, M., et al., "Evaluation of a Hot Melt Extrusion Technique using a Hydrophilic Thermal Polymer and Retardant for the Preparation of Extended Release Chlorpheniramine Maleate Tablets," in American Association of Pharmaceutical Scientists: Indianapolis, IN (2000).
CROWLEY0000001-CROWLEY0000127.
Davies, N. "Sustained Release and Enteric Coated NSAIDs: Are They Really GI Safe?"J. Pharm. & Pharmaceut. Sci., 2(1):5-14, 1999.
Declaration of Dr. James W. McGinity, dated Oct. 28, 2009; online, retrieved from: http://www.accessdata.fda.gov/dmgsatfda_docs/labeV2013/021121s032lbl.pdf.
Dimitrov, M, et al., "Study of Verapamil hydrochloride release from compressed hydrophilic Polyox-Wsr tablets." Int'l J Pharmaceutics (1999) 189:105-111.
Dittmer, D.K., et al., "Glue-Sniffing Neuropathies," Canadian Family Physician 39:1965-1971 (1993).
Donnelly, C.L., "ADHD Medications: Past and Future," Behavioral Health Management, May/Jun. 2002, 28 & 30.
Dow, "Material Safety Data Sheet: POLYOX(TM) WSR 30" (effective date: Sep. 18, 2001).
Dow, "POLYOX Water-Soluble Resins: Degradation of Water-Soluble Resins," Technical Data (Oct. 2002).
Drug Bank "Oxymorphone," 2015; online, available at: www.dmgbank.ca/chugs/db01192 printed Jul. 1, 2015.
*Endo Pharmaceuticals Inc.* v. *Teva Pharmaceuticals USA, Inc.* (S.D.N.Y 2015)—Redacted Version.
FDA News Release, "FDA approves abuse-deterrent labeling for reformulated OxyContin," Apr. 16, 2013, available at http://www.fda.gov/NewsEvents/Newsroom/Press.Announcements/ucm348252.htm.
FDA, "Notice of Determination that OxyContin Drug Products Covered by NDA 20-553 Were Withdrawn From Sale for Reasons of Safety or Effectiveness." Federal Register, vol. 78, No. 75, Apr. 18, 2013, 23273-23274.
Final Draft Labeling for Concerta Extended-Release Tablets Attachment to Approval Letter (2000); available at: http://www.accessdata.fda.gov/drugsatfda_docs/label/2000/21121lbl.pdf.
Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).
Griffith, D., "Potential new ADHD drug creating lots of big hopes," Sacramento Bee (California), Oct. 30, 2002.
Huang, H. et al., "Preparation of Controlled Release Oral Dosage Forms by Low Temperature Melt Extrusion," AAPS PharmSci. 2000 2(S1).
Jaffe, S.L., "Failed Attempts at Intranasal Abuse of Concerta," Letters to the Editor, J. Am. Acad. Child Adolesc. Psychiatry, 41:1 (Jan. 2002).

(56) References Cited

OTHER PUBLICATIONS

Jannsen Pharmaceuticals, Inc. Concerta Labeling Revisioins, Dec. 12, 2013; online, retrieved from: http://www.accessdata.fda.gov/dmgsatfda_docs/labeV2013/021121s032lbl.pdf.
Joint Claim Construction and Prehearing Statement, dated Jul. 11, 2014. *Janssen Pharmaceuticals, Inc. and Grünenthal GMBH* v. *Actavis Elizabeth LLC and Alkem Laboratories Limited*, Civil Action No. 2:13-cv-04507 CCC-MF (D.N.J.), *Janssen Pharmaceuticals, Inc. and Grünenthal GMBH* v. *Roxane Laboratories, Inc.*, Civil Action No. 2:13-cv-06929 CCC-MF (D.N.J.), and *Janssen Pharmaceuticals, Inc. and Grünenthal GMBH* v. *Alkem Laboratories Limited*, Civil Action No. 2:13-cv-07803 CCC-MF (D.N.J.).
Kibbe, Coloring Agents, in Handbook of Pharmaceutical Excipients (3d ed. 2000).
Kidokoro, M. et al., "Properties of Tablets Containing Granulations of Ibuprofen and Acrylic Copolymers Prepared by Thermal Processes," Pharm Dev. and Tech., 6:263-275 (2001).
Kinjo, N. et al, "Antiplasticization in the Slightly Plasticized Poly(vinyl chloride)," Polymer Journal 4(2):143-153 (1973).
Larhib, H. et al., "Compressing polyethyelene glycols: the effect of compression pressure and speed," Int 'l J Pharmaceutics (1997) 147: 199-205.
Lieberman, H., et al., Pharmaceutical Dosage Forms: Tablets, vol. 2, Ch. 5: Granulation Technology and Tablet Characterization (1990), Table of contents and 245-348.
Lyons et al., "Twitch Interpolation in the Assessment of the Maximum Force-Generating Capacity of the Jaw-Closing Muscles in Man," Arch. Oral. Biol. 41:12, 1161-1168 (1996).
Makki, A, et. al., Eds., A Dictionary of American Idioms, 4th Ed. Barron's, New York (2004), 342-343.
Markovitz, H., et al. "Calculations of Entanglement Coupling Spacings in Linear Polymers." Journal of Physical Chemistry, 1962. 66(8): 1567-1568.
McCrum, N., et al., Principles of Polymer Engineering. 2nd ed., New York: Oxford University Press. 447(1997), Chapter 7, 296-351.
McGinity, J.W. et al., "Melt-Extruded Controlled-Release Dosage Forms" in Pharmaceutical Extrusion Technology, Ghebre-Sellassie, I. and Martin, C., Eds., Marcel Dekker, Inc., New York, 2003, Chapter 10, 183-208.
McQuay, H. et a. "Methods of Therapeutic Trials," Textbook of Pain 1125-1138 (P.D. Wall & R. Melzack eds., Elsevier 4th ed. 1999), Table of Contents and 1125-1138.
Miura et al., "Comparison of Maximum Bite Force and Dentate Status Between Healthy and Frail Elderly Persons," J. Oral Rehabilitation, vol. 28 (2001), pp. 592-595.
Miyagawa, Y. et al., "Controlled-release of diclofenac sodium from wax matrix granulate," Int 'l J. Pharmaceutics (1996) 138:215-224.
National Drug Intelligence Center Information Bulletin "OxyContin Diversion and Abuse" Jan. 2001.
Payne, H. et al., Denatonium Benzoate as a Bitter Aversive Additive in Ethylene Glycol and Methanol-Based Automotive Products, SAE Technical Paper 930589, Abstract (1993).
Pilpel, N., et al. "The effect of temperature on the tensile strength and disintegration of paracetamol and oxytetracylcine tablets," J Pharm Pharmac., 29:389-392 (1977).
POLYOX Water-Soluble Resins NF in Pharmaceutical Applications, Dow Chemical Company, Aug. 2002.
Purdue Pharma LP Material Safety Data Sheet, OxyContin Tablets, 10 mg, 15 mg, 20 mg, 30 mg, 40 mg, 60 mg, Version 16—Sep. 10; available at www.purduephruma.com/msdss/oxycontin_msds.pdf.
Rauwendaal, Chris, PHD, Responsive Expert Report of Chris Rauwendaal, Ph.D. Regarding Expert Report of Michael M. Crowley, Ph.D., dated Jul. 17, 2015.
Repka, M. et al. Pharmaceutical Applications of Hot-Melt Extrusion: Part II. Drug Dev. & Indus. Pharmacy (2007) 33:1043-1057.
Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.
Seitz, J.A.; et al., "Evaluation of the Physical Properties of Compressed Tablets 1: Tablet Hardness and Friability," J. of Pharm. Sci., 54:1353-1357 (1965).
Shah, et al., "Some Effects of Humidity and Heat on the Tableting Properties of Microcrystalline Cellulose Formulations 1," J. of Pharm. Sci., 57:181-182 (1967).
Singhal, et al., Handbook of Indices of Food Quality and Authenticity (1997), "Capsicum" p. 398-299.
Smith, K.L. et al. "High Molecular Weight Polymers of Ethylene Oxide—Plastic Properties." Industrial and Engineering Chemistry, 1958. 50(1): 12-16.
Tapentadol Pre-Review Report, Expert Committee on Drug Dependency Thirty-Fifth Meeting Hammamet, Tunisia, Jun. 4-8, 2012, available at http ://www.who.int/medicines/areas/quality_safety/5.2Tapentadolpre-review.pdf.
Tiwari, D., et al., "Evaluation of polyoxyethylene homopolymers for buccal bioadhesive drug delivery device formulations." AAPS Pharmsci, 1999. 1(3): Article 13.
Wilkins, J.N., "Pharmacotherapy of Schizophrenia Patients with Comorbid Substance Abuse," Schizophrenia Bulletin, 23:215-228 (1997).
World Health Org., Cancer Pain Relief With a Guide to Opioid Availability (2d ed. 1996).
Yin, T.P., et al., "Viscoelastic Properties of Polyethylene Oxide in Rubber-Like State." Journal of Physical Chemistry, 1961. 65(3): 534-538.
Zacny, J. et al. Drug & Alcohol Dependence (2003) 69:215-232.
Zhang, F., "Hot-Melt Extrusion as a Novel Technology to Prepare Sustained-Release Dosage Forms," Dissertation University of Texas at Austin, Dec. 1999.
M. Xu et al., "Evaluation of the coat quality of sustained release pellets by individual pellet dissolution methodology," Int. J. Pharm. 478 (2015) 318-327.
Baxter, J.L. et al., "Hydrodynamics-induced variability in the USP apparatus II dissolution test," International Journal of Pharmaceutics 292 (2005) 17-28.
Bellmann et al., "Development of an advanced in vitro model of the stomach and its evaluation versus human gastric psychology," Food Research International 88 (2016) 191-198.
Dabbagh, et al. "Release of Propranolol Hydrochloride from Matrix Tablets Containing Sodium Carboxymethylcellulose and Hydroxypropylmethylcellulose"; 1999; Pharmaceutical Development and Technology 4(3), 313-324.
Koziolek, M. et al., "Development of a bio-relevant dissolution test device simulating mechanical aspects present in the fed stomach," European Journal of Pharmaceutical Sciences 57 (2014) 250-256.
USP Expert Council, US Pharmacopoeia, Chapter 1092, 2007, 1-15.
Banwarth, Bernard, "Will Abuse-Deterrent Formulations of Opioid Analgesics be Successful in Achieving Their Purpose?", Drugs, 2012, vol. 72, pp. 1713-1723.
Houston, T.E., et al., "Bite Force and Bite Pressure: Comparison of Humans and Dogs," http://www.glapbta.com/BFBP.pdf, 2003, pp. 1-7.
Sigma-Aldrich entry for CAS No. 9010-88-2; www.sigmaaldrich.com/catalog/product/aldrich/182249?lang=en&region=US (downloaded Jun. 2018).
Pharma Tips [online] retrieved on Mar. 22, 2018 from http://ww.pharmatips.in/Articles/Pharmaceutics/Tablet/Co-Processed-Directly-Compressed-Adjutants.aspx May 2011: 10 pages).
PCT International Search Report for PCT Application No. PCT/EP2016/052046 dated Dec. 4, 2016.
U.S. Appl. No. 60/287,509, filed Dec. 2, 2002, Joshi et al.
U.S. Appl. No. 60/288,211, filed Sep. 2, 2004, Oshlack et al.
U.S. Appl. No. 60/310,514, filed Apr. 3, 2003, Oshlack et al.
U.S. Appl. No. 60/310,534, filed Apr. 10, 2003, Wright et al.
U.S. Appl. No. 60/376,470, filed Jan. 15, 2004, Ayer et al.
U.S. Appl. No. 60/384,442, filed Dec. 4, 2003, Fink et al.
"Low Substituted Hydroxypropyl Celluslose", Drugs.com, from https://www.drugs.com/inactive/low-susbstitute-hydroxypropyl-cellulose-581.html (2018).
Agarwal, G, et al, "Oral Sustained Release Tablets: An Overview with a Special Emphasis on Matrix Tablet" American Journal of Advanced Drug Delivery, 2017.

(56) References Cited

OTHER PUBLICATIONS

Bannwarth, Bernard, "Will Abuse-Deterrent Formulations of Opioid Analgesics be Successful in Achieving Their Purpose?", Drugs, 2012, vol. 72, pp. 1713-1723.
BASF the chemical company, Kollicoat IR Technical information, Feb. 2013, p. 1-14 (2010).
Befort et al., "The Conserved Asparatate Residue in the Third Putative Transmember Domain," Molecular Pharmacology 1996: 49:216-223 (1996).
Brzeclo, W.,et al., "The Advent of a new Pseudoephedrine Product to Combat Methampetamine Abuse," Am J Drug Alcohol Abuse, 2013: 39(5): 284-290.
Claffey et al, "Amphetamine Adducts of Melanin Intermediates Demonstrated by Matrix-Assisted Laser Desorption Ionization Time-of-Flight Mass Spectrometry," Chem. Res. Toxicol. 2001, 14, 1339-1344.
COMPAP 90 technical data sheet Mar. 2014; 1 page.
De Brabander C., et al., "Development and evaluation of sustained release mini-matrices prepared via hot melt extrusion," Journal of Controlled Release 89 (2003), 235-247.
Definition GRANULE, Merriam-Webster, accessed online Jun. 28, 2018 (2018).
Domino E.F. (1991) Nicotine: A Unique Psychoactive Drug. In: Adlkofer F., Thurau K. (eds.) Effects of Nicotine on Biological Systems. APS Advances in Pharmacological Sciences. Birkhaeuser Basel (1991).
Ely et al., "Lithium-Ammonia Reduction of Ephedrine to Methamphetamine: An Unusual Clandestine Synthesis," Technical Note, 1990, 720-723.
European Pharmacopeia, 7th Ed. 2.2.8 and 2.2.10, 27ff. (2010).
European Pharmacopoeia 3.0, 2.9.8 "Resistance to Crushing of Tablets", 1997, p. 135.
Evans, J.C, et. al. "Optimal tocopherol concentrations to inhibit soybean oil oxidation," Journal of the American Oil Chemists' Society 79.1 (2002). 47-51.
Evekeo, (Amphetamine Sulfate) for treating patients with ADHD website ([online] https://www.evekeo.com.about-evekeo; 2019:5 pages), 2019.
Extended European Search Report for Application No. EP 16182124.4-1455, dated Jan. 17, 2017.
Extended European Search Report for Application No. EP 17173240.7, dated Nov. 28, 2017.
Fitzpatrick, J., "The influence of Superdisintegrants on Immediate Release," By Pharmaceutical Technology Editions [online] retrieved from http://www.pharmatech.com/influence-superdisintegrants-immediate-release; vol. 21, issue 6 (Jun. 1, 2011).
Furu et al. "use of ADHD drugs in the Nordic countries: a population-based comparison study," Acta Psychiatrica Scandinavia, May 2010.
Gaitondf, B. "General Principles of Drug Action", 1967, p. 48.
Goodman and Gilman, 1985, 7th edition, chapter 29, 674-715.
Jamini, M., et al, "Sustained Release Matrix Type Drug Delivery System. A Review," Journal of Drug Delivery & Therapeutics; 2012, 2(6), 142-148.
Jedinger, N., et al., Eur. J. Pharm. Biopharm 87 (2014), 217-226.
Kelly, C. et al, "Methamphetamine Synthesis Inhibition: Dissolving Metal Reductions,", Johns Hopkins Univ. Applied Physics Lab., 2015, 1-10.
King, Remington's Pharmaceutical Sciences 17th ed., Chapter 78, p. 1418-1419 (1985).
Kolar et al., "Treatmen of adults with attention-deficit/hyperactivity disorder," Neuropsychiatric Disease and Treatment 2008:4(3):389-403.
Kunalan et al., "Investigation of the Reaction Impurities Associated with Methylamphetamine Synthesized using the Nagai Method," Anal. Chem. 2012, 84, 5744-52.
Lee et al., "Analysis of the impurities in the metamphetamine synthesized by thee different methods from ephedrine and pseudoephedrine," Forensic Science International 161 (2006), 209-215.
Lurie et al., "Chiral Resolution of Cationic Drugs of Forensic Interest," (Analytical Chemistry 1994: 66(22): 4019-4026.
Misal, R, et al., "Matrix Tablet: A Promising Technique for Controlled Drug Delivery," Indo American Journal of Pharmaceutical Research, 2013.
Nickerson, B., Sample Preparation of Pharmaceutical Dosage Forms, Springer, New York (2011); Chapter 1, pp. 3-48.
Patel, et. al., "Poloxamers: A pharmaceutical excipient with therapeutic behaviors," PharmTech, vol. 1, No. 2, pp. 299-300 (Apr. 2009).
Patrick, K., et al., "Pharmacology of Methylphenidate, Amphetamine Enantiomers and Pemoline in Attention-Deficit Hyperactivity Disorder," Human Psychopharmacology, vol. 12, 527-546 (1997).
PCT International Search Report and Written Opinion for PCT Application No. PCT/EP2016/052046 dated Apr. 12, 2016.
PCT International Search Report and Written Opinion for PCT Application No. PCT/EP2017/070396 dated Sep. 8, 2017.
Person et al., Structural Determination of the Principal Byproduct of the Lithium-Ammonia Reduction Method of Methamphetamine Manufacture, J Forensic Sci, Jan. 2005, vol. 50, No. 1, 87-95.
Pharma Tips ([online] retrieved on Mar. 22, 2018 from http://ww.pharmatips.in/Articles/Pharmaceutics/Tablet/Co-Processed-Directly-Compressed-Adjutants.aspx; May 2011: 10 pages).
Pintauro, Nicholas, D., Food Flavoring Processes, Table of Content. Park Ridge, NJ and London, UK, 1976.
POLYOX Water-Soluble Resins in Pharmaceutical Applications. Dow Chemicals Published 2004.
POLYOX, 2004, online retrieved on Oct. 15, 2018.
Presley, B. et al., "Efficiency of Extraction and Conversion of Pseudoephedrine to Methamphetamine from Tamper-Resistant and Non-Tamper-Resistant Formulations," Journal of Pharmaceutical and Biomedical Analysis , 2018, 16-22.
Qi et al, "An Investigation into the Crystallisation Behavior of an Amorphous Cryomilled Pharmaceutical Material Above and Below the Glass Transition Temperature," Journal of Pharmaceutical Sciences, 2009, 196-208.
Quadros, E. et al.. "Evaluation of a novel colonic delivery device in vivo," STP Pharma Sci. 5, 77-82 (1995).
Quinn, M.E. "Alpha Tocopherol" in Handbook of Pharmaceuical Excipients, Sixth Edition (2009), 31-33.
Rasmussen, N. "America's First Amphetamine Epidemic 1929-1971," American Journal of Public Health 2008:98(6): 974-985.
Remington, Chapter 45, pp. 996-1035. (2000) (Full Translation Attached).
Romach et al. "Update on tamper-resistant drug formulations," Drug and Alcohol Dependence, 130 (2013), 13-23.
Salouros et al., Isolation and Identification of Three By-Products Found in Methylamphetamine Synthesized by the Emde Route2010, 605-615.
Skinner, Harry F., "Methamphetamine Synthesis via Hydriodic Acid/Red Phosphorus Reduction of Ephedrine," Forensic Science International, 48 (1990), 123-134.
Sprockel, et. al, "A melt-extrusion process for manufacturing matrix drug delivery systems," Int. Journal of Pharmaceutics 155 (1997) 191-199.
Sumitomo Seika Chemicals, Co., Ltd, "Certificate of Analysis," Product: Polyethylene Oxide; Grade: PEO-18NF; Feb. 2, 2016.
Sumitomo Seika Chemicals, Co., Ltd, "Certificate of Analysis," Product: Polyethylene Oxide; Grade: PEO-20NF; Feb. 3, 2016.
Sumitomo Seika Chernicals, Co., Ltd, "Certificate of Analysis," Product: Polyethylene Oxide; Grade: PEO-20NF; Jan. 23, 2012.
Sumitomo Seika Chemicals, Co., Ltd, "Certificate of Analysis," Product: Polyethylene Oxide; Grade: PEO-20NF; May 15, 2013.
Suzuki, T, "Blood-brain barrier transport of opioid analgesics," Abstract, Yakugaki Zasshi; 131(10):1445-51 (2011).
Targin(R) Product Monograph. Purdue Pharma. Revised Mar. 1, 2016.
Theeuwes, Felix et al., Osmotic Systems for Colon-Targeted Drug Delivery in Colonic Drug Absorption and Metabotism (Peter R. Bieck ed., 1993).
Turkington, R., "Amphetamines," in Chemicals used for Illegal Purposes. A Guide for first Responders to Identify Explosives, Recreational Drugs, and Poisons, 2010, p. 247.

(56) References Cited

OTHER PUBLICATIONS

Vezin, W. et al, "Adjustment of precompression force to reduce mixing-time dependence of tablet tensile strength," J. Pharm. Pharmacol. 1983, 35: 555-558 (Mar. 28, 1983).

Weinhold, et al. "Buprenorphine alone and in combination with naloxone in non-dependent humans." Drug & Alcohol Dependence 30.3 (1992): 263-274.

Wooten, Marvin R. et al., Intracerebral Hemorrhage and Vasculitis Related to Ephedrine Abuse, 13 Annals of Neurology 337 (1983).

Martin et al., "Applications of Polyethylene Oxide (POLYOX) in Hydrophilic Matrices," in Hydrophilic Matrix Tablets for Oral Controlled Release, Springer, New York, 2014, Chapter 5, pp. 123-141.

Thumma et al., "Influence of Plasticizers on the Stability of a Prodrug of D9-Tetrahydrocannabinol Incorporated in poly(Ethyelen Oxide) Matrices", Eur J. Pharm Biopharm. Oct. 2008 (70(2): 605-614.

Heal et al. "Amphetamine, past and present—a pharmacological and clinical perspective," Journal of Psychology 2013:27(6):479-496 (2013).

Vosburg, et al, "A comparison among tapentadol tamper-resistant formulations (TRF) and OxyCotin® (non-TRF) in prescription opioid abusers," 2013; Society for the Study of Addiction; Addiction, vol. 108, pp. 1095-1106.

Lefnaoui et al., Synthesis and evaluation of the structural and physiochemical properties of carboxymethyl pregelatinized starch as a pharmaceutical excipient, Saudi Pharmaceutical Jourani, Feb. 2015:23:698(2015).

Lopez-Solis et al., Effect of disintegrants with different hygroscopicity on dissolution of Norfloxacin/Pharmatose DCL 11 tablets, International Journal of Pharmaceutics 2001:216:127(2001).

\* cited by examiner

TAMPER-RESISTANT DOSAGE FORM CONTAINING ETHYLENE-VINYL ACETATE POLYMER

This application claims priority of European Patent Application No. EP 13176303.9, filed Jul. 12, 2013, the contents of which are incorporated herein by reference.

FIELD OF THE INVENTION

The invention relates to a tamper-resistant, oral pharmaceutical dosage form comprising a pharmacologically active ingredient having psychotropic action and an ethylene-vinyl acetate (EVA) polymer, which dosage form provides resistance against solvent extraction, resistance against grinding, and resistance against dose-dumping in aqueous ethanol.

BACKGROUND OF THE INVENTION

A large number of pharmacologically active substances have a potential for being abused or misused, i.e. they can be used to produce effects which are not consistent with their intended use. Thus, e.g. opioids which exhibit an excellent efficacy in controlling severe to extremely severe pain are frequently abused to induce euphoric states similar to being intoxicated. In particular, active substances which have a psychotropic effect are abused accordingly.

To enable abuse, the corresponding pharmaceutical dosage forms, such as pharmaceutical dosage forms or capsules are crushed, for example ground by the abuser, the active substance is extracted from the thus obtained powder using a preferably aqueous liquid and after being optionally filtered through cotton wool or cellulose wadding, the resultant solution is administered parenterally, in particular intravenously. This type of dosage results in an even faster diffusion of the active substance compared to the oral abuse, with the result desired by the abuser, namely the kick. This kick or these intoxication-like, euphoric states are also reached if the powdered pharmaceutical dosage form is administered nasally, i.e. is sniffed.

Various concepts for the avoidance of drug abuse have been developed.

It has been proposed to incorporate in pharmaceutical dosage forms aversive agents and/or antagonists in a manner so that they only produce their aversive and/or antagonizing effects when the pharmaceutical dosage forms are tampered with. However, the presence of such aversive agents is principally not desirable and there is a need to provide sufficient tamper-resistance without relying on aversive agents and/or antagonists.

Another concept to prevent abuse relies on the mechanical properties of the pharmaceutical dosage forms, particularly an increased breaking strength (resistance to crushing). The major advantage of such pharmaceutical dosage forms is that comminuting, particularly pulverization, by conventional means, such as grinding in a mortar or fracturing by means of a hammer, is impossible or at least substantially impeded. Thus, the pulverization, necessary for abuse, of the pharmaceutical dosage forms by the means usually available to a potential abuser is prevented or at least complicated. Such pharmaceutical dosage forms are useful for avoiding drug abuse of the pharmacologically active ingredient contained therein, as they may not be powdered by conventional means and thus, cannot be administered in powdered form, e.g. nasally. The mechanical properties, particularly the high breaking strength of these pharmaceutical dosage forms renders them tamper-resistant. In the context of such tamper-resistant pharmaceutical dosage forms it can be referred to, e.g., WO 2005/016313, WO 2005/016314, WO 2005/063214, WO 2005/102286, WO 2006/002883, WO 2006/002884, WO 2006/002886, WO 2006/082097, WO 2006/082099, and WO2009/092601.

Besides tampering of pharmaceutical dosage forms in order to abuse the drugs contained therein, the potential impact of concomitant intake of ethanol on the in vivo release of drugs from modified release oral formulations (dose-dumping) has recently become an increasing concern. Controlled or modified release formulations typically contain a higher amount of the pharmacologically active ingredient relative to its immediate release counterpart. If the controlled release portion of the formulation is easily defeated, the end result is a potential increase in exposure to the active drug and possible safety concerns. In order to improve safety and circumvent intentional tampering (e.g. dissolving a controlled release pharmaceutical dosage form in ethanol to extract the drug), a reduction in the dissolution of the modified release fractions of such formulations, in ethanol, may be of benefit. Accordingly, the need exists to develop new formulations having reduced potential for dose dumping in alcohol.

The properties of these pharmaceutical dosage forms of the prior art, however, are not satisfactory in every respect.

C. Vervaet et al., Eur. J. Pharm. Biopharm. 77, 2011, 297-305 disclose ethylene vinyl acetate as matrix for oral sustained release dosage forms which contain metoprolol tartrate as the pharmacologically active ingredient and are produced via hot-melt extrusion. C. Vervaet et al., Eur. J. Pharm. Biopharm. 82, 2012, 526-533 discloses sustained release of metoprolol tartrate from hot-melt extruded matrices based on ethylene vinyl acetate and polyethylene oxide. B. Sreenivasa Rao et al., Indian J. Pharm. Sci. 65, 2003, 496-502 disclose a method of preparation of sintered matrix tablets of rifampicin with ethylene-vinyl acetate copolymer for controlling the release rate. However, these references are fully silent on the possibility of preparing tamper-resistant pharmaceutical dosage forms from ethylene-vinyl acetate (EVA) polymers.

WO 2009/051819 A1 disclose implants for delivery of therapeutic agents such as opioids, and the manufacture and uses of such implants. WO 03/070191 A1 discloses a transdermal-delivery device which is said to be tamper-resistant and comprises an opioid, or a pharmaceutically acceptable salt thereof, and an acyl opiod antagonist, or a pharmaceutically acceptable salt thereof.

It is an object of the invention to provide tamper-resistant and dose-dumping resistant, oral pharmaceutical dosage forms containing a pharmacologically active ingredient having psychotropic action which have advantages compared to the pharmaceutical dosage forms of the prior art.

This object has been achieved as described hereinbelow.

It has been surprisingly found that a pharmaceutical dosage form comprising ethylene-vinyl acetate (EVA) polymer and a pharmacologically active ingredient having psychotropic action can be prepared, wherein the pharmaceutical dosage form exhibits tamper resistance, especially in terms of resistance against solvent extraction of the pharmacologically active ingredient, resistance against grinding of the pharmaceutical dosage form, respectively, and resistance against dose-dumping of the pharmacologically active ingredient in aqueous ethanol.

BRIEF DESCRIPTION OF THE DRAWINGS

The invention will now be described in greater detail with reference to the drawings, wherein.

Figure 1:
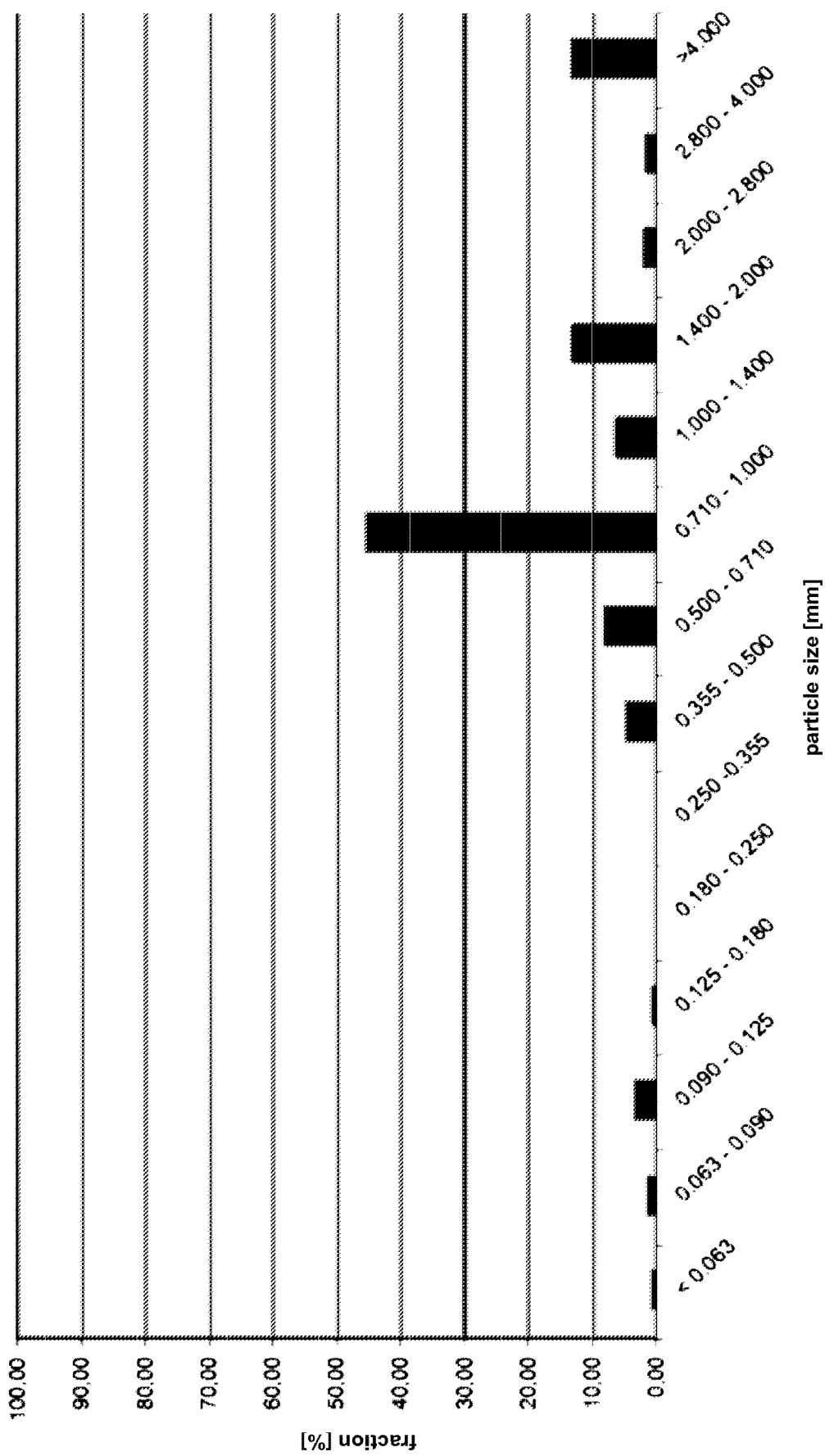
FIG. 1 is a graph depicting the results of the sieving analysis referred to in Example 1.

A first aspect of the invention relates to a tamper-resistant, oral pharmaceutical dosage form comprising a pharmacologically active ingredient having psychotropic action and an ethylene-vinyl acetate (EVA) polymer, which dosage form provides resistance against solvent extraction, resistance against grinding, and resistance against dose-dumping in aqueous ethanol.

Preferably, the pharmaceutical dosage form according to the invention is thermoformed, more preferably hot-melt extruded. Thermoforming preferably means that in the course of the manufacture of the pharmaceutical dosage form the mixture comprising the EVA polymer and the pharmacologically active ingredient is heated to a temperature above ambient temperature, preferably at least 60° C. or at least 80° C., and compressed, preferably at pressures of at least 1 bar or at least 2 bar, more preferably at least 10 bar or at least 30 bar. The compression force may be exerted prior to, during or subsequent to the application of heat.

As used herein, the term "pharmaceutical dosage form" refers to a pharmaceutical entity that is comprised of a pharmacologically active ingredient and which is actually administered to, or taken by, a patient. It may be compressed or molded in its manufacture, and it may be of almost any size, shape, weight, and color.

The pharmaceutical dosage form is preferably solid or semisolid.

Examples of pharmaceutical dosage forms according to the invention include, but are not limited to, tablets, capsules, pills, granules, pellets, sachets and effervescent, powders, and the like. In an embodiment of the present invention, the composition is formulated in a capsule. In accordance with this embodiment, the pharmaceutical dosage form comprises a hard or soft gelatin capsule.

Most pharmaceutical dosage forms are intended to be swallowed whole and accordingly, the pharmaceutical dosage forms according to the invention are designed for oral administration.

In a preferred embodiment, the pharmaceutical dosage form according to the invention is monolithic. In this regard, monolithic preferably means that the pharmaceutical dosage form is formed or composed of material without joints or seams or consists of or constitutes a single unit.

In another preferred embodiment, the pharmaceutical dosage form according to the invention is not monolithic. Preferably, the pharmaceutical dosage form according to the invention is multiparticulate, i.e. comprises a multitude of particles. An advantage of multiparticulate pharmaceutical dosage forms is that the particles may be mixed in different amounts to thereby produce pharmaceutical dosage forms of different strengths.

In a preferred embodiment, the pharmaceutical dosage form according to the invention can be regarded as a MUPS formulation (multiple unit pellet system). Preferably, the pharmaceutical dosage form according to the invention contains all ingredients in a dense compact unit which in comparison to capsules has a comparatively high density. Under these circumstances, the pharmaceutical dosage forms according to the invention preferably comprise subunits having different morphology and properties, namely drug-containing particles and an outer matrix material, wherein the particles form a discontinuous phase within the outer matrix material. The constituents of the outer matrix material are preferably different from the constituents of the drug-containing particles. Preferably, the outer matrix material neither contains a pharmacologically active ingredient having psychotropic action nor an EVA polymer.

The particles typically have mechanical properties that differ from the mechanical properties of the outer matrix material. Preferably, the particles have a higher mechanical strength than the outer matrix material. The particles can preferably be visualized by conventional means such as solid state nuclear magnetic resonance spectroscopy, raster electron microscopy, terahertz spectroscopy and the like.

The pharmaceutical dosage form according to the invention has preferably a total weight in the range of 0.01 to 1.5 g, more preferably in the range of 0.05 to 1.2 g, still more preferably in the range of 0.1 g to 1.0 g, yet more preferably in the range of 0.2 g to 0.9 g, and most preferably in the range of 0.3 g to 0.8 g. In a preferred embodiment, the total weight of the pharmaceutical dosage form is within the range of 350±300 mg, more preferably 350±250 mg, still more preferably 350±200 mg, yet more preferably 350±150 mg, most preferably 350±100 mg, and in particular 350±50 mg. In another preferred embodiment, the total weight of the pharmaceutical dosage form is within the range of 500±450 mg, more preferably 500±300 mg, still more preferably 500±200 mg, yet more preferably 500±150 mg, most preferably 500±100 mg, and in particular 500±50 mg.

In a preferred embodiment, the pharmaceutical dosage form according to the invention is a round pharmaceutical dosage form. Pharmaceutical dosage forms of this embodiment preferably have a diameter in the range of about 1 mm to about 30 mm, in particular in the range of about 2 mm to about 25 mm, more in particular about 5 mm to about 23 mm, even more in particular about 7 mm to about 13 mm; and a thickness in the range of about 1.0 mm to about 12 mm, in particular in the range of about 2.0 mm to about 10 mm, even more in particular from 3.0 mm to about 9.0 mm, even further in particular from about 4.0 mm to about 8.0 mm.

In another preferred embodiment, the pharmaceutical dosage form according to the invention is an oblong pharmaceutical dosage form. Pharmaceutical dosage forms of this embodiment preferably have a lengthwise extension (longitudinal extension) of about 1 mm to about 30 mm, in particular in the range of about 2 mm to about 25 mm, more in particular about 5 mm to about 23 mm, even more in particular about 7 mm to about 20 mm; a width in the range of about 1 mm to about 30 mm, in particular in the range of about 2 mm to about 25 mm, more in particular about 5 mm to about 23 mm, even more in particular about 7 mm to about 13 mm; and a thickness in the range of about 1.0 mm to about 12 mm, in particular in the range of about 2.0 mm to about 10 mm, even more in particular from 3.0 mm to about 9.0 mm, even further in particular from about 4.0 mm to about 8.0 mm.

When the pharmaceutical dosage form according to the invention is monolithic, it preferably has an extension in any direction of at least 2.0 mm, more preferably at least 2.5 mm, still more preferably at least 3.0 mm, yet more preferably at least 3.5 mm, even more preferably at least 4.0 mm, most preferably at least 4.5 mm and in particular at least 5.0 mm. Preferably, when the dosage form is monolithic, it has an extension in any direction of more than 2.0 mm.

For the purpose of specification, "in any direction" preferably means in every direction in the three-dimensional space.

The pharmaceutical dosage form according to the invention may optionally comprise a coating, e.g. a cosmetic coating. The coating is preferably applied after formation of the pharmaceutical dosage form. The coating may be applied prior to or after the curing process. The pharmaceutical dosage forms according to the invention are preferably film coated with conventional film coating compositions. Suitable coating materials are commercially available, e.g. under the trademarks Opadry® and Eudragit®.

Examples of suitable materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na-CMC), poly(meth)-acrylates, such as aminoalkylmethacrylate copolymers, methacrylic acid methylmethacrylate copolymers, methacrylic acid methylmethacrylate copolymers; vinyl polymers, such as polyvinylpyrrolidone, polyvinyl alcohol, polyvinylacetate; and natural film formers.

The coating can be resistant to gastric juices and dissolve as a function of the pH value of the release environment. By means of this coating, it is possible to ensure that the pharmaceutical dosage form according to the invention passes through the stomach undissolved and the active compound is only released in the intestines. The coating which is resistant to gastric juices preferably dissolves at a pH value of between 5 and 7.5.

The coating can also be applied e.g. to improve the aesthetic impression and/or the taste of the pharmaceutical dosage forms and the ease with which they can be swallowed. Coating the pharmaceutical dosage forms according to the invention can also serve other purposes, e.g. improving stability and shelf-life. Suitable coating formulations comprise a film forming polymer such as, for example, polyvinyl alcohol or hydroxypropyl methylcellulose, e.g. hypromellose, a plasticizer such as, for example, a glycol, e.g. propylene glycol or polyethylene glycol, an opacifier, such as, for example, titanium dioxide, and a film smoothener, such as, for example, talc. Suitable coating solvents are water as well as organic solvents. Examples of organic solvents are alcohols, e.g. ethanol or isopropanol, ketones, e.g. acetone, or halogenated hydrocarbons, e.g. methylene chloride. Coated pharmaceutical dosage forms according to the invention are preferably prepared by first making the cores and subsequently coating said cores using conventional techniques, such as coating in a coating pan.

Preferably, the pharmaceutical dosage form according to the invention comprises a prolonged release matrix.

The prolonged release matrix in turn preferably comprises the EVA polymer as prolonged release matrix material and optionally additional prolonged release matrix material.

In a preferred embodiment, the prolonged release matrix does not contain any additional prolonged release matrix material.

The pharmacologically active ingredient is preferably embedded in the prolonged release matrix comprising the EVA polymer. Preferably, the pharmacologically active ingredient is dispersed in the prolonged release matrix.

Preferably, the pharmaceutical dosage form provides prolonged release of the pharmacologically active ingredient. Particularly preferably, the prolonged release matrix comprising the EVA polymer provides prolonged release of the pharmacologically active ingredient embedded therein.

In a preferred embodiment,
(i) the pharmacologically active ingredient is embedded in a prolonged release matrix comprising the EVA polymer; and/or
(ii) the pharmaceutical dosage form provides prolonged release of the pharmacologically active ingredient.

When the pharmaceutical dosage form according to the invention is monolithic and comprises a prolonged release matrix, the prolonged release matrix preferably forms the body of the pharmaceutical dosage form.

When the pharmaceutical dosage form according to the invention is multiparticulate, e.g. in form of pellets, the particles preferably comprise the prolonged release matrix and at least a portion of the total amount of the pharmacologically active ingredient that is contained in the pharmaceutical dosage form. Preferably, the particles comprise the total amount of the pharmacologically active ingredient that is contained in the pharmaceutical dosage form.

When the pharmaceutical dosage form according to the invention can be regarded as a MUPS formulation which preferably comprises drug-containing particles and an outer matrix material, the outer matrix material is not a constituent of the prolonged release matrix and is to be distinguished from the prolonged release matrix material and the optionally present additional prolonged release matrix material of the prolonged release matrix of the pharmaceutical dosage form according to the invention.

For the purpose of specification, the term "particle" refers to a discrete mass of material that is solid, e.g. at 20° C. or at room temperature or ambient temperature. Preferably a particle is solid at 20° C. Preferably, the particles are monoliths. Preferably, the pharmacologically active ingredient and the EVA polymer are intimately homogeneously distributed in the particles so that the particles do not contain any segments where either pharmacologically active ingredient is present in the absence of EVA polymer or where EVA polymer is present in the absence of pharmacologically active ingredient.

When the pharmaceutical dosage form is multiparticulate, it preferably comprises a multitude i.e. plurality of particles containing pharmacologically active ingredient (drug-containing particles) and may optionally further comprise particles not containing any pharmacologically active ingredient (drug-free particles).

In a preferred embodiment, the pharmaceutical dosage form preferably comprises at most 10, more preferably at most 9, still more preferably at most 8, yet more preferably at most 7, even more preferably at most 6, most preferably at most 5, and in particular at most 4 or 3 or 2 drug-containing particles. In another preferred embodiment, the pharmaceutical dosage form preferably comprises at least 2, more preferably at least 4, still more preferably at least 6, yet more preferably at least 8, even more preferably at least 10, most preferably at least 15 and in particular at least 20 or at least 100 or at least 1000 drug-containing particles.

When the particles are film coated, the EVA polymer is preferably homogeneously distributed in the core of the particles, i.e. the film coating preferably does not contain EVA polymer.

When the particles contain a prolonged release matrix and are film coated, the prolonged release matrix is preferably homogeneously distributed in the core of the particles, i.e. the film coating preferably neither contains prolonged release matrix material nor optionally present additional prolonged release matrix material.

The particles are preferably of macroscopic size, typically the average diameter is within the range of from 100 µm to 2000 µm, preferably 200 µm to 1500 µm, more preferably 300 µm to 1500 µm, still more preferably 400 µm to 1500 µm, most preferably 500 µm to 1500 µm, and in particular 600 µm to 1500 µm. Preferably, the particles in the pharmaceutical dosage form have an average particle size of at least 50 µm, more preferably at least 100 µm, still more preferably at least 150 µm or at least 200 µm, yet more preferably at least 250 µm or at least 300 µm, most preferably at least 400 µm or at least 500 µm, and in particular at least 550 µm or at least 600 µm. Preferably, the particles in the pharmaceutical dosage form have an average particle size of at least 700 µm, more preferably at least 800 µm, most preferably at least 900 µm and in particular at least 1000 µm.

In a preferred embodiment, the pharmaceutical dosage forms according to the invention comprise particles as a discontinuous phase, i.e. the particles form a discontinuous phase in an outer matrix material which in turn preferably forms a continuous phase. In this regard, discontinuous means that not each and every particle is in intimate contact with another particle but that the particles are at least partially separated from one another by the outer matrix material in which the particles are embedded. In other words, the particles preferably do not form a single coherent mass within the pharmaceutical dosage forms according to the invention.

Preferably, when the pharmaceutical dosage form is multiparticulate, the content of the particles in the pharmaceutical dosage forms according to the invention is at most 95 wt.-%, more preferably at most 90 wt.-%, still more preferably at most 85 wt.-%, yet more preferably at most 80 wt.-%, most preferably at most 75 wt.-% and in particular at most 70 wt.-%, based on the total weight of the pharmaceutical dosage forms.

Preferably, when the pharmaceutical dosage form is multiparticulate, the content of the particles in the pharmaceutical dosage forms according to the invention is at least 10 wt.-%, at least 15 wt.-%, at least 20 wt.-% or at least 25 wt.-%; more preferably at least 30 wt.-%, at least 35 wt.-%, at least 40 wt.-% or at least 45 wt.-%; most preferably at least 50 wt.-%, at least 55 wt.-%, at least 60 wt.-% or at least 65 wt.-%; and in particular at least 70 wt.-%, at least 75 wt.-%, at least 80 wt.-% or at least 85 wt.-%; based on the total weight of the pharmaceutical dosage form.

When the pharmaceutical dosage form is multiparticulate, the shape of the particles is not particularly limited. As the particles are preferably manufactured by hot-melt extrusion, preferred particles present in the pharmaceutical dosage forms according to the invention are generally cylindrical in shape. The diameter of such particles is therefore the diameter of their circular cross section. The cylindrical shape is caused by the extrusion process according to which the diameter of the circular cross section is a function of the extrusion die and the length of the cylinders is a function of the cutting length according to which the extruded strand of material is cut into pieces of preferably more or less predetermined length.

Typically, the aspect ratio is regarded as an important measure of the spherical shape. The aspect ratio is defined as the ratio of the maximal diameter ($d_{max}$) and its orthogonal Feret-diameter. For aspherical particles, the aspect ratio has values above 1. The smaller the value the more spherical is the particle. In a preferred embodiment, the aspect ratio of the particles is at most 1.40, more preferably at most 1.35, still more preferably at most 1.30, yet more preferably at most 1.25, even more preferably at most 1.20, most preferably at most 1.15 and in particular at most 1.10. In another preferred embodiment, the aspect ratio of the particles is at least 1.10, more preferably at least 1.15, still more preferably at least 1.20, yet more preferably at least 1.25, even more preferably at least 1.30, most preferably at least 1.35 and in particular at least 1.40.

Preferred particles have an average length and average diameter of about 1000 µm or less. When the particles are manufactured by extrusion technology, the "length" of particles is the dimension of the particles that is parallel to the direction of extrusion. The "diameter" of particles is the largest dimension that is perpendicular to the direction of extrusion.

Particularly preferred particles have an average diameter of less than about 2000 µm, more preferably less than about 1000 or 800 µm, still more preferably of less than about 650 µm. Especially preferred particles have an average diameter of less than 700 µm, particularly less than 600 µm, still more particularly less than 500 µm, e.g. less than 400 µm. Particularly preferred particles have an average diameter in the range of 200-1500 µm, more preferably 400-800 µm, still more preferably 450-700 µm, yet more preferably 500-650 µm, e.g. about 500-600 µm. Further preferred particles have an average diameter of between about 300 µm and about 400 µm, of between about 400 µm and 500 µm, or of between about 500 µm and 600 µm, or of between 600 µm and 700 µm or of between 700 µm and 800 µm.

In a preferred embodiment, particles that are present in the pharmaceutical dosage forms according to the invention have an average length in the range of 500 to 5000 µm, more preferably 750 to 4600 µm, still more preferably 1000 to 4200 µm, yet more preferably 1250 to 3800 µm, even more preferably 1500 to 3400 µm, most preferably 1750 to 3200 µm and in particular 2000 to 3000 µm. According to this embodiment, particles that are present in the pharmaceutical dosage forms according to the invention preferably have an average length of less than about 4000 µm, more preferably less than about 3000 µm, still more preferably less than about 2000 µm, e.g. a length of about 1800 µm, about 1600 µm about 1400 µm, about 1200 µm or about 1000 µm.

In another preferred embodiment, particles that are present in the pharmaceutical dosage forms according to the invention have an average length in the range of 200 to 1000 µm, more preferably 400 to 800 µm, still more preferably 450 to 700 µm, yet more preferably 500 to 650 µm, e.g. about 500 to 600 µm. According to this embodiment, particles that are present in the pharmaceutical dosage forms according to the invention preferably have an average length of less than about 1000 µm, more preferably less than about 800 µm, still more preferably less than about 650 µm, e.g. a length of about 800 µm, about 700 µm about 600 µm, about 500 µm, about 400 µm or about 300 µm. Especially preferred particles have an average length of less than 700 µm, particularly less than 650 µm, still more particularly less than 550 µm, e.g. less than 450 µm.

The minimum average length of the particles is determined by the cutting step and may be, e.g. 4.0 mm, 3.0 mm, 2.0 mm, 2.5 mm, 2.0 mm, 1.5 mm, 1.0 mm, 0.9 mm, 0.8 mm, 0.7 mm, 0.6 mm, 0.5 mm, 0.4 mm, 0.3 mm or 0.2 mm.

In a preferred embodiment, when the pharmaceutical dosage form is multiparticulate, the individual drug-containing particles have an extension in any direction of at least 2.0 mm, more preferably at least 2.2 mm, still more preferably at least 2.5 mm, yet more preferably at least 2.8 mm, even more preferably at least 3.0 mm, most preferably at least 3.2 mm, and in particular at least 3.5 mm or 4.0 mm. Preferably, when the dosage form is multiparticulate, the individual drug-containing particles have an extension in any direction of more than 2.0 mm.

In a preferred embodiment, the pharmaceutical dosage form according to the invention is monolithic and has an extension in any direction of more than 2.0 mm; or is multiparticulate, wherein the individual drug-containing particles have an extension in any direction of more than 2.0 mm.

Particularly preferably, the pharmaceutical dosage form according to the invention is monolithic and has an extension in any direction of at least 2.0 mm; or is multiparticulate, wherein the individual drug-containing particles have an extension in any direction of at least 2.0 mm.

In another preferred embodiment,
the pharmaceutical dosage form according to the invention is monolithic and has an extension in any direction of at least 2.5 mm; or is multiparticulate, wherein the individual drug-containing particles have an extension in any direction of at least 2.2 mm; or
the pharmaceutical dosage form according to the invention is monolithic and has an extension in any direction of at least 3.0 mm; or is multiparticulate, wherein the individual drug-containing particles have an extension in any direction of at least 2.5 mm; or
the pharmaceutical dosage form according to the invention is monolithic and has an extension in any direction of at least 3.5 mm; or is multiparticulate, wherein the individual drug-containing particles have an extension in any direction of at least 2.8 mm; or
the pharmaceutical dosage form according to the invention is monolithic and has an extension in any direction of at least 4.0 mm; or is multiparticulate, wherein the individual drug-containing particles have an extension in any direction of at least 3.0 mm; or
the pharmaceutical dosage form according to the invention is monolithic and has an extension in any direction of at least 4.5 mm; or is multiparticulate, wherein the individual drug-containing particles have an extension in any direction of at least 3.2 mm; or
the pharmaceutical dosage form according to the invention is monolithic and has an extension in any direction of at least 5.0 mm; or is multiparticulate, wherein the individual drug-containing particles have an extension in any direction of at least 3.5 mm or at least 4.0 mm.

The size of particles may be determined by any conventional procedure known in the art, e.g. laser light scattering, sieve analysis, light microscopy or image analysis.

Preferably, when the pharmaceutical dosage form is multiparticulate, the plurality of particles that is contained in the pharmaceutical dosage form according to the invention has an arithmetic average weight, in the following referred to as "aaw", wherein at least 70%, more preferably at least 75%, still more preferably at least 80%, yet more preferably at least 85%, most preferably at least 90% and in particular at least 95% of the individual particles contained in said plurality of particles has an individual weight within the range of aaw ±30%, more preferably aaw ±25%, still more preferably aaw ±20%, yet more preferably aaw ±15%, most preferably aaw ±10%, and in particular aaw ±5%. For example, if the pharmaceutical dosage form according to the invention contains a plurality of 100 particles and aaw of said plurality of particles is 1.00 mg, at least 75 individual particles (i.e. 75%) have an individual weight within the range of from 0.70 to 1.30 mg (1.00 mg ±30%).

In a preferred embodiment, the particles, more preferably the drug-containing particles, each have a weight of less than 20 mg, more preferably less than 18 mg, still more preferably less than 16 mg, yet more preferably less than 14 mg, even more preferably less than 12 mg or less than 10 mg, most preferably less than 8 mg, and in particular less than 6 or 4 mg. According to this embodiment, all individual particles each preferably have a weight of from 1 to 19 mg, more preferably 1.5 to 15 mg, still more preferably 2.0 to 12 mg, yet more preferably 2.2 to 10 mg, even more preferably 2.5 to 8 mg, most preferably 2.8 to 6 mg and in particular 3 to 5 mg.

In another preferred embodiment, the particles, more preferably the drug-containing particles, each have a weight of 20 mg or more. According to this embodiment, all individual particles preferably each have a weight of at least 30 mg, more preferably at least 40 mg, still more preferably at least 50 mg, most preferably at least 60 mg and in particular at least 100 mg. Preferably, all individual particles each have a weight of from 20 to 1000 mg, more preferably 30 to 800 mg, still more preferably 40 to 600 mg, yet more preferably 50 to 400 mg, even more preferably 60 to 200 mg, most preferably 70 to 150 mg and in particular 80 to 120 mg. According to this embodiment, the particles of the pharmaceutical dosage form, more preferably the drug-containing particles of the pharmaceutical dosage form, preferably each have an extension in any given direction of at least 2.0 mm or 3.0 mm and have a weight of at least 20 mg.

In a preferred embodiment, when the pharmaceutical dosage form is multiparticulate, the particles are not film coated.

In another preferred embodiment, when the pharmaceutical dosage form is multiparticulate, the particles are film coated. The particles according to the invention can optionally be provided, partially or completely, with a conventional coating. The particles are preferably film coated with conventional film coating compositions. Suitable coating materials are commercially available, e.g. under the trademarks Opadry® and Eudragit®.

Examples of suitable materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na-CMC), ethylcellulose (EC), cellulose acetate phthalate (CAP), hydroxypropylmethylcellulose phthalate (HPMCP); poly(meth)acrylates, such as aminoalkylmethacrylate copolymers, ethylacrylate methylmethacrylate copolymers, methacrylic acid methylmethacrylate copolymers, methacrylic acid methylmethacrylate copolymers; vinyl polymers, such as polyvinylpyrrolidone, polyvinylacetatephthalate, polyvinyl alcohol, polyvinyl alcohol-polyethylene glycol graft copolymers, polyvinylacetate; and natural film formers.

The coating material may contain excipients such as stabilizers (e.g. surfactants such as macrogol cetostearylether, sodium dodecylsulfate, and the like). Suitable excipients of film coating materials are known to the skilled person.

In a particularly preferred embodiment, the coating is water-soluble.

Though less preferred, the coating can principally be resistant to gastric juices and dissolve as a function of the pH value of the release environment. By means of this coating, it is possible to ensure that the pharmaceutical dosage form according to the invention passes through the stomach undissolved and the active compound is only released in the intestines. The coating which is resistant to gastric juices preferably dissolves at a pH value of between 5 and 7.5. Corresponding materials and methods for the delayed release of active compounds and for the application of coatings which are resistant to gastric juices are known to the person skilled in the art, for example from "Coated Pharmaceutical dosage forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers.

A particularly preferred coating contains polyvinyl alcohol and optionally, further excipients such as xanthan gum and/or talcum.

When the pharmaceutical dosage form is multiparticulate, the particles contain at least a pharmacologically active ingredient having psychotropic action and an EVA polymer, preferably a prolonged release matrix containing the EVA polymer as prolonged release matrix material and optionally additional prolonged release matrix material. Preferably, however, the particles further contain additional pharmaceutical excipients such as antioxidants and plasticizers.

When the pharmaceutical dosage form is multiparticulate, the particles may be e.g. loosely contained in a capsule, or the particles may be incorporated into an outer matrix material. From a macroscopic perspective, the outer matrix material preferably forms a continuous phase in which the particles are embedded as discontinuous phase.

Preferably, the outer matrix material is preferably a homogenous coherent mass, preferably a homogeneous mixture of solid constituents, in which the particles are embedded thereby spatially separating the particles from one another. While it is possible that the surfaces of particles are in contact or at least in very close proximity with one another, the plurality of particles preferably cannot be regarded as a single continuous coherent mass within the pharmaceutical dosage form.

In other words, when the pharmaceutical dosage form is multiparticulate and the particles are contained in an outer matrix material, the pharmaceutical dosage form according to the invention preferably comprises the particles as volume element(s) of a first type in which the pharmacologically active ingredient and the EVA polymer are contained, and the outer matrix material as volume element of a second type differing from the material that forms the particles, preferably containing neither pharmacologically active ingredient nor EVA polymer.

When the pharmaceutical dosage form is multiparticulate and the particles are contained in an outer matrix material, the relative weight ratio of particles to outer matrix material is not particularly limited. Preferably, said relative weight ratio is within the range of 1:1.00±0.75, more preferably 1:1.00±0.50, still more preferably 1:1.00±0.40, yet more preferably 1:1.00±0.30, most preferably 1:1.00±0.20, and in particular 1:1.00±0.10.

Preferably, the content of the outer matrix material is at least 2.5 wt.-%, at least 5 wt.-%, at least 7.5 wt.-% or at least 10 wt.-%; at least 12.5 wt.-%, at least 15 wt.-%, at least 17.5 wt.-% or at least 20 wt.-%; at least 22.5 wt.-%, at least 25 wt.-%, at least 27.5 wt.-% or at least 30 wt.-%; at least 32.5 wt.-%, at least 35 wt.-%, at least 37.5 wt.-% or at least 40 wt.-%; more preferably at least 42.5 wt.-%, at least 45 wt.-%, at least 47.5 wt.-% or at least 50 wt.-%; still more preferably at least 52.5 wt.-%, at least 55 wt.-%, at least 57.5 wt.-% or at least 60 wt.-%; yet more preferably at least 62.5 wt.-%, at least 65 wt.-%, at least 67.5 wt.-% or at least 60 wt.-%; most preferably at least 72.5 wt.-%, at least 75 wt.-%, at least 77.5 wt.-% or at least 70 wt.-%; and in particular at least 82.5 wt.-%, at least 85 wt.-%, at least 87.5 wt.-% or at least 90 wt.-%; based on the total weight of the pharmaceutical dosage form.

Preferably, the content of the outer matrix material is at most 90 wt.-%, at most 87.5 wt.-%, at most 85 wt.-%, or at most 82.5 wt.-%; more preferably at most 80 wt.-%, at most 77.5 wt.-%, at most 75 wt.-% or at most 72.5 wt.-%; still more preferably at most 70 wt.-%, at most 67.5 wt.-%, at most 65 wt.-% or at most 62.5 wt.-%; yet more preferably at most 60 wt.-%, at most 57.5 wt.-%, at most 55 wt.-% or at most 52.5 wt.-%; most preferably at most 50 wt.-%, at most 47.5 wt.-%, at most 45 wt.-% or at most 42.5 wt.-%; and in particular at most 40 wt.-%, at most 37.5 wt.-%, or at most 35 wt.-%; based on the total weight of the pharmaceutical dosage form.

Preferably, the outer matrix material is a mixture, preferably a homogeneous mixture of at least two different constituents, more preferably of at least three different constituents. In a preferred embodiment, all constituents of the outer matrix material are homogeneously distributed in the continuous phase that is formed by the outer matrix material.

Preferably, the outer matrix material is also provided in particulate form, i.e. in the course of the manufacture of the pharmaceutical dosage forms according to the invention, the constituents of the outer matrix material are preferably processed into particles, subsequently mixed with the particles that contain the pharmacologically active ingredient and the EVA polymer, and then compressed into the pharmaceutical dosage forms.

Preferably, the average size of the particles of the outer matrix material is within the range of ±60%, more preferably ±50%, still more preferably ±40%, yet more preferably ±30%, most preferably ±20%, and in particular ±10% of the average size of the particles that contain the pharmacologically active ingredient and the EVA polymer.

The particles of the outer matrix material can be manufactured by conventional methods for the preparation of aggregates and agglomerates from powder mixtures such as granulating and compacting.

In a preferred embodiment, the mixture of all constituents of the outer matrix material is blended and pre-compacted thereby yielding a pre-compacted outer matrix material.

The outer matrix material preferably does not contain any pharmacologically active ingredient.

Preferably, the outer matrix material comprises a filler or a binder. As many fillers can be regarded as binders and vice versa, for the purpose of specification "filler/binder" refers to any excipient that is suitable as filler, binder or both. Thus, the outer matrix material preferably comprises a filler/binder.

Preferred fillers (=filler/binders) are selected from the group consisting of silicium dioxide (e.g. Aerosil®), microcrystalline cellulose (e.g. Avicel®, Elcema®, Emocel®, ExCel®, Vitacell®; cellulose ether (e.g. Natrosol®, Klucel®, Methocel®, Blanose®, Pharmacoat®, Viscontran®); mannitol; dextrines; dextrose; calciumhydrogen phosphate (e.g. Emcompress®); maltodextrine (e.g. Emdex®); lactose (e.g. Fast-Flow Lactose®; Ludipress® Pharmaceutical dosage Formtose®, Zeparox®); polyvinylpyrrolidone (PVP) (e.g. Kollidone®, Polyplasdone®, Polydone®); saccharose (e.g. Nu-Tab®, Sugar Tab®); magnesium salts (e.g. MgCO$_3$, MgO, MgSiO$_3$); starches and pretreated starches (e.g. Prejel®, Primotab® ET, Starch® 1500). Preferred binders are selected from the group consisting of alginates; chitosanes; and any of the fillers mentioned above (=fillers/binders).

Some fillers/binders may also serve other purposes. It is known, for example, that silicium dioxide exhibits excellent function as a glidant. Thus, preferably, the outer matrix material comprises a glidant such as silicium dioxide.

In a preferred embodiment, the content of the filler/binder or mixture of fillers/binders in the outer matrix material is within the range of 50±25 wt.-%, more preferably 50±20 wt.-%, still more preferably 50±15 wt.-%, yet more preferably 50±10 wt.-%, most preferably 50±7.5 wt.-%, and in particular 50±5 wt.-%, based on the total weight of outer matrix material. In another preferred embodiment, the content of the filler/binder or mixture of fillers/binders in the outer matrix material is within the range of 65±25 wt.-%, more preferably 65±20 wt.-%, still more preferably 65±15 wt.-%, yet more preferably 65±10 wt.-%, most preferably 65±7.5 wt.-%, and in particular 65±5 wt.-%, based on the total weight of outer matrix material. In still another preferred embodiment, the content of the filler/binder or mixture of fillers/binders in the outer matrix material is within the range of 80±19 wt.-%, more preferably 80±17.5 wt.-%, still more preferably 80±15 wt.-%, yet more preferably 80±10 wt.-%, most preferably 80±7.5 wt.-%, and in particular 80±5 wt.-%, based on the total weight of outer matrix material. In another preferred embodiment, the content of the filler/binder or mixture of fillers/binders in the outer matrix material is within the range of 90±9 wt.-%, more preferably 90±8 wt.-%, still more preferably 90±7 wt.-%, yet more preferably 90±6 wt.-%, most preferably 90±5 wt.-%, and in particular 90±4 wt.-%, based on the total weight of outer matrix material.

In a preferred embodiment, the content of the filler/binder or mixture of fillers/binders in the pharmaceutical dosage form is within the range of 25±24 wt.-%, more preferably 25±20 wt.-%, still more preferably 25±16 wt.-%, yet more preferably 25±12 wt.-%, most preferably 25±8 wt.-%, and in particular 25±4 wt.-%, based on the total weight of pharmaceutical dosage form. In another preferred embodiment, the content of the filler/binder or mixture of fillers/binders in the pharmaceutical dosage form is within the range of 30±29 wt.-%, more preferably 30±25 wt.-%, still more preferably 30±20 wt.-%, yet more preferably 30±15 wt.-%, most preferably 30±10 wt.-%, and in particular 30±5 wt.-%, based on the total weight of pharmaceutical dosage form. In still another preferred embodiment, the content of the filler/binder or mixture of fillers/binders in the pharmaceutical dosage form is within the range of 35±34 wt.-%, more preferably 35±28 wt.-%, still more preferably 35±22 wt.-%, yet more preferably 35±16 wt.-%, most preferably 35±10 wt.-%, and in particular 35±4 wt.-%, based on the total weight of pharmaceutical dosage form. In another preferred embodiment, the content of the filler/binder or mixture of fillers/binders in the pharmaceutical dosage form is within the range of 40±39 wt.-%, more preferably 40±32 wt.-%, still more preferably 40±25 wt.-%, yet more preferably 40±18 wt.-%, most preferably 40±11 wt.-%, and in particular 40±4 wt.-%, based on the total weight of pharmaceutical dosage form.

Preferably, the filler/binder is contained in the outer matrix material but not in the drug-containing particles of the pharmaceutical dosage form according to the invention.

Preferably, the outer matrix material comprises a diluent or lubricant, preferably selected from the group consisting of calcium stearate; magnesium stearate; glycerol monobehenate (e.g. Compritol®); Myvatex®; Precirol®; Precirol® Ato5; sodium stearylfumarate (e.g. Pruv®); and talcum. Magnesium stearate is particularly preferred. Preferably, the content of the lubricant in the outer matrix material is at most 10.0 wt.-%, more preferably at most 7.5 wt.-%, still more preferably at most 5.0 wt.-%, yet more preferably at most 2.0 wt.-%, even more preferably at most 1.0 wt.-%, and most preferably at most 0.5 wt.-%, based on the total weight of the outer matrix material and based on the total weight of pharmaceutical dosage form.

In particularly preferred embodiment, the outer matrix material comprises a combination of filler/binder and lubricant.

The outer matrix material of the pharmaceutical dosage forms according to the invention may additionally contain other excipients that are conventional in the art, e.g. diluents, binders, granulating aids, colorants, flavor additives, glidants, wet-regulating agents and disintegrants. The skilled person will readily be able to determine appropriate quantities of each of these excipients.

In a preferred embodiment, however, the outer matrix material of the pharmaceutical dosage form according to the invention consists of one or more disintegrants, one or more filler/binder's and one or more lubricants, but does not contain any other constituents.

In a particularly preferred embodiment, the outer matrix material of the pharmaceutical dosage form according to the invention does not contain one or more gel-forming agents and/or a silicone.

As used herein the term "gel-forming agent" is used to refer to a compound that, upon contact with a solvent (e.g. water), absorbs the solvent and swells, thereby forming a viscous or semi-viscous substance. Preferred gel-forming agents are not cross-linked. This substance may moderate pharmacologically active ingredient release from the embedded particles in both aqueous and aqueous alcoholic media. Upon full hydration, a thick viscous solution or dispersion is typically produced that significantly reduces and/or minimizes the amount of free solvent which can contain an amount of solubilized pharmacologically active ingredient, and which can be drawn into a syringe. The gel that is formed may also reduce the overall amount of pharmacologically active ingredient extractable with the solvent by entrapping the pharmacologically active ingredient within a gel structure. Thus the gel-forming agent may play an important role in conferring tamper-resistance to the pharmaceutical dosage forms according to the invention.

Gel-forming agents that preferably are not contained in the outer matrix material include pharmaceutically acceptable polymers, typically hydrophilic polymers, such as hydrogels. Representative examples of gel-forming agent include polyalkylene oxide such as polyethylene oxide, polyvinyl alcohol, hydroxypropylmethyl cellulose, carbomers, poly(uronic) acids and mixtures thereof.

When the pharmaceutical dosage form comprises a prolonged release matrix in which the pharmacologically active ingredient is embedded, preferably, the overall content of the prolonged release matrix, i.e. of the prolonged release matrix material and the optionally present additional prolonged release matrix material, is within the range of from 5 to 95 wt.-%, more preferably 15 to 90 wt.-%, still more preferably 25 to 88 wt.-%, yet more preferably 35 to 86 wt.-%, even more preferably 45 to 84 wt.-%, most preferably 55 to 82 wt.-% and in particular 60 to 80 wt.-%, relative to the total weight of the pharmaceutical dosage form or, when the pharmaceutical dosage form is multiparticulate, based on the total weight of the particles that contain the pharmacologically active ingredient.

In a preferred embodiment, the content of the prolonged release matrix is at least 20 wt.-%, more preferably at least 30 wt.-%, still more preferably at least 40 wt.-%, yet more preferably at least 50 wt.-% and in particular at least 60 wt.-%, either based on the total weight of the pharmaceutical dosage form or, when the pharmaceutical dosage form is multiparticulate, based on the total weight of the particles that contain the pharmacologically active ingredient.

In a preferred embodiment, the overall content of prolonged release matrix is within the range of 30±20 wt.-%, more preferably 30±15 wt.-%, most preferably 30±10 wt.-%, and in particular 30±5 wt.-%, either based on the total weight of the pharmaceutical dosage form or, when the pharmaceutical dosage form is multiparticulate, based on the total weight of the particles that contain the pharmacologically active ingredient.

In another preferred embodiment, the overall content of prolonged release matrix is within the range of 35±20 wt.-%, more preferably 35±15 wt.-%, most preferably 35±10 wt.-%, and in particular 35±5 wt.-%, either based on the total weight of the pharmaceutical dosage form or, when the pharmaceutical dosage form is multiparticulate, based on the total weight of the particles that contain the pharmacologically active ingredient.

In still another preferred embodiment, the overall content of prolonged release matrix is within the range of 40±20 wt.-%, more preferably 40±15 wt.-%, and most preferably 40±10 wt.-%, and in particular 40±5 wt.-%, either based on the total weight of the pharmaceutical dosage form or, when the pharmaceutical dosage form is multiparticulate, based on the total weight of the particles that contain the pharmacologically active ingredient.

In yet another preferred embodiment, the overall content of prolonged release matrix is within the range of 45±20 wt.-%, more preferably 45±15 wt.-%, and most preferably 45±10 wt.-%, and in particular 45±5 wt.-%, either based on the total weight of the pharmaceutical dosage form or, when the pharmaceutical dosage form is multiparticulate, based on the total weight of the particles that contain the pharmacologically active ingredient.

In even another preferred embodiment, the overall content of prolonged release matrix is within the range of 50±20 wt.-%, more preferably 50±15 wt.-%, and most preferably 50±10 wt.-%, and in particular 50±5 wt.-%, either based on the total weight of the pharmaceutical dosage form or, when the pharmaceutical dosage form is multiparticulate, based on the total weight of the particles that contain the pharmacologically active ingredient.

In a further preferred embodiment, the overall content of prolonged release matrix is within the range of 55±20 wt.-%, more preferably 55±15 wt.-%, and most preferably 55±10 wt.-%, and in particular 55±5 wt.-%, either based on the total weight of the pharmaceutical dosage form or, when the pharmaceutical dosage form is multiparticulate, based on the total weight of the particles that contain the pharmacologically active ingredient.

In still a further preferred embodiment, the overall content of prolonged release matrix is within the range of 60±20 wt.-%, more preferably 60±15 wt.-%, and most preferably 60±10 wt.-%, and in particular 60±5 wt.-%, either based on the total weight of the pharmaceutical dosage form or, when the pharmaceutical dosage form is multiparticulate, based on the total weight of the particles that contain the pharmacologically active ingredient.

In yet a further preferred embodiment, the overall content of prolonged release matrix is within the range of 65±20 wt.-%, more preferably 65±15 wt.-%, and most preferably 65±10 wt.-%, and in particular 65±5 wt.-%, either based on the total weight of the pharmaceutical dosage form or, when the pharmaceutical dosage form is multiparticulate, based on the total weight of the particles that contain the pharmacologically active ingredient.

In even a further preferred embodiment, the overall content of prolonged release matrix is within the range of 70±20 wt.-%, more preferably 70±15 wt.-%, and most preferably 70±10 wt.-%, and in particular 70±5 wt.-%, either based on the total weight of the pharmaceutical dosage form or, when the pharmaceutical dosage form is multiparticulate, based on the total weight of the particles that contain the pharmacologically active ingredient.

In another further preferred embodiment, the overall content of prolonged release matrix is within the range of 75±20 wt.-%, more preferably 75±15 wt.-%, and most preferably 75±10 wt.-%, and in particular 75±5 wt.-%, either based on the total weight of the pharmaceutical dosage form or, when the pharmaceutical dosage form is multiparticulate, based on the total weight of the particles that contain the pharmacologically active ingredient.

In still another preferred embodiment, the overall content of prolonged release matrix is within the range of 80±20 wt.-%, more preferably 80±15 wt.-%, and most preferably 80±10 wt.-%, and in particular 80±5 wt.-%, either based on the total weight of the pharmaceutical dosage form or, when the pharmaceutical dosage form is multiparticulate, based on the total weight of the particles that contain the pharmacologically active ingredient.

Preferably, the relative weight ratio of the prolonged release matrix to the pharmacologically active ingredient is within the range of 20:1 to 1:20, more preferably 15:1 to 1:15, still more preferably 10:1 to 1:10, yet more preferably 7:1 to 1:7, most preferably 5:1 to 1:5, and in particular 3:1 to 1:1.

Irrespective of whether the pharmaceutical dosage form is multiparticulate or not, the pharmaceutical dosage form according to the invention comprises a pharmacologically active ingredient having psychotropic action and an EVA polymer.

Particularly preferably, the pharmaceutical dosage form according to the invention comprises a prolonged release matrix containing the EVA polymer as prolonged release matrix material in which the pharmacologically active ingredient is embedded.

Preferably, the EVA polymer is obtainable by polymerizing a mixture containing ethylene and vinyl acetate. Subsequent to the polymerization reaction, the acetate groups of the vinyl acetate contained in the EVA polymer may optionally be subjected to a partial or complete hydrolyzation yielding hydroxy groups.

In a preferred embodiment, the EVA polymer comprises repetition units derived from ethylene and vinyl acetate and/or vinyl alcohol.

According to this embodiment, the EVA polymer may comprise repetition units derived from
(i) ethylene and vinyl acetate; or
(ii) ethylene and vinyl alcohol; or
(ii) ethylene, vinyl acetate and vinyl alcohol.

Embodiments (i) and (iii) are particularly preferred.

Preferably, the relative molar content of the ethylene repetition units within the EVA polymer is greater than the relative molar content of the vinyl acetate repetition units and/or the vinyl alcohol repetition units within the EVA polymer.

Preferably, the EVA polymer contains at least 10 wt.-%, more preferably at least 20 wt.-%, still more preferably at least 25 wt.-%, yet more preferably at least 30 wt.-%, even more preferably at least 35 wt.-%, most preferably at least 40 wt.-% and in particular at least 45 wt.-% of ethylene repetition units, relative to the total weight of the EVA polymer.

Particularly preferably, the EVA polymer contains at least 50 wt.-%, more preferably at least 52 wt.-%, still more preferably at least 54 wt.-%, yet more preferably at least 55 wt.-%, even more preferably at least 56 wt.-%, most preferably at least 57 wt.-% and in particular at least 58 wt.-% of ethylene repetition units, relative to the total weight of the EVA polymer.

In another preferred embodiment, the EVA polymer contains at least 60 wt.-%, more preferably at least 62 wt.-%, still more preferably at least 64 wt.-%, yet more preferably at least 66 wt.-%, even more preferably at least 68 wt.-%, most preferably at least 69 wt.-% and in particular at least 70 wt.-% of ethylene repetition units, relative to the total weight of the EVA polymer.

In still another preferred embodiment, the EVA polymer contains at least 72 wt.-%, more preferably at least 75 wt.-%, still more preferably at least 78 wt.-%, yet more preferably at least 80 wt.-%, even more preferably at least 82 wt.-%, most preferably at least 84 wt.-% and in particular at least 86 wt.-% of ethylene repetition units, relative to the total weight of the EVA polymer.

Preferably, the EVA polymer contains from 30 to 99 wt.-% of ethylene repetition units, relative to the total weight of the EVA polymer.

Particularly preferably, the EVA polymer contains from 50 to 95 wt.-% of ethylene repetition units, relative to the total weight of the EVA polymer.

In a preferred embodiment, the EVA polymer contains 30±25 wt.-%, more preferably 30±20 wt.-%, still more preferably 30±17 wt.-%, yet more preferably 30±13 wt.-%, even more preferably 30±10 wt.-%, most preferably 30±7 wt.-% and in particular 30±5 wt.-% of ethylene repetition units, relative to the total weight of the EVA polymer.

In another preferred embodiment, the EVA polymer contains 40±35 wt.-%, more preferably 40±30 wt.-%, still more preferably 40±25 wt.-%, yet more preferably 40±20 wt.-%, even more preferably 40±15 wt.-%, most preferably 40±10 wt.-% and in particular 40±5 wt.-% of ethylene repetition units, relative to the total weight of the EVA polymer.

In still another preferred embodiment, the EVA polymer contains 50±45 wt.-%, more preferably 50±35 wt.-%, still more preferably 50±25 wt.-%, yet more preferably 50±20 wt.-%, even more preferably 50±15 wt.-%, most preferably 50±10 wt.-% and in particular 50±5 wt.-% of ethylene repetition units, relative to the total weight of the EVA polymer.

In yet another preferred embodiment, the EVA polymer contains 60±35 wt.-%, more preferably 60±30 wt.-%, still more preferably 60±25 wt.-%, yet more preferably 60±20 wt.-%, even more preferably 60±15 wt.-%, most preferably 60±10 wt.-% and in particular 60±5 wt.-% of ethylene repetition units, relative to the total weight of the EVA polymer.

In a further preferred embodiment, the EVA polymer contains 70±25 wt.-%, more preferably 70±20 wt.-%, still more preferably 70±17 wt.-%, yet more preferably 70±13 wt.-%, even more preferably 70±10 wt.-%, most preferably 70±7 wt.-% and in particular 70±5 wt.-% of ethylene repetition units, relative to the total weight of the EVA polymer.

In still a further preferred embodiment, the EVA polymer contains 80±15 wt.-%, more preferably 80±12 wt.-%, still more preferably 80±10 wt.-%, yet more preferably 80±8 wt.-%, even more preferably 80±6 wt.-%, most preferably 80±4 wt.-% and in particular 80±2 wt.-% of ethylene repetition units, relative to the total weight of the EVA polymer.

In yet a further preferred embodiment, the EVA polymer contains 90±15 wt.-%, more preferably 90±12 wt.-%, still more preferably 90±10 wt.-%, yet more preferably 90±8 wt.-%, even more preferably 90±6 wt.-%, most preferably 90±4 wt.-% and in particular 90±2 wt.-% of ethylene repetition units, relative to the total weight of the EVA polymer.

In a particularly preferred embodiment, the EVA polymer contains 60±5 wt.-% of ethylene repetition units, relative to the total weight of the EVA polymer.

Preferably, the molar ratio of the vinyl acetate repetition units to the vinyl alcohol repetition units is within the range of from 1000:1 to 1:1000, more preferably from 900:1 to 1:900, still more preferably from 500:1 to 1:500, yet more preferably from 300:1 to 1:100, even more preferably from 200:1 to 1:10, most preferably from 100:1 to 10:1, and in particular about 100:1.

In a preferred embodiment, the EVA polymer has a melt flow rate at 190° C. and 2.16 kg of at least 1 g/10 min, more preferably at least 2 g/10 min, still more preferably at least 2.5 g/10 min, yet more preferably at least 5 g/10 min, even more preferably at least 10 g/10 min, most preferably at least 20 g/10 min and in particular at least 30 g/10 min measured according to ASTM D1238.

In a preferred embodiment, the EVA polymer has a melt flow rate at 190° C. and 2.16 kg of at least 40 g/10 min, more preferably at least 42 g/10 min, still more preferably at least 44 g/10 min, yet more preferably at least 46 g/10 min, even more preferably at least 48 g/10 min, most preferably at least 49 g/10 min and in particular at least 50 g/10 min measured according to ASTM D1238.

In another preferred embodiment, the EVA polymer has a melt flow rate at 190° C. and 2.16 kg of at least 55 g/10 min, more preferably at least 70 g/10 min, still more preferably at least 85 g/10 min, yet more preferably at least 100 g/10 min, even more preferably at least 115 g/10 min, most preferably at least 130 g/10 min and in particular at least 140 g/10 min measured according to ASTM D1238.

Preferably, the EVA polymer has a melt flow rate at 190° C. and 2.16 kg within the range of from 1 to 160 g/10 min measured according to ASTM D1238.

In a preferred embodiment, the EVA polymer has a melt flow rate at 190° C. and 2.16 kg of 2.5±2 g/10 min, more preferably 2.5±1.5 g/10 min, still more preferably 2.5±1.0 g/10 min, yet more preferably 2.5±0.8 g/10 min, even more preferably 2.5±0.6 g/10 min, most preferably 2.5±0.4 g/10 min and in particular 2.5±0.2 g/10 min measured according to ASTM D1238.

In another preferred embodiment, the EVA polymer has a melt flow rate at 190° C. and 2.16 kg of 3±2 g/10 min, more preferably 3±1.5 g/10 min, still more preferably 3±1.0 g/10 min, yet more preferably 3±0.8 g/10 min, even more preferably 3±0.6 g/10 min, most preferably 3±0.4 g/10 min and in particular 3±0.2 g/10 min measured according to ASTM D1238.

In still another preferred embodiment, the EVA polymer has a melt flow rate at 190° C. and 2.16 kg of 10±16 g/10 min, more preferably 10±14 g/10 min, still more preferably 10±12 g/10 min, yet more preferably 10±10 g/10 min, even more preferably 10±8 g/10 min, most preferably 10±6 g/10 min and in particular 10±4 g/10 min measured according to ASTM D1238.

In yet another preferred embodiment, the EVA polymer has a melt flow rate at 190° C. and 2.16 kg of 20±15 g/10 min, more preferably 20±13 g/10 min, still more preferably 20±11 g/10 min, yet more preferably 20±9 g/10 min, even more preferably 20±7 g/10 min, most preferably 20±5 g/10 min and in particular 20±4 g/10 min measured according to ASTM D1238.

In even another preferred embodiment, the EVA polymer has a melt flow rate at 190° C. and 2.16 kg of 30±25 g/10 min, more preferably 30±20 g/10 min, still more preferably 30±16 g/10 min, yet more preferably 30±13 g/10 min, even more preferably 30±10 g/10 min, most preferably 30±7 g/10 min and in particular 30±5 g/10 min measured according to ASTM D1238.

In a further preferred embodiment, the EVA polymer has a melt flow rate at 190° C. and 2.16 kg of 40±35 g/10 min, more preferably 40±25 g/10 min, still more preferably 40±15 g/10 min, yet more preferably 40±13 g/10 min, even more preferably 40±10 g/10 min, most preferably 40±7 g/10 min and in particular 40±5 g/10 min measured according to ASTM D1238.

In still a further preferred embodiment, the EVA polymer has a melt flow rate at 190° C. and 2.16 kg of 52±20 g/10 min, more preferably 52±16 g/10 min, still more preferably 52±13 g/10 min, yet more preferably 52±10 g/10 min, even more preferably 52±7 g/10 min, most preferably 52±5 g/10 min and in particular 52±2 g/10 min measured according to ASTM D1238.

In yet a further preferred embodiment, the EVA polymer has a melt flow rate at 190° C. and 2.16 kg of 60±35 g/10 min, more preferably 60±25 g/10 min, still more preferably 60±15 g/10 min, yet more preferably 60±13 g/10 min, even more preferably 60±10 g/10 min, most preferably 60±7 g/10 min and in particular 60±5 g/10 min measured according to ASTM D1238.

In even a further preferred embodiment, the EVA polymer has a melt flow rate at 190° C. and 2.16 kg of 80±35 g/10 min, more preferably 80±25 g/10 min, still more preferably 80±15 g/10 min, yet more preferably 80±13 g/10 min, even more preferably 80±10 g/10 min, most preferably 80±7 g/10 min and in particular 80±5 g/10 min measured according to ASTM D1238.

In another preferred embodiment, the EVA polymer has a melt flow rate at 190° C. and 2.16 kg of 100±35 g/10 min, more preferably 100±25 g/10 min, still more preferably 100±15 g/10 min, yet more preferably 100±13 g/10 min, even more preferably 100±10 g/10 min, most preferably 100±7 g/10 min and in particular 100±5 g/10 min measured according to ASTM D1238.

In still another preferred embodiment, the EVA polymer has a melt flow rate at 190° C. and 2.16 kg of 125±35 g/10 min, more preferably 125±25 g/10 min, still more preferably 125±15 g/10 min, yet more preferably 125±13 g/10 min, even more preferably 125±10 g/10 min, most preferably 125±7 g/10 min and in particular 125±5 g/10 min measured according to ASTM D1238.

In yet another preferred embodiment, the EVA polymer has a melt flow rate at 190° C. and 2.16 kg of 150±35 g/10 min, more preferably 150±25 g/10 min, still more preferably 150±15 g/10 min, yet more preferably 150±13 g/10 min, even more preferably 150±10 g/10 min, most preferably 150±7 g/10 min and in particular 150±5 g/10 min measured according to ASTM D1238.

In a particularly preferred embodiment, the EVA polymer has a melt flow rate at 190° C. and 2.16 kg of 52±2 g/10 min measured according to ASTM D1238.

The EVA polymer may comprise a single EVA polymer having a particular melt flow rate, or a mixture (blend) of different EVA polymers, such as two, three, four or five EVA polymers, e.g., EVA polymers of the same chemical nature but different melt flow rates, EVA polymers of different chemical nature but same melt flow rates, or EVA polymers of different chemical nature as well as different melt flow rates.

In a preferred embodiment, the EVA polymer comprises a single EVA polymer having a particular melt flow rate. According to this embodiment, the EVA preferably comprises a single EVA polymer having a melt flow rate at 190° C. and 2.16 kg of 52±2 g/10 min measured according to ASTM D1238 and preferably containing 60±5 wt.-% of ethylene repetition units, relative to the total weight of the EVA polymer.

The EVA polymer preferably has a melting point in the range of 40 to 100° C., determined via differential scanning calorimetry (DSC) in accordance with ASTM D3418.

In a preferred embodiment, the EVA polymer has a melting point of 40±10° C., 47±10° C., 52±10° C., 58±10° C., 65±10° C., 70±10° C., 80±10° C., 90±10° C. or 96±10° C., more preferably 40±5° C., 47±5° C., 52±5° C., 58±5° C., 65±5° C., 70±5° C., 80±5° C., 90±5° C. or 96±5° C., determined via differential scanning calorimetry (DSC) in accordance with ASTM D3418.

The EVA polymer preferably has a freezing point in the range of 20 to 80° C., determined via DSC in accordance with ASTM D3418.

In a preferred embodiment, the EVA polymer has a freezing point of 20±10° C., 27±10° C., 30±10° C., 35±10° C., 40±10° C., 49±10° C., 60±10° C., 70±10° C. or 74±10° C., more preferably 20±5° C., 27±5° C., 30±5° C., 35±5° C., 40±5° C., 49±5° C., 60±5° C., 70±5° C. or 74±° C., determined via DSC in accordance with ASTM D3418.

Particularly preferably, the EVA polymer has a melting point of 47±5° C. and a freezing point of 27±5° C., both determined via DSC in accordance with ASTM D3418

In a preferred embodiment, the EVA polymer is homogeneously distributed in the pharmaceutical dosage form according to the invention.

When the pharmaceutical dosage form is multiparticulate, the EVA polymer is preferably homogeneously distributed in the particles according to the invention that contain the pharmacologically active ingredient. Preferably, the pharmacologically active ingredient and the EVA polymer are intimately homogeneously distributed in the pharmaceutical dosage form and the particles, respectively, so that the pharmaceutical dosage form and the particles, respectively, do not contain any segments where either pharmacologically active ingredient is present in the absence of EVA polymer or where EVA polymer is present in the absence of pharmacologically active ingredient.

When the pharmaceutical dosage form and the particles, respectively, are film coated, the EVA polymer is preferably homogeneously distributed in the core of the pharmaceutical dosage form and the particles, respectively, i.e. the film coating preferably does not contain EVA polymer. Nonetheless, the film coating as such may of course contain one or more polymers, which however, preferably differ from the EVA polymer contained in the core.

EVA polymers that are suitable for use in the pharmaceutical dosage forms according to the invention are commercially available, e.g. from Celanese, for example Ateva® 1081, Ateva® 1070, Ateva® 1075A, Ateva® 1221, Ateva® 11231, Ateva® 1241, Ateva® 1615, Ateva® 1641, Ateva® 1608, Ateva® 1609, Ateva® 1811, Ateva® 1813, Ateva® 1820, Ateva® 1821A, Ateva® 1850A, Ateva® 1880A, Ateva® 1941, Ateva® 2005A, Ateva® 2030, Ateva® 2020, Ateva® 2604A, Ateva® 2810A, Ateva® 2861A, Ateva® 9020, Ateva® 2820A, Ateva® 2821A, Ateva® 9021A, Ateva® 2825A, Ateva® 2830A, Ateva® 2842A, Ateva® 2842AC, Ateva® 2850A, Ateva® 9030, Ateva® 3325A, Ateva® 3325AC, Ateva® 4030AC, VitalDose® EVA; and from DuPont, for example, Elvax® 40W, Elvax® 220W, Elvax® 265, Elvax® 40L-03, Elvax® 660, Elvax® 150, Elvax® 150W, Elvax® 210W, Elvax® 240W, Elvax® 250, Elvax® 260, Elvax® 350, Elvax® 360, Elvax® 410, Elvax® 420, Elvax® 440, Elvax® 450, Elvax® 460, Elvax® 470, Elvax® 550, Elvax® 560, Elvax® 650Q, Elvax® 670, Elvax® 750, Elvax® 760, Elvax® 760Q, Elvax® 770. Preferred polymers are Elvax® 40W, Elvax® 220W, Elvax® 265, Elvax® 40L-03 and Elvax® 660. For details concerning the properties of these products, it can be referred to e.g. the product specification.

The content of the EVA polymer is preferably within the range of from 5.0 to 95 wt.-%, more preferably 7 to 94 wt.-%, still more preferably 9 to 93 wt.-%, yet more preferably 11 to 92 wt.-%, most preferably 13 to 91 wt.-%, and in particular 15 to 90 wt.-%, relative to the total weight of the pharmaceutical dosage form. When the pharmaceutical dosage form is multiparticulate, these percent values preferably are related to the total weight of the particles, not to the total weight of the pharmaceutical dosage form.

In a particularly preferred embodiment, the content of the EVA polymer is within the range of from 20 to 80 wt.-%, more preferably 25 to 78 wt.-%, still more preferably 30 to 76 wt.-%, yet more preferably 35 to 74 wt.-%, most preferably 40 to 72 wt.-% and in particular 45 to 70 wt.-%, relative to the total weight of the pharmaceutical dosage form or, when the pharmaceutical dosage form is multiparticulate, relative to the total weight of the particles that contain the pharmacologically active ingredient.

In a preferred embodiment, the content of the EVA polymer is at least 2 wt.-%, more preferably at least 5 wt.-%, still more preferably at least 10 wt.-%, yet more preferably at least 15 wt.-% and in particular at least 20 wt.-%, relative to the total weight of the pharmaceutical dosage form or, when the pharmaceutical dosage form is multiparticulate, relative to the total weight of the particles that contain the pharmacologically active ingredient.

In another preferred embodiment, the content of the EVA polymer is at least 30 wt.-%, more preferably at least 35 wt.-%, still more preferably at least 40 wt.-%, yet more preferably at least 45 wt.-%, even more preferably at least 50, most preferably at least 55 wt.-% and in particular at least 60 wt.-%, relative to the total weight of the pharmaceutical dosage form or, when the pharmaceutical dosage form is multiparticulate, relative to the total weight of the particles that contain the pharmacologically active ingredient.

In a preferred embodiment, the content of the EVA polymer is 20±15 wt.-%, more preferably 20±12 wt.-%, still more preferably 20±10 wt.-%, yet more preferably 20±8 wt.-%, even more preferably 20±6 wt.-%, most preferably 20±4 wt.-% and in particular 20±2 wt.-%, relative to the total weight of the pharmaceutical dosage form or, when the pharmaceutical dosage form is multiparticulate, relative to the total weight of the particles that contain the pharmacologically active ingredient.

In another preferred embodiment, the content of the EVA polymer is 30±25 wt.-%, more preferably 30±20 wt.-%, still more preferably 30±17 wt.-%, yet more preferably 30±13 wt.-%, even more preferably 30±10 wt.-%, most preferably 30±7 wt.-% and in particular 30±5 wt.-%, relative to the total weight of the pharmaceutical dosage form or, when the pharmaceutical dosage form is multiparticulate, relative to the total weight of the particles that contain the pharmacologically active ingredient.

In still another preferred embodiment, the content of the EVA polymer is 40±35 wt.-%, more preferably 40±30 wt.-%, still more preferably 40±25 wt.-%, yet more preferably 40±20 wt.-%, even more preferably 40±15 wt.-%, most preferably 40±10 wt.-% and in particular 40±5 wt.-%, relative to the total weight of the pharmaceutical dosage form or, when the pharmaceutical dosage form is multiparticulate, relative to the total weight of the particles that contain the pharmacologically active ingredient.

In yet another preferred embodiment, the content of the EVA polymer is 50±45 wt.-%, more preferably 50±35 wt.-%, still more preferably 50±25 wt.-%, yet more preferably 50±20 wt.-%, even more preferably 50±15 wt.-%, most preferably 50±10 wt.-% and in particular 50±5 wt.-%, relative to the total weight of the pharmaceutical dosage form or, when the pharmaceutical dosage form is multiparticulate, relative to the total weight of the particles that contain the pharmacologically active ingredient.

In even another preferred embodiment, the content of the EVA polymer is 55±40 wt.-%, more preferably 55±35 wt.-%, still more preferably 55±25 wt.-%, yet more preferably 55±20 wt.-%, even more preferably 55±15 wt.-%, most preferably 55±10 wt.-% and in particular 55±5 wt.-%, relative to the total weight of the pharmaceutical dosage form or, when the pharmaceutical dosage form is multiparticulate, relative to the total weight of the particles that contain the pharmacologically active ingredient.

In a further preferred embodiment, the content of the EVA polymer is 60±35 wt.-%, more preferably 60±30 wt.-%, still more preferably 60±25 wt.-%, yet more preferably 60±20 wt.-%, even more preferably 60±15 wt.-%, most preferably 60±10 wt.-% and in particular 60±5 wt.-%, relative to the total weight of the pharmaceutical dosage form or, when the pharmaceutical dosage form is multiparticulate, relative to the total weight of the particles that contain the pharmacologically active ingredient.

In still a further preferred embodiment, the content of the EVA polymer is 65±30 wt.-%, more preferably 65±25 wt.-%, still more preferably 65±20 wt.-%, yet more preferably 65±15 wt.-%, even more preferably 65±10 wt.-%, most preferably 65±7 wt.-% and in particular 65±5 wt.-%, relative to the total weight of the pharmaceutical dosage form or, when the pharmaceutical dosage form is multiparticulate, relative to the total weight of the particles that contain the pharmacologically active ingredient.

In yet a further preferred embodiment, the content of the EVA polymer is 70±25 wt.-%, more preferably 70±20 wt.-%, still more preferably 70±17 wt.-%, yet more preferably 70±13 wt.-%, even more preferably 70±10 wt.-%, most preferably 70±7 wt.-% and in particular 70±5 wt.-%, relative to the total weight of the pharmaceutical dosage form or, when the pharmaceutical dosage form is multiparticulate, relative to the total weight of the particles that contain the pharmacologically active ingredient.

In even a further preferred embodiment, the content of the EVA polymer is 80±15 wt.-%, more preferably 80±12 wt.-%, still more preferably 80±10 wt.-%, yet more preferably 80±8 wt.-%, even more preferably 80±6 wt.-%, most preferably 80±4 wt.-% and in particular 80±2 wt.-%, relative to the total weight of the pharmaceutical dosage form or, when the pharmaceutical dosage form is multiparticulate, relative to the total weight of the particles that contain the pharmacologically active ingredient.

When the pharmaceutical dosage form comprises a prolonged release matrix containing the EVA polymer as prolonged release matrix material, the content of the EVA polymer is preferably within the range of from 5 to 100 wt.-%, more preferably 20 to 98 wt.-%, still more preferably 35 to 96 wt.-%, yet more preferably 45 to 95 wt.-%, even more preferably 55 to 94 wt.-%, most preferably 65 to 93 wt.-%, and in particular 75 to 92 wt.-%, relative to the total weight of the prolonged release matrix, i.e. total weight of the prolonged release matrix material and the optionally present additional prolonged release matrix material.

Preferably, the relative weight ratio of the EVA polymer to the pharmacologically active ingredient is within the range of 20:1 to 1:20, more preferably 15:1 to 1:15, still more preferably 10:1 to 1:10, yet more preferably 7:1 to 1:7, most preferably 5:1 to 1:5, and in particular 3:1 to 1:1.

In a preferred embodiment, when the pharmaceutical dosage form according to the invention comprises a prolonged release matrix, the prolonged release matrix in turn comprises an additional prolonged release matrix material besides the prolonged release matrix material, i.e. the EVA polymer. Thus, the additional prolonged release matrix material is to be distinguished from the prolonged release matrix material of the prolonged release matrix of the pharmaceutical dosage form according to the invention.

Preferably, the additional prolonged release matrix material is a polymer selected from the group comprising polyalkylene oxides, acrylic polymers, crosslinked acrylic polymers, mixtures of polyvinyl pyrrolidone and polyvinyl acetate, waxy materials, polyalkylene glycols and natural polysaccharides, such as celluloses, cellulose derivatives and xanthan gum.

The content of the additional prolonged release matrix material is preferably within the range of from 1 to 90 wt.-%, more preferably 2 to 80 wt.-%, still more preferably 3 to 70 wt.-%, yet more preferably 3.5 to 60 wt.-%, even more preferably 4 to 50 wt.-%, most preferably 4.5 to 40 wt.-%, and in particular 5 to 30 wt.-%, relative to the total weight of the prolonged release matrix.

In a preferred embodiment, the content of the additional prolonged release matrix material is at least 2 wt.-%, more preferably at least 5 wt.-%, still more preferably at least 10 wt.-%, yet more preferably at least 15 wt.-% and in particular at least 20 wt.-%, either based on the total weight of the pharmaceutical dosage form or, when the pharmaceutical dosage form is multiparticulate, based on the total weight of the particles that contain the pharmacologically active ingredient.

The overall content of additional prolonged release matrix material is preferably within the range of from 1 to 60 wt.-%, more preferably 2 to 45 wt.-%, still more preferably 3 to 35 wt.-%, yet more preferably 4 to 28 wt.-%, even more preferably 5 to 25 wt.-%, most preferably 5 to 22 wt.-%, and in particular 5 to 20 wt.-%, either based on the total weight of the pharmaceutical dosage form or, when the pharmaceutical dosage form is multiparticulate, based on the total weight of the particles that contain the pharmacologically active ingredient.

In a preferred embodiment, the overall content of additional prolonged release matrix material is within the range of 5±4 wt.-%, more preferably 5±3 wt.-%, most preferably 5±2 wt.-%, and in particular 5±1 wt.-%, either based on the total weight of the pharmaceutical dosage form or, when the pharmaceutical dosage form is multiparticulate, based on the total weight of the particles that contain the pharmacologically active ingredient.

In another preferred embodiment, the overall content of additional prolonged release matrix material is within the range of 7.5±6 wt.-%, more preferably 7.5±4 wt.-%, most preferably 7.5±3 wt.-%, and in particular 7.5±2 wt.-%, either based on the total weight of the pharmaceutical dosage form or, when the pharmaceutical dosage form is multiparticulate, based on the total weight of the particles that contain the pharmacologically active ingredient.

In still another preferred embodiment, the overall content of additional prolonged release matrix material is within the range of 10±8 wt.-%, more preferably 10±6 wt.-%, most preferably 10±4 wt.-%, and in particular 10±2 wt.-%, either based on the total weight of the pharmaceutical dosage form or, when the pharmaceutical dosage form is multiparticulate, based on the total weight of the particles that contain the pharmacologically active ingredient. In yet another preferred embodiment, the overall content of additional prolonged release matrix material is within the range of 15±12 wt.-%, more preferably 15±10 wt.-%, most preferably 15±7 wt.-%, and in particular 15±3 wt.-%, either based on the total weight of the pharmaceutical dosage form or, when the pharmaceutical dosage form is multiparticulate, based on the total weight of the particles that contain the pharmacologically active ingredient.

In even another preferred embodiment, the overall content of additional prolonged release matrix material is within the range of 20±16 wt.-%, more preferably 20±12 wt.-%, most preferably 20±8 wt.-%, and in particular 20±4 wt.-%, either based on the total weight of the pharmaceutical dosage form or, when the pharmaceutical dosage form is multiparticulate, based on the total weight of the particles that contain the pharmacologically active ingredient.

In a further preferred embodiment, the overall content of additional prolonged release matrix material is within the range of 25±20 wt.-%, more preferably 25±15 wt.-%, most preferably 25±10 wt.-%, and in particular 25±5 wt.-%, either based on the total weight of the pharmaceutical dosage form or, when the pharmaceutical dosage form is multiparticulate, based on the total weight of the particles that contain the pharmacologically active ingredient.

In still a further preferred embodiment, the overall content of additional prolonged release matrix material is within the range of 30±20 wt.-%, more preferably 30±15 wt.-%, most preferably 30±10 wt.-%, and in particular 30±5 wt.-%, either based on the total weight of the pharmaceutical dosage form or, when the pharmaceutical dosage form is multiparticulate, based on the total weight of the particles that contain the pharmacologically active ingredient.

In yet a further preferred embodiment, the overall content of additional prolonged release matrix material is within the range of 35±20 wt.-%, more preferably 35±15 wt.-%, most preferably 35±10 wt.-%, and in particular 35±5 wt.-%, either based on the total weight of the pharmaceutical dosage form or, when the pharmaceutical dosage form is multiparticulate, based on the total weight of the particles that contain the pharmacologically active ingredient.

In even a further preferred embodiment, the overall content of additional prolonged release matrix material is within the range of 40±20 wt.-%, more preferably 40±15 wt.-%, and most preferably 40±10 wt.-%, and in particular 40±5 wt.-%, either based on the total weight of the pharmaceutical dosage form or, when the pharmaceutical dosage form is multiparticulate, based on the total weight of the particles that contain the pharmacologically active ingredient.

In another preferred embodiment, the overall content of additional prolonged release matrix material is within the range of 45±20 wt.-%, more preferably 45±15 wt.-%, and most preferably 45±10 wt.-%, and in particular 45±5 wt.-%, either based on the total weight of the pharmaceutical dosage form or, when the pharmaceutical dosage form is multiparticulate, based on the total weight of the particles that contain the pharmacologically active ingredient.

In still another preferred embodiment, the overall content of additional prolonged release matrix material is within the range of 50±20 wt.-%, more preferably 50±15 wt.-%, and most preferably 50±10 wt.-%, and in particular 50±5 wt.-%, either based on the total weight of the pharmaceutical dosage form or, when the pharmaceutical dosage form is multiparticulate, based on the total weight of the particles that contain the pharmacologically active ingredient.

Preferably, the relative weight ratio of the additional prolonged release matrix material to the pharmacologically active ingredient is within the range of 20:1 to 1:20, more preferably 10:1 to 1:15, still more preferably 7:1 to 1:10, yet more preferably 5:1 to 1:7, most preferably 1:1 to 1:5, and in particular 1:2 to 1:5.

Preferably, the relative weight ratio of the additional prolonged release matrix material to the prolonged release matrix material of the prolonged release matrix is within the range of 20:1 to 1:20, more preferably 10:1 to 1:18, still more preferably 7:1 to 1:16, yet more preferably 5:1 to 1:14, most preferably 1:1 to 1:12, and in particular 1:5 to 1:10.

In a preferred embodiment, the pharmaceutical dosage form according to the invention comprises a prolonged release matrix which in turn comprises
(i) an EVA polymer as a prolonged release matrix material, wherein the EVA polymer comprises a single EVA polymer having a melt flow rate at 190° C. and 2.16 kg of 52±2 g/10 min measured according to ASTM D1238 and preferably containing 60±5 wt.-% of ethylene repetition units, relative to the total weight of the EVA polymer; and
(ii) an additional prolonged release matrix material which is preferably a polymer selected from the group consisting of polyalkylene oxides, crosslinked acrylic polymers and matrices based on polyvinyl acetate and polyvinyl pyrrolidone;
wherein
(iii) the relative weight content of the prolonged release matrix material is preferably greater than the relative weight content of the additional prolonged release matrix material.

In a preferred embodiment, the additional prolonged release matrix material is a polyalkylene oxide, preferably a polyethylene oxide, particularly preferably having a weight average molecular weight of at least 500,000 g/mol.

When the additional prolonged release matrix material of the prolonged release matrix comprises a polyalkylene oxide, it preferably does not additionally comprise any other additional prolonged release matrix material.

When the pharmaceutical dosage form or, when the pharmaceutical dosage form is multiparticulate, the particles is/are film coated, the polyalkylene oxide is preferably homogeneously distributed within the pharmaceutical dosage form or, when the pharmaceutical dosage form is multiparticulate, the particles, i.e. the film coating preferably does not contain polyalkylene oxide. Nonetheless, the film coating as such may of course contain one or more polymers, which however, preferably differ from the polyalkylene oxide contained in the pharmaceutical dosage form or, when the pharmaceutical dosage form is multiparticulate, the particles.

Preferably, the polyalkylene oxide is selected from polymethylene oxide, polyethylene oxide and polypropylene oxide, or copolymers or mixtures thereof.

Preferably, the polyalkylene oxide has a weight average molecular weight ($M_W$), preferably also a viscosity average molecular weight ($M_n$) of more than 200,000 g/mol or at least 500,000 g/mol, preferably at least 1,000,000 g/mol or at least 2,500,000 g/mol, more preferably in the range of about 1,000,000 g/mol to about 15,000,000 g/mol, and most preferably in the range of about 5,000,000 g/mol to about 10,000,000 g/mol. Suitable methods to determine $M_W$ and $M_n$ are known to a person skilled in the art. $M_n$ is preferably determined by rheological measurements, whereas $M_W$ can be determined by gel permeation chromatography (GPC).

Preferably, the molecular weight dispersity $M_W/M_n$ of the polyalkylene oxide is within the range of 2.5±2.0, more preferably 2.5±1.5, still more preferably 2.5±1.0, yet more preferably 2.5±0.8, most preferably 2.5±0.6, and in particular 2.5±0.4.

The polyalkylene oxide preferably has a viscosity at 25° C. of 30 to 17,600 mPa·s, more preferably 55 to 17,600 mPa·s, still more preferably 600 to 17,600 mPa·s, yet more preferably 4,500 to 17,600 mPa·s, even more preferably 4,500 to 12,000 mPa·s, most preferably 5,000 to 10,500 mPa·s and in particular 5,500 to 7,500 mPa·s or 7,500 to 10,000 mPa·s, measured in a 1 wt.-% aqueous solution.

The polyalkylene oxide may comprise a single polyalkylene oxide having a particular average molecular weight, or a mixture (blend) of different polymers, such as two, three, four or five polymers, e.g., polymers of the same chemical nature but different average molecular weight, polymers of different chemical nature but same average molecular weight, or polymers of different chemical nature as well as different molecular weight.

For the purpose of specification, a polyalkylene glycol has a molecular weight of up to 20,000 g/mol whereas a polyalkylene oxide has a molecular weight of more than 20,000 g/mol. Preferably, the weight average over all molecular weights of all polyalkylene oxides that are contained in the pharmaceutical dosage form is more than 200,000 g/mol. Thus, polyalkylene glycols, if any, are preferably not taken into consideration when determining the weight average molecular weight of polyalkylene oxide.

In a particularly preferred embodiment, the additional prolonged release matrix material is a polyalkylene oxide, more preferably a polyethylene oxide, having a weight average molecular weight ($M_W$), preferably also a viscosity average molecular weight ($M_n$) in the range of about 5,000,000 g/mol to about 10,000,000 g/mol.

The overall content of polyalkylene oxide is preferably within the range of from 1 to 60 wt.-%, more preferably 3 to 45 wt.-%, still more preferably 5 to 35 wt.-%, yet more preferably 7 to 28 wt.-%, even more preferably 8 to 25 wt.-%, most preferably 9 to 22 wt.-%, and in particular 10 to 20 wt.-%, either based on the total weight of the pharmaceutical dosage form or, when the pharmaceutical dosage form is multiparticulate, based on the total weight of the particles that contain the pharmacologically active ingredient.

In a preferred embodiment, the overall content of polyalkylene oxide is within the range of 15±12 wt.-%, more preferably 15±10 wt.-%, most preferably 15±7 wt.-%, and in particular 15±3 wt.-%, either based on the total weight of the pharmaceutical dosage form or, when the pharmaceutical dosage form is multiparticulate, based on the total weight of the particles that contain the pharmacologically active ingredient.

In a preferred embodiment, the additional prolonged release matrix material is a mixture of polyvinyl pyrrolidone and polyvinyl acetate.

When the additional prolonged release matrix material of the prolonged release matrix comprises a mixture of polyvinyl pyrrolidone and polyvinyl acetate, it preferably does not additionally comprise any other additional prolonged release matrix material.

When the pharmaceutical dosage form or, when the pharmaceutical dosage form is multiparticulate, the particles is/are film coated, the mixture of polyvinyl pyrrolidone and polyvinyl acetate is preferably homogeneously distributed within the pharmaceutical dosage form or, when the pharmaceutical dosage form is multiparticulate, the particles, i.e. the film coating preferably does not contain any mixture of polyvinyl pyrrolidone and polyvinyl acetate. Nonetheless, the film coating as such may of course contain one or more polymers, which however, preferably differ from the mixture of polyvinyl pyrrolidone and polyvinyl acetate contained in the pharmaceutical dosage form or, when the pharmaceutical dosage form is multiparticulate, the particles.

Preferably, the mixture of polyvinyl pyrrolidone and polyvinyl acetate contains 10 to 30 wt.-% polyvinyl pyrrolidone and 70 to 90 wt.-% of polyvinyl acetate, more preferably 18 to 21 wt.-% polyvinyl pyrrolidone and 75 to 85 wt.-% of polyvinyl acetate and most preferably 19 wt.-% polyvinyl pyrrolidone and 80 wt.-% of polyvinyl acetate.

The weight ratio between polyvinyl acetate and polyvinyl pyrrolidone preferably is in the range from 20:1 to 1:20, more preferably 16:1 to 1:10, still more preferably 13:1 to 1:5, yet more preferably 10:1 to 1:2, even more preferably 7:1 to 1:1, most preferably 5:1 to 2:1 and in particular 4.5:1 to 3.5:1.

Preferably, the polyvinyl acetate has a weight average molecular weight ($M_W$) of 450,000±100,000 g/mol, more preferably 450,000±80,000 g/mol, still more preferably 450,000±50,000 g/mol, yet more preferably 450,000±10,000 g/mol, even more preferably 450,000±1,000 g/mol, most preferably 450,000±500 g/mol and in particular 450,000±100 g/mol. $M_W$ can be determined by gel permeation chromatography (GPC).

Preferably, the polyvinyl pyrrolidone has a weight average molecular weight ($M_W$) of 50,000±10,000 g/mol, more preferably 50,000±8,000 g/mol, still more preferably 50,000±5,000 g/mol, yet more preferably 50,000±1,000 g/mol, even more preferably 50,000±800 g/mol, most preferably 50,000±500 g/mol and in particular 50,000±100 g/mol.

The weight average molecular weight ($M_W$) of the mixture of polyvinyl pyrrolidone and polyvinyl acetate can be expressed as K-value according to the method described in the USP and Ph. Eur. monographs "Povidone", measured in a 1% solution in tetrahydrofurane, wherein the K-value preferably is in the range of from 40 to 80, more preferably 45 to 78, still more preferably 50 to 75, most preferably 55 to 70 and in particular 60 to 65.

Preferably, the glass transition temperature ($T_g$) of the mixture of polyvinyl pyrrolidone and polyvinyl acetate is in the range of 35±10° C., more preferably 35±6° C. and most preferably 35±3° C.

In a particularly preferred embodiment, the additional prolonged release matrix material is a mixture of polyvinyl pyrrolidone and polyvinyl acetate, wherein said mixture has a K-value in the range of from 60 to 65, measured in a 1% solution in tetrahydrofurane according to the method described in the USP and Ph. Eur. monographs "Povidone" and/or wherein the weight ratio between polyvinyl acetate and polyvinyl pyrrolidone is in the range of 4.5:1 to 3.5:1.

The overall content of the mixture of polyvinyl pyrrolidone and polyvinyl acetate is preferably within the range of from 1.0 to 60 wt.-%, more preferably 2.0 to 50 wt.-%, still more preferably 3.0 to 40 wt.-%, yet more preferably 3.5 to 30 wt.-%, even more preferably 4.0 to 25 wt.-%, most preferably 4.5 to 20 wt.-%, and in particular 5 to 15 wt.-%, either based on the total weight of the pharmaceutical dosage form or, when the pharmaceutical dosage form is multiparticulate, based on the total weight of the particles that contain the pharmacologically active ingredient.

In a preferred embodiment, the overall content of the mixture of polyvinyl pyrrolidone and polyvinyl acetate is within the range of 10±8 wt.-%, more preferably 10±6 wt.-%, most preferably 10±4 wt.-%, and in particular 10±2 wt.-%, either based on the total weight of the pharmaceutical dosage form or, when the pharmaceutical dosage form is multiparticulate, based on the total weight of the particles that contain the pharmacologically active ingredient.

Mixtures of polyvinyl pyrrolidone and polyvinyl acetate that are suitable for use in the pharmaceutical dosage forms according to the invention are commercially available, e.g. from BASF, such as Kollidon® SR. For details concerning the properties of this product, it can be referred to e.g. the product specification.

In another preferred embodiment, the additional prolonged release matrix material is an acrylic polymer.

When the additional prolonged release matrix material of the prolonged release matrix comprises an acrylic polymer, it preferably does not additionally comprise any other additional prolonged release matrix material.

When the pharmaceutical dosage form or, when the pharmaceutical dosage form is multiparticulate, the particles is/are film coated, the acrylic polymer is preferably homogeneously distributed within the pharmaceutical dosage form or, when the pharmaceutical dosage form is multiparticulate, the particles, i.e. the film coating preferably does not contain acrylic polymer. Nonetheless, the film coating as such may of course contain one or more polymers, which however, preferably differ from the acrylic polymer contained in the pharmaceutical dosage form or, when the pharmaceutical dosage form is multiparticulate, the particles.

Preferably, the acrylic polymer has a weight average molecular weight within the range of from 100,000 g/mol to 2,000,000 g/mol. In a preferred embodiment, the acrylic polymer has a weight average molecular weight ($M_W$) or viscosity average molecular weight ($M_\eta$) of at least 150,000 or at least 200,000 g/mol, preferably at least 250,000 g/mol or at least 300,000 g/mol, more preferably in the range of about 300,000 g/mol to about 2,000,000 g/mol, and most preferably in the range of about 300,000 g/mol to about 1,000,000 g/mol. Suitable methods to determine $M_W$ and $M_\eta$ are known to a person skilled in the art. $M_\eta$ is preferably determined by rheological measurements, whereas $M_W$ can be determined by gel permeation chromatography (GPC).

The acrylic polymer can be a nonionic acrylic polymer or an ionic acrylic polymer. For the purpose of specification, "nonionic polymer" refers to a polymer not containing more than 1 mole.-% ionic, i.e. anionic or cationic, monomer units, preferably containing no ionic monomer units at all.

In a preferred embodiment, the additional prolonged release matrix material is an ionic acrylic polymer.

Preferred ionic acrylic polymers are anionic acrylic polymers. Preferred anionic acrylic polymers include but are not limited to homopolymers or copolymers of one or two different $C_{1-4}$-alkyl(meth)acrylate monomers and copolymerizable anionic monomers such as acrylic acid.

For the purpose of the specification, "(meth)acryl" refers to acryl as well as methacryl.

In a preferred embodiment, the additional prolonged release matrix material is an anionic acrylic polymer, preferably polyacrylic acid. According to this embodiment, the polyacrylic acid preferably has a viscosity within the range of 2,000 to 20,000 mPa·s, more preferably 3,000 to 18,000 mPa·s, still more preferably 3,500 to 16,000 mPa·s, yet more preferably 3,600 to 14,000 mPa·s, even more preferably 3,700 to 13,000 mPa·s, most preferably 3,800 to 12,000, and in particular 4,000 to 11,000 mPa·s, measured with a Brookfield RVT, 20 rpm, spindle no. 5 at 25° C. and 0.5 wt.-% neutralized to pH 7.3-7.8.

The acrylic polymer, preferably the anionic acrylic polymer, more preferably the polyacrylic acid polymer can optionally be crosslinked. Preferred crosslinking agents include allyl pentaerythritol, allyl sucrose, ethylene glycol di(methacrylate), methylenebisacrylamide and divinyl benzene.

In a particularly preferred embodiment, the anionic acrylic polymer is a polyacrylic acid polymer which is crosslinked, preferably with ally pentaerythritol, and has a viscosity of 4,000 to 11,000 mPa·s, measured with a Brookfield RVT, 20 rpm, spindle no. 5 at 25° C. and 0.5 wt.-% neutralized to pH 7.3-7.8.

Preferably, the overall content of anionic acrylic polymer, preferably polyacrylic acid, more preferably crosslinked polyacrylic acid, is within the range of from 1.0 to 60 wt.-%, more preferably 2.0 to 50 wt.-%, still more preferably 3.0 to 40 wt.-%, yet more preferably 3.5 to 30 wt.-%, even more preferably 4.0 to 20 wt.-%, most preferably 4.5 to 15 wt.-%, and in particular 5.0 to 12 wt.-%, either based on the total weight of the pharmaceutical dosage form or, when the pharmaceutical dosage form is multiparticulate, based on the total weight of the particles that contain the pharmacologically active ingredient.

Polyacrylic acid polymers that are suitable for use in the pharmaceutical dosage forms according to the invention are commercially available, e.g. from Lubrizol, such as Carbopol® 71G, Carbopol® 971P, Carbopol® 981 and Carbopol® 941. For details concerning the properties of these products, it can be referred to e.g. the product specification.

Other preferred anionic acrylic polymers are ternary copolymers of methyl acrylate, methyl methacrylate and methacrylic acid. Preferably, the anionic acrylic polymer has a weight average molecular weight within the range of 280,000±250,000 g/mol, more preferably 280,000±200,000 g/mol, still more preferably 280,000±180,000 g/mol, yet more preferably 280,000±160,000 g/mol, even more preferably 280,000±140,000 g/mol, most preferably 280,000±120,000 g/mol, and in particular 280,000±100,000 g/mol.

Further preferred ionic acrylic polymers are cationic acrylic polymers. Preferred cationic acrylic polymers include but are not limited to copolymers of one or two different $C_{1-4}$-alkyl(meth)acrylate monomers and copolymerizable cationic monomers such as trimethylammonioethyl methacrylate chloride. Preferred representatives are ternary copolymers of ethyl acrylate, methyl methacrylate and a low content of methacrylic acid ester with quaternary ammonium groups, preferably trimethylammonioethyl methacrylate chloride. Preferably, the cationic acrylic polymer has a weight average molecular weight within the range of 32,000±30,000 g/mol, more preferably 32,000±27,000 g/mol, still more preferably 32,000±23,000 g/mol, yet more preferably 32,000±20,000 g/mol, even more preferably 32,000±17,000 g/mol, most preferably 32,000±13,000 g/mol, and in particular 32,000±10,000 g/mol.

In another preferred embodiment, the additional prolonged release matrix material is a nonionic acrylic polymer.

Nonionic acrylic polymers that are suitable for use in the pharmaceutical dosage forms according to the invention are commercially available, e.g. from Evonik. For example, Eudragit® NE30D, Eudragit® NE40D and Eudragit® NM30D, which are provided as aqueous dispersions of poly(ethyl acrylate-co-methyl methacrylate) 2:1, may be used in the pharmaceutical dosage form according to the invention. For details concerning the properties of these products, it can be referred to e.g. the product specification.

In another preferred embodiment, the additional prolonged release matrix material is a waxy material.

Preferably, the waxy material is selected from the group consisting of
- glycerides, especially monoglycerides, diglycerides, triglycerides,
- esters of fatty acids with fatty alcohols, and
- paraffins.

When the additional prolonged release matrix material of the prolonged release matrix comprises a waxy material, it preferably does not additionally comprise any other additional prolonged release matrix material.

As used herein a "waxy material" refers to a material which melts into liquid form having low viscosity upon heating and sets again to a solid state upon cooling. Preferably, the waxy material has a melting point of at least 30° C., more preferably at least 35° C., still more preferably at least 40° C., yet more preferably at least 45° C., even more preferably at least 50° C., most preferably at least 55° C., and in particular at least 60° C.

When the waxy material is or comprises a monoglyceride, diglyceride, triglyceride or a mixture thereof, it is preferably a mono-, di- or triester of glycerol and carboxylic acids, whereas the carboxylic acid is preferably selected from the group consisting of fatty acids, hydroxy fatty acids and aromatic acids.

Preferred glycerides of fatty acids include monoglycerides, diglycerides, triglycerides, and mixtures thereof; preferably of $C_6$ to $C_{22}$ fatty acids. Especially preferred are partial glycerides of the $C_{16}$ to $C_{22}$ fatty acids such as glycerol behenat, glycerol palmitostearate, glycerol monostearate, glycerol trimyristate and glycerol distearate.

The term "fatty acid" is well acknowledged in the art and includes for example unsaturated representatives such as myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid; as well as saturated representatives such as caprylic acid, capric acid, lauric acid, myristic acid, palmitic acid, stearic acid, arachidic acid, behenic acid, lignoceric acid, and cerotic acid.

The term "hydroxy fatty acid" is also well acknowledged in the art and includes for example 2-hydroxyhexanoic acid, 2-hydroxyoctanoic acid, 2-hydroxydecanoic acid, 2-hydroxy-dodecanoic acid, β-hydroxylauric acid, 2-hydroxytetradecanoic acid, β-hydroxymyristic acid, 15-hydroxypentadecanoic acid, 16-hydroxyhexadecanoic acid, β-hydroxypalmitic acid, 12-hydroxyoctadecanoic acid, α-hydroxystearic acid, and α-hydroxyarachidic acid.

The fatty acids and the hydroxy fatty acids are preferably saturated.

When the waxy material is or comprises a diglyceride or a triglyceride, the fatty acids, hydroxy fatty acids and aromatic acids, respectively, may be identical or different.

According to this embodiment of the invention, the waxy material is preferably a hard fat (adeps solidus) in accordance with Ph. Eur.

Preferably, the waxy material is a monoglyceride, diglyceride, triglyceride or a mixture thereof, selected from the group consisting of hydrogenated soybean oil, hydrogenated palm oil, hydrogenated castor oil, hydrogenated cottonseed oil, and mixtures thereof.

When the waxy material is or comprises an ester of a fatty acid with a fatty alcohol, the fatty acid is preferably a saturated fatty acid. Preferred examples of fatty acids are already mentioned above in connection with the glycerides. The fatty alcohol is preferably derived from a fatty acid and preferably also saturated.

Preferred representatives of esters of fatty acids with fatty alcohols include but are not limited to natural waxes such as beeswax, carnaubawax, cetyl palmitate, oleyl oleate, spermaceti (cetaceum), candelilla wax, ouricury wax, sugarcane wax, and retamo wax.

When the waxy material is or comprises a paraffin, the paraffin is preferably a hard paraffin (paraffinum solidum, ceresin, zeresin) in accordance with Ph. Eur.

The waxy material may comprise a single waxy material, or a mixture (blend) of different waxy materials, such as two, three, four or five waxy materials, each of which preferably being selected from the group consisting of glycerides, especially monoglycerides, diglycerides, triglycerides; esters of fatty acids with fatty alcohols; and paraffins.

Waxy materials that are suitable for use in the pharmaceutical dosage forms according to the invention are commercially available, e.g. Cera alba, Cera flava, Kolliwax™ HCO, Dynasan® 118, Compritol® 888 ATO, Precirol® ATO 5, Gelucire® 44/14. For details concerning the properties of these products, it can be referred to e.g. the product specification.

Preferred polyalkylene glycols include but are not limited to polymethylene oxide, polyethylene oxide, polypropylene oxide, and the copolymers and mixtures thereof. For the purpose of the specification, a polyalkylene glycol has a molecular weight of up to 20,000 g/mol whereas a polyalkylene oxide has a molecular weight of more than 20,000 g/mol.

In a preferred embodiment, the polyalkylene glycol has a weight average molecular weight ($M_W$) or viscosity average molecular weight ($M_\eta$) in the range of about 1,000 g/mol to about 18000 g/mol, and most preferably in the range of about 5,000 g/mol to about 8,000 g/mol. Suitable methods to determine $M_W$ and $M_\eta$ are known to a person skilled in the art. $M_\eta$ is preferably determined by rheological measurements, whereas $M_W$ can be determined by gel permeation chromatography (GPC).

Preferred celluloses and cellulose derivatives include but are not limited to microcrystalline cellulose, cellulose esters and cellulose ethers.

Preferred cellulose ethers include nonionic cellulose ethers such as methylcellulose, ethylcellulose, propylcellulose, hydroxymethylcellulose, hydroxyethylcellulose, hydroxypropylcellulose, and hydroxypropylmethylcellulose; as well as ionic cellulose ethers, i.e. cationic cellulose ethers or anionic cellulose ethers such as carboxymethyl cellulose.

In view of their good solubility in aqueous ethanol, however, ethylcellulose and propylcellulose are preferably only contained in comparatively low amounts (preferably at most 1.0 wt.-%) or not contained at all in the pharmaceutical dosage form according to the invention.

Preferred xanthan gums include but are not limited to Grindsted® Xanthan 80 Pharma available from Danisco and CEROGA Xanthan Gum Type 602 available from Roeper.

Suitable xanthan gums which are commercially available include XANTURAL® 75, XANTURAL® 180 and XANTURAL® 11K from CP Kelco; VANZAN® NF, VANZAN® NF-F, VANZAN® NF-C from Vanderbilt Minerals; Haixan® PM80, Haixan® PM200, Haixan® PM40 from Zibo Hailan Chemical Co.; Xanthan Gum Pharmaceutical Grade PHARM200 from ICD Biochemistry Co. and Xanthan Gum from Jungbunzlauer.

Alternatively or additionally, the additional prolonged release matrix material may comprise one or more polymers, preferably selected from the group consisting of polyethylene, polypropylene, polyvinyl chloride, polycarbonate, polystyrene, polyvinylpyrrolidone, poly(alk)acrylate, poly (hydroxy fatty acids), such as for example poly(3-hydroxybutyrate-co-3-hydroxyvalerate) (Biopol®), poly(hydroxyvaleric acid), polycaprolactone, polyvinyl alcohol, polyesteramide, polyethylene succinate, polylactone, polyglycolide, polyurethane, polyamide, polylactide, polyacetal (for example polysaccharides optionally with modified side chains), polylactide/glycolide, polylactone, polyglycolide, polyorthoester, polyanhydride, block polymers of polyethylene glycol and polybutylene terephthalate (Polyactive®), polyanhydride (Polifeprosan), copolymers thereof, block-copolymers thereof (e.g., Poloxamer®), and mixtures of at least two of the stated polymers, or other polymers with the above characteristics.

The pharmaceutical dosage form or, when it is multiparticulate, the particles according to the invention which contain the pharmacologically active ingredient may contain additional pharmaceutical excipients conventionally contained in pharmaceutical dosage forms in conventional amounts, such as antioxidants, preservatives, lubricants, plasticizer, fillers, binders, and the like.

The skilled person will readily be able to determine appropriate further excipients as well as the quantities of each of these excipients. Specific examples of pharmaceutically acceptable carriers and excipients are described in the Handbook of Pharmaceutical Excipients, American Pharmaceutical Association (1986).

In a preferred embodiment, the pharmaceutical dosage form or, when it is multiparticulate, the particles according to the invention which contain the pharmacologically active ingredient do not contain a disintegrant. According to this embodiment, the pharmaceutical dosage form or, when it is multiparticulate, the particles according to the invention which contain the pharmacologically active ingredient preferably do not contain sodium starch glycolate.

Preferably, the pharmaceutical dosage form or, when it is multiparticulate, the particles according to the invention which contain the pharmacologically active ingredient further comprise an antioxidant. Suitable antioxidants include ascorbic acid, butylated hydroxyanisole (BHA), butylated hydroxytoluene (BHT), salts of ascorbic acid, monothioglycerol, phosphorous acid, vitamin C, vitamin E and the derivatives thereof, coniferyl benzoate, nordihydroguajaretic acid, gallus acid esters, sodium bisulfite, particularly preferably butylhydroxytoluene or butylhydroxyanisole and α-tocopherol. The antioxidant is preferably present in quantities of 0.01 wt.-% to 10 wt.-%, more preferably of 0.03 wt.-% to 5 wt.-%, most preferably of 0.05 wt.-% to 2.5 wt.-%, based on the total weight of the pharmaceutical dosage form and the particles, respectively.

In a preferred embodiment, the pharmaceutical dosage form or, when it is multiparticulate, the particles according to the invention which contain the pharmacologically active ingredient further comprise an acid, preferably citric acid. The amount of acid is preferably in the range of 0.01 wt.-% to about 20 wt.-%, more preferably in the range of 0.02 wt.-% to about 10 wt.-%, and still more preferably in the range of 0.05 wt.-% to about 5 wt.-%, and most preferably in the range of 0.1 wt.-% to about 1.0 wt.-%, based on the total weight of the pharmaceutical dosage form and the particles, respectively.

In a preferred embodiment, the pharmaceutical dosage form or, when it is multiparticulate, the particles according to the invention which contain the pharmacologically active ingredient contain at least one lubricant. In another preferred embodiment, the pharmaceutical dosage form or, when it is multiparticulate, the particles according to the invention which contain the pharmacologically active ingredient contain no lubricant.

Especially preferred lubricants are selected from
magnesium stearate and stearic acid;
polyoxyethylene glycerol fatty acid esters, such as mixtures of mono-, di- and triesters of glycerol and di- and monoesters of macrogols having molecular weights within the range of from 200 to 4000 g/mol, e.g., macrogolglycerolcaprylocaprate, macrogolglycerollaurate, macrogolglycerolococoate, macrogolglycerollinoleate, macrogol-20-glycerolmonostearate, macrogol-6-glycerolcaprylocaprate, macrogolglycerololeate; macrogolglycerolstearate, macrogolglycerolhydroxystearate, and macrogolglycerolrizinoleate;
polyglycolyzed glycerides, such as the one known and commercially available under the trade name "Labrasol";
fatty alcohols that may be linear or branched, such as cetylalcohol, stearylalcohol, cetylstearyl alcohol, 2-octyldodecane-1-ol and 2-hexyldecane-1-ol; and
polyethylene glycols having a molecular weight between 10.000 and 60.000 g/mol.

Preferably, the amount of the lubricant ranges from 0.01 wt.-% to about 10 wt.-%, more preferably in the range of 0.05 wt.-% to about 7.5 wt.-%, most preferably in the range of 0.1 wt.-% to about 5 wt.-%, and in particular in the range of 0.1 wt.-% to about 1 wt.-%, based on the total weight of the pharmaceutical dosage form and the particles, respectively.

Preferably, the pharmaceutical dosage form or, when it is multiparticulate, the particles according to the invention which contain the pharmacologically active ingredient further comprise a plasticizer. The plasticizer improves the processability of the prolonged release matrix material and additional prolonged release matrix material, respectively. A preferred plasticizer is polyalkylene glycol, like polyethylene glycol, triacetin, fatty acids, fatty acid esters, waxes and/or microcrystalline waxes. Particularly preferred plasticizers are polyethylene glycols, such as PEG 6000.

Preferably, the content of the plasticizer is within the range of from 0.5 to 30 wt.-%, more preferably 1.0 to 25 wt.-%, still more preferably 2.5 wt.-% to 22.5 wt.-%, yet more preferably 5.0 wt.-% to 20 wt.-%, most preferably 6 to 20 wt.-% and in particular 7 wt.-% to 17.5 wt.-%, based on the total weight of the pharmaceutical dosage form and the particles, respectively.

Plasticizers can sometimes act as a lubricant, and lubricants can sometimes act as a plasticizer.

In a preferred embodiment, the pharmaceutical dosage form according to the invention contains no substances which irritate the nasal passages and/or pharynx, i.e. substances which, when administered via the nasal passages and/or pharynx, bring about a physical reaction which is either so unpleasant for the patient that he/she does not wish to or cannot continue administration, for example burning, or physiologically counteracts taking of the corresponding active compound, for example due to increased nasal secretion or sneezing. Further examples of substances which irritate the nasal passages and/or pharynx are those which cause burning, itching, urge to sneeze, increased formation of secretions or a combination of at least two of these stimuli. Corresponding substances and the quantities thereof which are conventionally to be used are known to the person skilled in the art. Some of the substances which irritate the nasal passages and/or pharynx are accordingly based on one or more constituents or one or more plant parts of a hot substance drug. Corresponding hot substance drugs are known per se to the person skilled in the art and are described, for example, in "Pharmazeutische Biologie—Drogen and ihre Inhaltsstoffe" by Prof. Dr. Hildebert Wagner, 2nd., revised edition, Gustav Fischer Verlag, Stuttgart-New York, 1982, pages 82 et seq. The corresponding description is hereby introduced as a reference and is deemed to be part of the disclosure.

The pharmaceutical dosage form according to the invention furthermore preferably contains no antagonists for the pharmacologically active ingredient, preferably no antagonists against psychotropic substances, in particular no antagonists against opioids. Antagonists suitable for a given pharmacologically active ingredient are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no antagonists selected from among the group comprising naloxone, naltrexone, nalmefene, nalide, nalmexone, nalorphine or naluphine, in each case optionally in the form of a corresponding physiologically acceptable compound, in particular in the form of a base, a salt or solvate; and no neuroleptics, for example a compound selected from among the group comprising haloperidol, promethacine, fluphenazine, perphenazine, levomepromazine, thioridazine, perazine, chlorpromazine, chlorprothixine, zuclopenthixol, flupentixol, prothipendyl, zotepine, benperidol, pipamperone, melperone and bromperidol.

The pharmaceutical dosage form according to the invention furthermore preferably contains no emetic. Emetics are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no emetic based on one or more constituents of ipecacuanha (ipecac) root, for example based on the constituent emetine, as are, for example, described in "Pharmazeutische Biologie—Drogen and ihre Inhaltsstoffe" by Prof. Dr. Hildebert Wagner, 2nd, revised edition, Gustav Fischer Verlag, Stuttgart, N.Y., 1982. The corresponding literature description is hereby introduced as a reference and is deemed to be part of the disclosure. The pharmaceutical dosage form according to the invention preferably also contains no apomorphine as an emetic.

Finally, the pharmaceutical dosage form according to the invention preferably also contains no bitter substance. Bitter substances and the quantities effective for use may be found in US-2003/0064099 A1, the corresponding disclosure of which should be deemed to be the disclosure of the present application and is hereby introduced as a reference. Examples of bitter substances are aromatic oils, such as peppermint oil, eucalyptus oil, bitter almond oil, menthol, fruit aroma substances, aroma substances from lemons, oranges, limes, grapefruit or mixtures thereof, and/or denatonium benzoate.

The pharmaceutical dosage form according to the invention accordingly preferably contains neither substances which irritate the nasal passages and/or pharynx, nor antagonists for the pharmacologically active ingredient, nor emetics, nor bitter substances.

In a preferred embodiment, the pharmaceutical dosage form provides prolonged release of the pharmacologically active ingredient.

Particularly preferably, the pharmacologically active ingredient is embedded in a prolonged release matrix comprising the EVA polymer, wherein the prolonged release matrix provides prolonged release of the pharmacologically active ingredient.

For the purpose of specification "prolonged release" preferably means a product in which the rate of release of active compound from the formulation after administration has been reduced over time, in order to maintain therapeutic activity, to reduce toxic effects, or for some other therapeutic purpose such as reducing the dosing frequency.

Preferably, under physiological conditions the pharmaceutical dosage form according to the invention has released after 30 minutes 0.1 to 75%, after 240 minutes 0.5 to 95%, after 480 minutes 1.0 to 100% and after 720 minutes 2.5 to 100% of the pharmacologically active ingredient (A). Further preferred release profiles $R_1$ to $R_8$ are summarized in the table here below [all data in wt.-% of released pharmacologically active ingredient]:

Preferably, the release profile, the pharmacologically active ingredient, the EVA polymer, the optionally present additional prolonged release matrix material and the optionally present pharmaceutical excipients of the pharmaceutical dosage form according to the invention are stable upon storage, preferably upon storage at elevated temperature, e.g. 40° C., for 3 months in sealed containers.

In connection with the release profile, the term "stable" preferably means that when comparing the initial release profile with the release profile after storage, at any given time point the release profiles deviate from one another by not more than 20%, more preferably not more than 15%, still more preferably not more than 10%, yet more preferably not more than 7.5%, most preferably not more than 5.0% and in particular not more than 2.5%.

In connection with the pharmacologically active ingredient, the EVA polymer, the optionally present additional prolonged release matrix material and the optional pharmaceutical excipients, the term "stable" preferably means that the pharmaceutical dosage forms satisfy the requirements of EMEA concerning shelf-life of pharmaceutical products.

In a preferred embodiment, the additional prolonged release matrix material exerts an influence on the release profile of the pharmacologically active ingredient. According to this embodiment, a pharmaceutical dosage form according to the invention comprising a pharmacologically active ingredient, an EVA polymer and an additional prolonged release matrix material preferably exhibits an increased release rate of the pharmacologically active ingredient than a pharmaceutical dosage form comprising the same types and amounts of the pharmacologically active ingredient and the EVA polymer but not containing any additional prolonged release matrix material.

| time | $R_1$ | $R_2$ | $R_3$ | $R_4$ | $R_5$ | $R_6$ | $R_7$ | $R_8$ |
|---|---|---|---|---|---|---|---|---|
| 60 min | 0-30 | 0-50 | 0-50 | 15-25 | 20-30 | 20-50 | 40-70 | 40-80 |
| 120 min | 0-40 | 0-75 | 0-75 | 25-40 | 35-50 | 40-75 | 60-95 | 80-100 |
| 240 min | 3-55 | 3-95 | 10-95 | 40-70 | 55-75 | 60-95 | 80-100 | |
| 480 min | 10-65 | 10-100 | 35-100 | 60-90 | 80-95 | 80-100 | 90-100 | |
| 720 min | 20-75 | 20-100 | 55-100 | 70-100 | 90-100 | 90-100 | | |
| 960 min | 30-88 | 30-100 | 70-100 | >80 | 95-100 | | | |
| 1440 min | 50-100 | 50-100 | >90 | | | | | |
| 2160 min | >80 | >80 | | | | | | |

Further preferred release profiles $R_9$ to $R_{16}$ are summarized in the table here below [all data in wt.-% of released pharmacologically active ingredient]:

In a preferred embodiment, the pharmaceutical dosage form according to the invention is adapted for administration once daily. In another preferred embodiment, the pharma-

| time | $R_9$ | $R_{10}$ | $R_{11}$ | $R_{12}$ | $R_{13}$ | $R_{14}$ | $R_{15}$ | $R_{16}$ |
|---|---|---|---|---|---|---|---|---|
| 30 min | 17.5 ± 7.5 | 25 ± 15 | 30 ± 15 | 30 ± 15 | 12 ± 10 | 5 ± 4 | 2 ± 1.5 | 50 ± 15 |
| 60 min | 27.0 ± 8.0 | 35 ± 15 | 38 ± 10 | 38 ± 10 | 18 ± 15 | 6 ± 4 | 3 ± 2 | 70 ± 10 |
| 120 min | 41.5 ± 9.5 | 43 ± 15 | 48 ± 10 | 48 ± 10 | 20 ± 10 | 8 ± 4 | 4 ± 2 | 88 ± 10 |
| 240 min | 64.5 ± 12.5 | 60 ± 15 | 55 ± 10 | 60 ± 10 | 32 ± 10 | 9 ± 5 | 5 ± 3 | 90 ± 8 |
| 480 min | 88.0 ± 12.0 | 83 ± 10 | 63 ± 10 | 68 ± 10 | 50 ± 10 | 10 ± 5 | 6 ± 4 | >95 |
| 720 min | 96.0 ± 9.0 | 98 ± 2 | 67 ± 10 | 70 ± 10 | 60 ± 10 | 12 ± 5 | 6.5 ± 5 | |
| 840 min | 97.5 ± 7.5 | >98 | 70 ± 15 | 73 ± 15 | 65 ± 20 | 17 ± 10 | 7 ± 6 | |

Suitable in vitro conditions are known to the skilled artisan. In this regard it can be referred to, e.g., the Eur. Ph. Preferably, the release profile is measured under the following conditions: Paddle apparatus equipped without sinker, 50 rpm, 37±5° C., 900 mL simulated intestinal fluid pH 6.8 (phosphate buffer) or pH 4.5. In a preferred embodiment, the rotational speed of the paddle is increased to 75 rpm.

ceutical dosage form according to the invention is adapted for administration twice daily. In still another preferred embodiment, the pharmaceutical dosage form according to the invention is adapted for administration thrice daily. In yet another preferred embodiment, the pharmaceutical dosage form according to the invention is adapted for administration more frequently than thrice daily, for example 4 times daily, 5 times daily, 6 times daily, 7 times daily or 8 times daily.

For the purpose of the specification, "twice daily" means equal or nearly equal time intervals, i.e., about every 12 hours, or different time intervals, e.g., 8 and 16 hours or 10 and 14 hours, between the individual administrations.

For the purpose of the specification, "thrice daily" means equal or nearly equal time intervals, i.e., about every 8 hours, or different time intervals, e.g., 6, 6 and 12 hours; or 7, 7 and 10 hours, between the individual administrations.

The pharmaceutical dosage form according to the invention provides tamper resistance in terms of resistance against solvent extraction, resistance against grinding, and resistance against dose-dumping in aqueous ethanol.

Preferably, the prolonged release matrix of the pharmaceutical dosage form according to the invention not only provides prolonged release of the pharmacologically active ingredient, but additionally provides tamper resistance, i.e. resistance against solvent extraction, resistance against grinding, and resistance against dose-dumping in aqueous ethanol.

As used herein, the term "tamper resistant" refers to pharmaceutical dosage forms that are resistant to conversion into a form suitable for misuse or abuse by conventional means, particular for nasal and/or intravenous administration.

In this regard, when the pharmaceutical dosage form is multiparticulate, as such it may be crushable by conventional means such as grinding in a mortar or crushing by means of a hammer. However, when the pharmaceutical dosage form is multiparticulate, the particles which contain the pharmacologically active ingredient exhibit mechanical properties such that they cannot be pulverized by conventional means any further. As the particles are of macroscopic size and contain the pharmacologically active ingredient, they cannot be administered nasally thereby rendering the pharmaceutical dosage form tamper resistant.

Further, when trying to disrupt the pharmaceutical dosage forms by means of a hammer or mortar, the particles tend to adhere to one another thereby forming aggregates and agglomerates, respectively, which are larger in size than the untreated particles.

The pharmaceutical dosage form according to the invention exhibits resistance against solvent extraction. Preferably, the prolonged release matrix provides the pharmaceutical dosage form according to the invention with resistance against solvent extraction.

Preferably, when trying to tamper the pharmaceutical dosage form in order to prepare a formulation suitable for abuse by intravenous administration, the liquid part of the formulation that can be separated from the remainder by means of a syringe at room temperature is as less as possible, preferably it contains not more than 75 or 45 or 40 wt.-%, more preferably not more than 35 wt.-%, still more preferably not more than 30 wt.-%, yet more preferably not more than 25 wt.-%, even more preferably not more than 20 wt.-%, most preferably not more than 15 wt.-% and in particular not more than 10 wt.-% of the originally contained pharmacologically active ingredient.

Preferably, this property is tested by (i) dispensing a pharmaceutical dosage form that is either intact or has been manually comminuted by means of two spoons in 5 ml of solvent, either purified water or aqueous ethanol (40 vol. %), (ii) allowing the dispersion to stand for 10 min at room temperature, (iii) drawing up the hot liquid into a syringe (needle 21 G equipped with a cigarette filter), and (iv) determining the amount of the pharmacologically active ingredient contained in the liquid within the syringe.

The pharmaceutical dosage form according to the invention exhibits resistance against grinding. Preferably, the prolonged release matrix provides the pharmaceutical dosage form according to the invention with resistance against grinding.

Preferably, when a pharmaceutical dosage form according to the invention is treated with a commercial coffee mill, preferably type Bosch MKM6000, 180W, Typ KM13 for 2 minutes, 42±17.5 wt.-%, more preferably 42±15 wt.-%, still more preferably 42±12.5 wt.-%, yet more preferably 42±10 wt.-%, even more preferably 42±7.5 wt.-%, most preferably 42±5 wt.-%, and in particular 42±2.5 wt.-%, of the total weight of the thus obtained material does not pass a sieve having a mesh size of 1.000 mm.

Preferably, when a pharmaceutical dosage form according to the invention is treated with a commercial coffee mill, preferably type Bosch MKM6000, 180W, Typ KM13, for 2 minutes, 57±17.5 wt.-%, more preferably 57±15 wt.-%, still more preferably 57±12.5 wt.-%, yet more preferably 57±10 wt.-%, even more preferably 57±7.5 wt.-%, most preferably 57±5 wt.-%, and in particular 57±2.5 wt.-%, of the total weight of the thus obtained material does not pass a sieve having a mesh size of 1.000 mm.

Preferably, when a pharmaceutical dosage form according to the invention is treated with a commercial coffee mill, preferably type Bosch MKM6000, 180W, Typ KM13, for 2 minutes, at least 50 wt.-%, more preferably at least 55 wt.-%, still more preferably at least 60 wt.-%, yet more preferably at least 65 wt.-%, even more preferably at least 70 wt.-%, most preferably at least 75 wt.-%, and in particular at least 80 wt.-%, of the total weight of the thus obtained material does not pass a sieve having a mesh size of 1.000 mm.

Particle size distributions of the ground pharmaceutical dosage form are preferably determined by sieve analysis.

In a preferred embodiment, more than 55%, more preferably more than 60%, still more preferably more than 65%, yet more preferably more than 70%, most preferably 75% and in particular more than 80% of the particles of the ground pharmaceutical dosage form have a size in the range of from 0.2 to 3.3 nm, more preferably of from 0.4 to 3.1 nm, most preferably of from 0.6 to 2.9 and in particular of from 0.7 to 2.8 nm.

Preferred particle distributions $P_1$ to $P_4$ are summarized in the table below:

| particle size | amount in % | | | |
|---|---|---|---|---|
| [nm] | $P_1$ | $P_2$ | $P_3$ | $P_4$ |
| <0.045 | 0.5 ± 0.4 | 0.1 ± 0.09 | 0.3 ± 0.29 | 0.3 ± 0.29 |
| 0.045-0.063 | 0.5 ± 0.4 | 0.3 ± 0.29 | 0.3 ± 0.29 | 0.3 ± 0.29 |
| 0.063-0.090 | 0.5 ± 0.4 | 0.3 ± 0.29 | 0.3 ± 0.29 | 1.0 ± 0.9 |
| 0.090-0.125 | 0.5 ± 0.4 | 0.3 ± 0.29 | 0.3 ± 0.29 | 1.0 ± 0.9 |
| 0.125-0.180 | 0.5 ± 0.4 | 3.0 ± 2.9 | 2.0 ± 1.5 | 2.0 ± 1.5 |
| 0.180-0.250 | 1.5 ± 1.4 | 1.0 ± 0.8 | 2.0 ± 1.5 | 1.0 ± 0.9 |
| 0.250-0.355 | 4.0 ± 3.5 | 5.0 ± 4.0 | 4.0 ± 3.5 | 3.5 ± 2.5 |
| 0.355-0.500 | 7.0 ± 6.0 | 5.0 ± 4.0 | 6.0 ± 4.5 | 7.0 ± 6.0 |
| 0.500-0.710 | 11.0 ± 8.0 | 9.0 ± 7.0 | 11.0 ± 8.0 | 10.0 ± 7.0 |
| 0.710-1.000 | 15.0 ± 12.0 | 10.0 ± 7.0 | 17.0 ± 14.0 | 18.0 ± 15.0 |
| 1.000-1.400 | 20.0 ± 17.0 | 18.0 ± 15.0 | 23.0 ± 20.0 | 28.0 ± 25.0 |
| 1.400-2.000 | 23.0 ± 20.0 | 19.0 ± 16.0 | 12.0 ± 9.0 | 18.0 ± 15.0 |
| 2.000-2.800 | 13.0 ± 10.0 | 16.0 ± 13.0 | 13.0 ± 10.0 | 11.0 ± 8.0 |
| 2.800-4.000 | 1.0 ± 0.8 | 14.0 ± 11.0 | 12.0 ± 9.0 | 0.3 ± 0.29 |
| >4.00 | 0.5 ± 0.45 | 0.3 ± 0.29 | 0.3 ± 0.29 | 0.5 ± 0.45 |

Further preferred particle distributions $P_5$ to $P_8$ are summarized in the table below:

| particle size [nm] | amount in % | | | |
|---|---|---|---|---|
| | $P_5$ | $P_6$ | $P_7$ | $P_8$ |
| <0.045 | 0.3 ± 0.29 | 0.3 ± 0.29 | 0.3 ± 0.29 | 0.3 ± 0.29 |
| 0.045-0.063 | 0.3 ± 0.29 | 0.3 ± 0.29 | 1.0 ± 0.9 | 0.3 ± 0.29 |
| 0.063-0.090 | 0.3 ± 0.29 | 0.3 ± 0.29 | 1.5 ± 1.0 | 0.3 ± 0.29 |
| 0.090-0.125 | 0.3 ± 0.29 | 1.0 ± 0.9 | 3.5 ± 3.0 | 0.3 ± 0.29 |
| 0.125-0.180 | 1.0 ± 0.9 | 1.0 ± 0.9 | 1.0 ± 0.9 | 3.0 ± 2.9 |
| 0.180-0.250 | 2.0 ± 1.5 | 1.0 ± 0.9 | 0.3 ± 0.29 | 1.5 ± 1.0 |
| 0.250-0.355 | 5.0 ± 4.0 | 3.0 ± 2.9 | 0.3 ± 0.29 | 2.0 ± 1.9 |
| 0.355-0.500 | 7.0 ± 6.0 | 7.0 ± 6.0 | 5.0 ± 4.0 | 1.0 ± 0.9 |
| 0.500-0.710 | 13.0 ± 10.0 | 9.0 ± 7.0 | 8.0 ± 6.0 | 3.5 ± 2.5 |
| 0.710-1.000 | 18.0 ± 15.0 | 13.0 ± 10.0 | 55.0 ± 30.0 | 19.5 ± 15.0 |
| 1.000-1.400 | 25.0 ± 22.0 | 20.0 ± 17.0 | 6.5 ± 5.0 | 70.1 ± 50.0 |
| 1.400-2.000 | 10.0 ± 7.0 | 22.0 ± 19.0 | 13.0 ± 10.0 | 2.0 ± 1.9 |
| 2.000-2.800 | 14.0 ± 11.0 | 12.0 ± 9.0 | 3.0 ± 2.9 | 0.3 ± 0.29 |
| 2.800-4.000 | 4.0 ± 3.5 | 9.0 ± 7.0 | 2.0 ± 1.9 | 0.3 ± 0.29 |
| >4.00 | 0.3 ± 0.29 | 0.5 ± 0.45 | 13.0 ± 10.0 | 1.5 ± 1.0 |

In a preferred embodiment, the pharmaceutical dosage form according to the invention is monolithic and has a breaking strength of at least 300 N or, when the pharmaceutical dosage form according to the invention is multiparticulate, at least a fraction of the individual particles have a breaking strength of at least 300 N.

Preferably, the mechanical properties, particularly the breaking strength, substantially relies on the presence and spatial distribution of the EVA polymer (the prolonged release matrix material), although its mere presence does typically not suffice in order to achieve said properties. The advantageous mechanical properties may not automatically be achieved by simply processing pharmacologically active ingredient, EVA polymer (the prolonged release matrix material), optionally additional prolonged release matrix material, and optionally further excipients by means of conventional methods for the preparation of pharmaceutical dosage forms. In fact, usually suitable apparatuses must be selected for the preparation and critical processing parameters must be adjusted, particularly pressure/force, temperature and time. Thus, even if conventional apparatuses are used, the process protocols usually must be adapted in order to meet the required criteria.

In general, the desired properties may be obtained only if, during preparation of the pharmaceutical dosage form,
  suitable components
  in suitable amounts
are exposed to
  a sufficient pressure
  at a sufficient temperature
  for a sufficient period of time.

Thus, regardless of the apparatus used, the process protocols must be adapted in order to meet the required criteria. Therefore, the breaking strength is separable from the composition.

The pharmaceutical dosage form or, when it is multiparticulate, the particles according to the invention which contain the pharmacologically active ingredient preferably have a breaking strength of at least 300 N, at least 400 N, or at least 500 N, preferably at least 600 N, more preferably at least 700 N, still more preferably at least 800 N, yet more preferably at least 1000 N, most preferably at least 1250 N and in particular at least 1500 N.

When the pharmaceutical dosage form is an oblong tablet, preferably the breaking strengths of the pharmaceutical dosage form across and lengthwise are each at least 200 N, at least 300 N, at least 400 N, at least 500 N, at least 600 N, at least 700 N, at least 800 N, at least 1000 N or at least 1500 N.

The "breaking strength" (resistance to crushing) of a pharmaceutical dosage form and of a particle is known to the skilled person. In this regard it can be referred to, e.g., W. A. Ritschel, Die Tablette, 2. Auflage, Editio Cantor Verlag Aulendorf, 2002; H Liebermann et al., Pharmaceutical dosage forms: Pharmaceutical dosage forms, Vol. 2, Informa Healthcare; 2 edition, 1990; and Encyclopedia of Pharmaceutical Technology, Informa Healthcare; 1 edition.

For the purpose of specification, the breaking strength is preferably defined as the amount of force that is necessary in order to fracture a pharmaceutical dosage form and a particle, respectively (=breaking force). Therefore, for the purpose of specification, a pharmaceutical dosage form and a particle, respectively, does preferably not exhibit the desired breaking strength when it breaks, i.e., is fractured into at least two independent parts that are separated from one another. In another preferred embodiment, however, the pharmaceutical dosage form and particle, respectively, is regarded as being broken if the force decreases by 25% (threshold value) of the highest force measured during the measurement (see below).

The pharmaceutical dosage forms and particles, respectively, according to the invention are distinguished from conventional pharmaceutical dosage forms and particles, respectively, in that due to their breaking strength, they cannot be pulverized by the application of force with conventional means, such as for example a pestle and mortar, a hammer, a mallet or other usual means for pulverization, in particular devices developed for this purpose (pharmaceutical dosage form crushers). In this regard "pulverization" means crumbling into small particles. Avoidance of pulverization virtually rules out oral or parenteral, in particular intravenous or nasal abuse.

Conventional pharmaceutical dosage forms and particles, respectively, typically have a breaking strength well below 200 N.

The breaking strength of conventional round pharmaceutical dosage forms/particles may be estimated according to the following empirical formula:

$$\text{Breaking Strength [in N]}=10\times\text{Diameter of pharmaceutical dosage form/particle [in mm]}.$$

Thus, according to said empirical formula, a round pharmaceutical dosage form/particle having a breaking strength of at least 300 N would require a diameter of at least 30 mm. Such a particle, however, could not be swallowed, let alone a pharmaceutical dosage form containing a plurality of such particles. The above empirical formula preferably does not apply to the pharmaceutical dosage form and particles, respectively, according to the invention, which are not conventional but rather special.

Further, the actual mean chewing force is about 220 N (cf., e.g., P. A. Proeschel et al., J Dent Res, 2002, 81(7), 464-468). This means that conventional pharmaceutical dosage forms and particle, respectively, having a breaking strength well below 200 N may be crushed upon spontaneous chewing, whereas the pharmaceutical dosage forms and particles, respectively, according to the invention may preferably not.

Still further, when applying a gravitational acceleration of about 9.81 m/s$^2$, 300 N correspond to a gravitational force of more than 30 kg, i.e. the pharmaceutical dosage form and particle, respectively, according to the invention can preferably withstand a weight of more than 30 kg without being pulverized.

Methods for measuring the breaking strength are known to the skilled artisan. Suitable devices are commercially available.

For example, the breaking strength (resistance to crushing) can be measured in accordance with the Eur. Ph. 5.0, 2.9.8 or 6.0, 2.09.08 "Resistance to Crushing of Pharmaceutical dosage forms". The particles may be subjected to the same or similar breaking strength test as the pharmaceutical dosage form. The test is intended to determine, under defined conditions, the resistance to crushing of pharmaceutical dosage forms and individual particles, respectively, measured by the force needed to disrupt them by crushing. The apparatus consists of 2 jaws facing each other, one of which moves towards the other. The flat surfaces of the jaws are perpendicular to the direction of movement. The crushing surfaces of the jaws are flat and larger than the zone of contact with the pharmaceutical dosage form and individual particle, respectively. The apparatus is calibrated using a system with a precision of 1 Newton. The pharmaceutical dosage form and particle, respectively, is placed between the jaws, taking into account, where applicable, the shape, the break-mark and the inscription; for each measurement the pharmaceutical dosage form and particle, respectively, is oriented in the same way with respect to the direction of application of the force (and the direction of extension in which the breaking strength is to be measured). The measurement is carried out on 10 pharmaceutical dosage forms and particles, respectively, taking care that all fragments have been removed before each determination. The result is expressed as the mean, minimum and maximum values of the forces measured, all expressed in Newton.

A similar description of the breaking strength (breaking force) can be found in the USP. The breaking strength can alternatively be measured in accordance with the method described therein where it is stated that the breaking strength is the force required to cause a pharmaceutical dosage form and particle, respectively, to fail (i.e., break) in a specific plane. The pharmaceutical dosage forms and particles, respectively, are generally placed between two platens, one of which moves to apply sufficient force to the pharmaceutical dosage form and particle, respectively, to cause fracture. For conventional, round (circular cross-section) pharmaceutical dosage forms and particles, respectively, loading occurs across their diameter (sometimes referred to as diametral loading), and fracture occurs in the plane. The breaking force of pharmaceutical dosage forms and particles, respectively, is commonly called hardness in the pharmaceutical literature; however, the use of this term is misleading. In material science, the term hardness refers to the resistance of a surface to penetration or indentation by a small probe. The term crushing strength is also frequently used to describe the resistance of pharmaceutical dosage forms and particle, respectively, to the application of a compressive load. Although this term describes the true nature of the test more accurately than does hardness, it implies that pharmaceutical dosage forms and particles, respectively, are actually crushed during the test, which is often not the case.

Alternatively, the breaking strength (resistance to crushing) can be measured in accordance with WO 2008/107149, which can be regarded as a modification of the method described in the Eur. Ph. The apparatus used for the measurement is preferably a "Zwick Z 2.5" materials tester, $F_{max}$=2.5 kN with a maximum draw of 1150 mm, which should be set up with one column and one spindle, a clearance behind of 100 mm and a test speed adjustable between 0.1 and 800 mm/min together with testControl software. Measurement is performed using a pressure piston with screw-in inserts and a cylinder (diameter 10 mm), a force transducer, $F_{max}$=1 kN, diameter=8 mm, class 0.5 from 10 N, class 1 from 2 N to ISO 7500-1, with manufacturer's test certificate M according to DIN 55350-18 (Zwick gross force $F_{max}$=1.45 kN) (all apparatus from Zwick GmbH & Co. KG, Ulm, Germany) with Order No BTC-FR 2.5 TH. D09 for the tester, Order No BTC-LC 0050N. P01 for the force transducer, Order No BO 70000 S06 for the centering device.

In a preferred embodiment, the pharmaceutical dosage form and particle, respectively, is regarded as being broken if it is fractured into at least two separate pieces.

The pharmaceutical dosage form and particle, respectively, according to the invention preferably exhibit mechanical strength over a wide temperature range, in addition to the breaking strength (resistance to crushing) optionally also sufficient hardness, impact resistance, impact elasticity, tensile strength and/or modulus of elasticity, optionally also at low temperatures (e.g. below −24° C., below −40° C. or possibly even in liquid nitrogen), for it to be virtually impossible to pulverize by spontaneous chewing, grinding in a mortar, pounding, etc. Thus, preferably, the comparatively high breaking strength of the pharmaceutical dosage form and particle, respectively, according to the invention is maintained even at low or very low temperatures, e.g., when the pharmaceutical dosage form is initially chilled to increase its brittleness, for example to temperatures below −25° C., below −40° C. or even in liquid nitrogen.

The pharmaceutical dosage form and particle, respectively, according to the invention is characterized by a certain degree of breaking strength. This does not mean that it must also exhibit a certain degree of hardness. Hardness and breaking strength are different physical properties. Therefore, the tamper resistance of the pharmaceutical dosage form does not necessarily depend on the hardness of the pharmaceutical dosage form and particle, respectively. For instance, due to its breaking strength, impact strength, elasticity modulus and tensile strength, respectively, the pharmaceutical dosage form and particle, respectively, can preferably be deformed, e.g. plastically, when exerting an external force, for example using a hammer, but cannot be pulverized, i.e., crumbled into a high number of fragments. In other words, the pharmaceutical dosage form and particle, respectively, according to the invention are characterized by a certain degree of breaking strength, but not necessarily also by a certain degree of form stability.

Therefore, in the meaning of the specification, a pharmaceutical dosage form and particle, respectively, that is deformed when being exposed to a force in a particular direction of extension but that does not break (plastic deformation or plastic flow) is preferably to be regarded as having the desired breaking strength in said direction of extension.

Preferred pharmaceutical dosage forms and particles, respectively, are those having a suitable tensile strength as determined by a test method currently accepted in the art. Further preferred pharmaceutical dosage forms and particles, respectively, are those having a Young's Modulus as determined by a test method of the art. Still further preferred pharmaceutical dosages form and particles, respectively, are those having an acceptable elongation at break.

The pharmaceutical dosage form according to the invention exhibits resistance against dose-dumping in aqueous ethanol. Preferably, the prolonged release matrix provides the pharmaceutical dosage form according to the invention with resistance against dose-dumping in aqueous ethanol.

The pharmaceutical dosage form can be tested in vitro using ethanol/simulated gastric fluid of 0%, 20% and 40% to evaluate alcohol extractability. Testing is preferably performed using standard procedures, e.g. USP Apparatus 1 (basket) or USP Apparatus 2 (paddle) at e.g. 50 rpm or 75 rpm in e.g. 500 ml of media at 37° C., using a Perkin Elmer UV/VIS Spectrometer Lambda 20, UV at an appropriate wavelength for detection of the pharmacologically active ingredient present therein. Sample time points preferably include 0.5 and 1 hour.

Preferably, when comparing the in vitro release profile at 37° C. in simulated gastric fluid with the in vitro release profile in ethanol/simulated gastric fluid (40 vol.-%) at 37° C., the in vitro release in ethanol/simulated gastric fluid (40 vol.-%) is preferably not substantially accelerated compared to the in vitro release in simulated gastric fluid. Preferably, in this regard "substantially" means that at any given time point the in vitro release in ethanol/simulated gastric fluid (40 vol.-%) relatively deviates from the in vitro release in simulated gastric fluid by not more than +25%, more preferably not more than +20%, still more preferably not more than +15%, yet more preferably not more than +10%, even more preferably not more than +7.5%, most preferably not more than +5.0% and in particular not more than +2.5%.

A substantial relative acceleration of the in vitro release in ethanol/simulated gastric fluid (40 vol.-%) compared to the in vitro release in simulated gastric fluid is to be prevented according to the invention. However, a substantial relative deceleration of the in vitro release in ethanol/simulated gastric fluid (40 vol.-%) compared to the in vitro release in simulated gastric fluid, e.g., a relative deviation by −25% or more, may be possible and can even be desirable.

The pharmacologically active ingredient having psychotropic action is not particularly limited.

For the purpose of definition, a pharmacologically active ingredient having psychotropic action is preferably meant to refer to any pharmacologically active ingredient which crosses the blood-brain barrier and acts primarily upon the central nervous system where it affects brain function, resulting in alterations in perception, mood, consciousness, cognition, and behavior.

In a preferred embodiment, the pharmaceutical dosage form contains only a single pharmacologically active ingredient. In another preferred embodiment, the pharmaceutical dosage form contains a combination of two or more pharmacologically active ingredients.

Preferably, the pharmaceutical dosage form according to the invention comprises a pharmacologically active ingredient having potential for abuse and potential for dose dumping in ethanol. Active ingredients with potential for being abused are known to the person skilled in the art and comprise e.g. tranquilizers, stimulants, barbiturates, narcotics, opioids or opioid derivatives.

Preferably, the pharmacologically active ingredient is selected from the group consisting of opiates, opioids, stimulants, tranquilizers, other narcotics and anesthetics. Preferably, the pharmacologically active ingredient is selected from the group consisting of ethers; halogenated hydrocarbons; pain barbiturates; and barbiturates in combination with other drugs; opioid anesthetics; or any other general anesthetics.

In a particularly preferred embodiment, the pharmacologically active ingredient is an opioid or a physiologically acceptable salt thereof.

According to the ATC index, opioids are divided into natural opium alkaloids, phenylpiperidine derivatives, diphenylpropylamine derivatives, benzomorphan derivatives, oripavine derivatives, morphinan derivatives and others.

The following opiates, opioids, tranquillizers, anesthetics or other narcotics are substances with a psychotropic action, i.e. have a potential of abuse, and hence are preferably contained in the pharmaceutical dosage form and the particles, respectively: alfentanil, allobarbital, allylprodine, alphaprodine, alprazolam, amfepramone, amphetamine, amphetaminil, amobarbital, anileridine, apocodeine, axomadol, barbital, bemidone, benzylmorphine, bezitramide, bromazepam, brotizolam, buprenorphine, butobarbital, butorphanol, camazepam, carfentanil, cathine/D-norpseudoephedrine, chlordiazepoxide, clobazam clofedanol, clonazepam, clonitazene, clorazepate, clotiazepam, cloxazolam, cocaine, codeine, cyclobarbital, cyclorphan, cyprenorphine, delorazepam, desomorphine, dextromoramide, dextropropoxyphene, dezocine, diampromide, diamorphine, diazepam, dihydrocodeine, dihydromorphine, dihydromorphone, dimenoxadol, dimephetamol, dimethylthiambutene, dioxaphetylbutyrate, dipipanone, dronabinol, eptazocine, estazolam, ethoheptazine, ethylmethylthiambutene, ethyl loflazepate, ethylmorphine, etonitazene, etorphine, faxeladol, fencamfamine, fenethylline, fenpipramide, fenproporex, fentanyl, fludiazepam, flunitrazepam, flurazepam, halazepam, haloxazolam, heroin, hydrocodone, hydromorphone, hydroxypethidine, isomethadone, hydroxymethylmorphinan, ketamine, (S)-ketamine, ketazolam, ketobemidone, levacetylmethadol (LAAM), levomethadone, levorphanol, levophenacylmorphane, levoxemacin, lisdexamfetamine dimesylate, lofentanil, loprazolam, lorazepam, lormetazepam, mazindol, medazepam, mefenorex, meperidine, meprobamate, metapon, meptazinol, metazocine, methylmorphine, metamphetamine, methadone, methaqualone, 3-methylfentanyl, 4-methylfentanyl, methylphenidate, methylphenobarbital, methyprylon, metopon, midazolam, modafinil, morphine, myrophine, nabilone, nalbuphene, nalorphine, narceine, nicomorphine, nimetazepam, nitrazepam, nordazepam, norlevorphanol, normethadone, normorphine, norpipanone, opium, oxazepam, oxazolam, oxyco done, oxymorphone, Papaver somniferum, papaveretum, pernoline, pentazocine, pentobarbital, pethidine, phenadoxone, phenomorphane, phenazocine, phenoperidine, piminodine, pholcodeine, phenmetrazine, phenobarbital, phentermine, pinazepam, pipradrol, piritramide, prazepam, profadol, proheptazine, promedol, properidine, propoxyphene, remifentanil, secbutabarbital, secobarbital, sufentanil, tapentadol, temazepam, tetrazepam, tilidine (cis and trans), tramadol, triazolam, vinylbital, N-(1-methyl-2-piperidinoethyl)-N-(2-pyridyl)-propionamide, (1R,2R)-3-(3-dimethylamino-1-ethyl-2-methyl-propyl)phenol, (1R,2R,4S)-2-(dimethylamino)methyl-4-(p-fluorobenzyloxy)-1-(m-methoxyphenyl)cyclohexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3 (3-methoxyphenyl)-2-methyl-pentan-3-ol, (1RS,3RS,6RS)-6-dimethylaminomethyl-1-(3-methoxyphenyl)-cyclohexane-1,3-diol, preferably as racemate, 3-(2-dimethylaminomethyl-1-hydroxy-cyclohexyl)phenyl 2-(4-isobutyl-phenyl)propionate, 3-(2-dimethylaminomethyl-1-hydroxy-cyclohexyl)phenyl 2-(6-methoxy-naphthalen-2-yl)propionate, 3-(2- dimethylaminomethyl-cyclohex-1-enyl)-phenyl 2-(4-isobutyl-phenyl)propionate, 3-(2-dimethylaminomethyl-cyclohex-1-enyl)-phenyl 2-(6-methoxy-naphthalen-2-yl) propionate, (RR—SS)-2-acetoxy-4-trifluoromethyl-benzoic acid 3-(2-dimethylaminomethyl-1-hydroxy-cyclohexyl)-phenyl ester, (RR—SS)-2-hydroxy-4-trifluoromethyl-benzoic acid 3-(2-dimethylaminomethyl-1-hydroxy-cyclohexyl)-phenyl ester, (RR—SS)-4-chloro-2-hydroxy-benzoic acid 3-(2-dimethylaminomethyl-1-hydroxy-cyclohexyl)-phenyl ester, (RR—SS)-2-hydroxy-4-methyl-benzoic acid 3-(2-dimethylaminomethyl-1-hydroxy-cyclohexyl)-phenyl ester, (RR—SS)-2-hydroxy-4-methoxy-benzoic acid 3-(2-dimethylaminomethyl-1-hydroxy-cyclohexyl)-phenyl ester, (RR—SS)-2-hydroxy-5-nitro-benzoicacid 3-(2-dimethylaminomethyl-1-hydroxy-cyclohexyl)-phenyl ester, (RR—SS)-2',4'-difluoro-3-hydroxy-biphenyl-4-carboxylic acid 3-(2-dimethylaminomethyl-1-hydroxy-cyclohexyl)-phenyl ester, and corresponding stereoisomeric compounds, in each case the corresponding derivatives thereof, physiologically acceptable enantiomers, stereoisomers, diastereomers and racemates and the physiologically acceptable derivatives thereof, e.g. ethers, esters or amides, and in each case the physiologically acceptable compounds thereof, in particular the acid or base addition salts thereof and solvates, e.g. hydrochlorides.

In a preferred embodiment, the pharmacologically active ingredient is selected from the group consisting of tramadol, tapentadol, faxeladol and axomadol.

In another preferred embodiment, the pharmacologically active ingredient is selected from the group consisting of DPI-125, M6G (CE-04-410), ADL-5859, CR-665, NRP290 and sebacoyl dinalbuphine ester.

In still another preferred embodiment, the pharmacologically active ingredient is selected from the group consisting of oxycodone, oxymorphone, hydrocodone, hydromorphone, taramdol, tapentadol, morphine, buprenorphine and the physiologically acceptable salts thereof.

In yet another preferred embodiment, the pharmacologically active ingredient is selected from the group consisting of 1,1-(3-dimethylamino-3-phenylpentamethylene)-6-fluoro-1,3,4,9-tetrahydropyrano[3,4-b]indole, particularly its hemicitrate; 1,1-[3-dimethylamino-3-(2-thienyl)pentamethylene]-1,3,4,9-tetrahydropyrano[3,4-b]indole, particularly its citrate; and 1,1-[3-dimethylamino-3-(2-thienyl)pentamethylene]-1,3,4,9-tetrahydropyrano[3,4-b]-6-fluoroindole, particularly its hemicitrate. These compounds are known from, e.g., WO 2004/043967, WO 2005/066183.

The pharmacologically active ingredient may be present in form of a physiologically acceptable salt, e.g. physiologically acceptable acid addition salt.

Physiologically acceptable acid addition salts comprise the acid addition salt forms which can conveniently be obtained by treating the base form of the active ingredient with appropriate organic and inorganic acids. Active ingredients containing an acidic proton may be converted into their non-toxic metal or amine addition salt forms by treatment with appropriate organic and inorganic bases. The term addition salt also comprises the hydrates and solvent addition forms which the active ingredients are able to form. Examples of such forms are e.g. hydrates, alcoholates and the like.

It has been surprisingly found that the content of the pharmacologically active ingredient in the pharmaceutical dosage form and in the particles, respectively, can be optimized in order to provide the best compromise between tamper-resistance, disintegration time and drug release, drug load, processability (especially pharmaceutical dosage formability) and patient compliance.

The pharmacologically active ingredient is present in the pharmaceutical dosage form in a therapeutically effective amount. The amount that constitutes a therapeutically effective amount varies according to the active ingredients being used, the condition being treated, the severity of said condition, the patient being treated, and the frequency of administration.

The content of the pharmacologically active ingredient in the pharmaceutical dosage form is not limited. The dose of the pharmacologically active ingredient which is adapted for administration preferably is in the range of 0.1 mg to 500 mg, more preferably in the range of 1.0 mg to 400 mg, even more preferably in the range of 5.0 mg to 300 mg, and most preferably in the range of 10 mg to 250 mg. In a preferred embodiment, the total amount of the pharmacologically active ingredient that is contained in the pharmaceutical dosage form is within the range of from 0.01 to 200 mg, more preferably 0.1 to 190 mg, still more preferably 1.0 to 180 mg, yet more preferably 1.5 to 160 mg, most preferably 2.0 to 100 mg and in particular 2.5 to 80 mg.

Preferably, the content of the pharmacologically active ingredient is within the range of from 0.01 to 80 wt.-%, more preferably 0.1 to 50 wt.-%, still more preferably 1 to 35 wt.-%, based on the total weight of the pharmaceutical dosage form.

In a preferred embodiment, the content of pharmacologically active ingredient is within the range of from 5.0±4.5 wt.-%, or 7.5±7.0 wt.-%, or 10±9.0 wt.-%, or 12.5±12.0 wt.-%, or 15±14 wt.-%, or 17.5±17.0 wt.-%, or 20±19 wt.-%, or 22.5±22.0 wt.-%, or 25±24 wt.-%; more preferably 5.0±4.0 wt.-%, or 7.5±6.0 wt.-%, or 10±8.0 wt.-%, or 12.5±12.0 wt.-%, or 15±12 wt.-%, or 17.5±15.0 wt.-%, or 20±19 wt.-%, or 22.5±22.0 wt.-%, or 25±24 wt.-%; still more preferably 5.0±3.5 wt.-%, or 7.5±5.0 wt.-%, or 10±7.0 wt.-%, or 12.5±10.0 wt.-%, or 15±10 wt.-%, or 17.5±13.0 wt.-%, or 20±17 wt.-%, or 22.5±19.0 wt.-%, or 25±21 wt.-%; yet more preferably 5.0±3.0 wt.-%, or 7.5±4.0 wt.-%, or 10±6.0 wt.-%, or 12.5±8.0 wt.-%, or 15±8.0 wt.-%, or 17.5±11.0 wt.-%, or 20±15 wt.-%, or 22.5±16.0 wt.-%, or 25±18 wt.-%; even more preferably 5.0±2.5 wt.-%, or 7.5±3.0 wt.-%, or 10±5.0 wt.-%, or 12.5±6.0 wt.-%, or 15±6.0 wt.-%, or 17.5±9.0 wt.-%, or 20±13 wt.-%, or 22.5±13.0 wt.-%, or 25±15 wt.-%; most preferably 5.0±2.0 wt.-%, or 7.5±2.0 wt.-%, or 10±4.0 wt.-%, or 12.5±4.0 wt.-%, or 15±4.0 wt.-%, or 17.5±7.0 wt.-%, or 20±11 wt.-%, or 22.5±10.0 wt.-%, or 25±12 wt.-%; and in particular 5.0±1.5 wt.-%, or 7.5±1.0 wt.-%, or 10±3.0 wt.-%, or 12.5±2.0 wt.-%, or 15±2.0 wt.-%, or 17.5±5.0 wt.-%, or 20±9 wt.-%, or 22.5±7.0 wt.-%, or 25±9 wt.-%; in each case either based on the total weight of the pharmaceutical dosage form or, when the pharmaceutical dosage form is multiparticulate, based on the total weight of the particles that contain the pharmacologically active ingredient.

In another preferred embodiment, the content of pharmacologically active ingredient is within the range of from 20±6 wt.-%, more preferably 20±5 wt.-%, still more preferably 20±4 wt.-%, most preferably 20±3 wt.-%, and in particular 20±2 wt.-%, either based on the total weight of the pharmaceutical dosage form or, when the pharmaceutical dosage form is multiparticulate, based on the total weight of the particles that contain the pharmacologically active ingredient. In still another preferred embodiment, the content of pharmacologically active ingredient is within the range of from 25±6 wt.-%, more preferably 25±5 wt.-%, still more preferably 25±4 wt.-%, most preferably 25±3 wt.-%, and in particular 25±2 wt.-%, either based on the total weight of the pharmaceutical dosage form or, when the pharmaceutical dosage form is multiparticulate, based on the total weight of the particles that contain the pharmacologically active ingredient. In yet another preferred embodiment, the content of pharmacologically active ingredient is within the range of from 30±6 wt.-%, more preferably 30±5 wt.-%, still more preferably 30±4 wt.-%, most preferably 30±3 wt.-%, and in particular 30±2 wt.-%, either based on the total weight of the pharmaceutical dosage form or, when the pharmaceutical dosage form is multiparticulate, based on the total weight of the particles that contain the pharmacologically active ingredient. In even another preferred embodiment, the content of pharmacologically active ingredient is within the range of from 34±6 wt.-%, more preferably 34±5 wt.-%, still more preferably 34±4 wt.-%, most preferably 34±3 wt.-%, and in particular 34±2 wt.-%, either based on the total weight of the pharmaceutical dosage form or, when the pharmaceutical dosage form is multiparticulate, based on the total weight of the particles that contain the pharmacologically active ingredient. In a further preferred embodiment, the content of pharmacologically active ingredient is within the range of from 40±6 wt.-%, more preferably 40±5 wt.-%, still more preferably 40±4 wt.-%, most preferably 40±3 wt.-%, and in particular 40±2 wt.-%, either based on the total weight of the pharmaceutical dosage form or, when the pharmaceutical dosage form is multiparticulate, based on the total weight of the particles that contain the pharmacologically active ingredient.

The skilled person may readily determine an appropriate amount of pharmacologically active ingredient to include in a pharmaceutical dosage form. For instance, in the case of analgesics, the total amount of pharmacologically active ingredient present in the pharmaceutical dosage form is that sufficient to provide analgesia. The total amount of pharmacologically active ingredient administered to a patient in a dose will vary depending on numerous factors including the nature of the pharmacologically active ingredient, the weight of the patient, the severity of the pain, the nature of other therapeutic agents being administered etc.

In a preferred embodiment, the pharmacologically active ingredient is contained in the pharmaceutical dosage form in an amount of 7.5±5 mg, 10±5 mg, 20±5 mg, 30±5 mg, 40±5 mg, 50±5 mg, 60±5 mg, 70±5 mg, 80±5 mg, 90±5 mg, 100±5 mg, 110±5 mg, 120±5 mg, 130±5 mg, 140±5 mg, 150±5 mg, 160±5 mg, 170±5 mg, 180±5 mg, 190±5 mg, 200±5 mg, 210±5 mg, 220±5 mg, 230±5 mg, 240±5 mg, 250±5 mg, 260±5 mg, 270±5 mg, 280±5 mg, 290±5 mg, or 300±5 mg. In another preferred embodiment, the pharmacologically active ingredient is contained in the pharmaceutical dosage form in an amount of 5±2.5 mg, 7.5±2.5 mg, 10±2.5 mg, 15±2.5 mg, 20±2.5 mg, 25±2.5 mg, 30±2.5 mg, 35±2.5 mg, 40±2.5 mg, 45±2.5 mg, 50±2.5 mg, 55±2.5 mg, 60±2.5 mg, 65±2.5 mg, 70±2.5 mg, 75±2.5 mg, 80±2.5 mg, 85±2.5 mg, 90±2.5 mg, 95±2.5 mg, 100±2.5 mg, 105±2.5 mg, 110±2.5 mg, 115±2.5 mg, 120±2.5 mg, 125±2.5 mg, 130±2.5 mg, 135±2.5 mg, 140±2.5 mg, 145±2.5 mg, 150±2.5 mg, 155±2.5 mg, 160±2.5 mg, 165±2.5 mg, 170±2.5 mg, 175±2.5 mg, 180±2.5 mg, 185±2.5 mg, 190±2.5 mg, 195±2.5 mg, 200±2.5 mg, 205±2.5 mg, 210±2.5 mg, 215±2.5 mg, 220±2.5 mg, 225±2.5 mg, 230±2.5 mg, 235±2.5 mg, 240±2.5 mg, 245±2.5 mg, 250±2.5 mg, 255±2.5 mg, 260±2.5 mg, or 265±2.5 mg.

In a particularly preferred embodiment, the pharmacologically active ingredient is oxycodone, preferably its HCl salt, and the pharmaceutical dosage form is adapted for administration twice daily. In this embodiment, the pharmacologically active ingredient is preferably contained in the pharmaceutical dosage form in a total amount of from 1 to 80 mg. In another particularly preferred embodiment, the pharmacologically active ingredient is oxycodone, preferably its HCl salt, and the pharmaceutical dosage form is adapted for administration once daily. In this embodiment, the pharmacologically active ingredient is preferably contained in the pharmaceutical dosage form in a total amount of from 2 to 320 mg.

In another particularly preferred embodiment, the pharmacologically active ingredient is oxymorphone, preferably its HCl salt, and the pharmaceutical dosage form is adapted for administration twice daily. In this embodiment, the pharmacologically active ingredient is preferably contained in the pharmaceutical dosage form in a total amount of from 5 to 40 mg. In another particularly preferred embodiment, the pharmacologically active ingredient is oxymorphone, preferably its HCl salt, and the pharmaceutical dosage form is adapted for administration once daily. In this embodiment, the pharmacologically active ingredient is preferably contained in the pharmaceutical dosage form in a total amount of from 10 to 80 mg.

In another particularly preferred embodiment, the pharmacologically active ingredient is tapentadol, preferably its HCl salt, and the pharmaceutical dosage form is adapted for administration once daily or twice daily. In this embodiment, the pharmacologically active ingredient is preferably contained in the pharmaceutical dosage form in a total amount of from 25 to 250 mg.

In still another particularly preferred embodiment, the pharmacologically active ingredient is hydromorphone, preferably its HCl salt, and the pharmaceutical dosage form is adapted for administration twice daily. In this embodiment, the pharmacologically active ingredient is preferably contained in the pharmaceutical dosage form in a total amount of from 2 to 52 mg. In another particularly preferred embodiment, the pharmacologically active ingredient is hydromorphone, preferably its HCl salt, and the pharmaceutical dosage form is adapted for administration once daily. In this embodiment, the pharmacologically active ingredient is preferably contained in the pharmaceutical dosage form in a total amount of from 4 to 104 mg.

In yet another particularly preferred embodiment, the pharmacologically active ingredient is tramadol, preferably its HCl salt, and the pharmaceutical dosage form is adapted for administration twice daily. In this embodiment, the pharmacologically active ingredient is preferably contained in the pharmaceutical dosage form in a total amount of from 5 to 300 mg. In another particularly preferred embodiment, the pharmacologically active ingredient is tramadol, preferably its HCl salt, and the pharmaceutical dosage form is adapted for administration once daily. In this embodiment, the pharmacologically active ingredient is preferably contained in the pharmaceutical dosage form in a total amount of from 10 to 500 mg.

In another particularly preferred embodiment, the pharmacologically active ingredient is hydrocodone, preferably its HCl salt, and the pharmaceutical dosage form is adapted for administration twice daily. In this embodiment, the pharmacologically active ingredient is preferably contained in the pharmaceutical dosage form in a total amount of from 5 to 250 mg. In another particularly preferred embodiment, the pharmacologically active ingredient is hydrocodone, preferably its HCl salt, and the pharmaceutical dosage form is adapted for administration once daily. In this embodiment, the pharmacologically active ingredient is preferably contained in the pharmaceutical dosage form in a total amount of from 5 to 250 mg.

In still another particularly preferred embodiment, the pharmacologically active ingredient is morphine, preferably its HCl or $H_2SO_4$ salt, and the pharmaceutical dosage form is adapted for administration twice daily. In this embodiment, the pharmacologically active ingredient is preferably contained in the pharmaceutical dosage form in a total amount of from 5 to 250 mg. In another particularly preferred embodiment, the pharmacologically active ingredient is morphine, preferably its HCl or $H_2SO_4$ salt, and the pharmaceutical dosage form is adapted for administration once daily. In this embodiment, the pharmacologically active ingredient is preferably contained in the pharmaceutical dosage form in a total amount of from 5 to 250 mg.

In another particularly preferred embodiment, the pharmacologically active ingredient is buprenorphine, preferably its HCl salt, and the pharmaceutical dosage form is adapted for administration twice daily. In this embodiment, the pharmacologically active ingredient is preferably contained in the pharmaceutical dosage form in a total amount of from 1 to 12 mg. In another particularly preferred embodiment, the pharmacologically active ingredient is buprenorphine, preferably its HCl salt, and the pharmaceutical dosage form is adapted for administration once daily. In this embodiment, the pharmacologically active ingredient is preferably contained in the pharmaceutical dosage form in a total amount of from 2 to 12 mg.

When the pharmaceutical dosage form is multiparticulate, the particles present in the pharmaceutical dosage forms according to the invention preferably comprise 3 to 75 wt.-% of pharmacologically active ingredient, more preferably 5 to 70 wt.-% of pharmacologically active ingredient, still more preferably 7.5 to 65 wt.-% of pharmacologically active ingredient, based on the total weight of a particle.

When the pharmaceutical dosage form is multiparticulate, the content of the pharmacologically active ingredient is preferably at least 5 wt.-%, more preferably at least 10 wt.-%, still more preferably at least 15 wt.-%, yet more preferably at least 20 wt.-%, most preferably at least 25 wt.-% and in particular at least 30 wt.-%, based on the total weight of a particle.

When the pharmaceutical dosage form is multiparticulate, the content of the pharmacologically active ingredient is preferably at most 70 wt.-%, more preferably at most 65 wt.-%, still more preferably at most 60 wt.-%, yet more preferably at most 55 wt.-%, most preferably at most 50 wt.-%, based on the total weight of a particle.

In a preferred embodiment, when the pharmaceutical dosage form is multiparticulate, the content of the pharmacologically active ingredient is within the range of 35±30 wt.-%, more preferably 35±25 wt.-%, still more preferably 35±20 wt.-%, yet more preferably 35±15 wt.-%, most preferably 35±10 wt.-%, and in particular 35±5 wt.-%, based on the total weight of a particle. In another preferred embodiment, when the pharmaceutical dosage form is multiparticulate, the content of the pharmacologically active ingredient is within the range of 45±30 wt.-%, more preferably 45±25 wt.-%, still more preferably 45±20 wt.-%, yet more preferably 45±15 wt.-%, most preferably 45±10 wt.-%, and in particular 45±5 wt.-%, based on the total weight of a particle. In still another preferred embodiment, when the pharmaceutical dosage form is multiparticulate, the content of the pharmacologically active ingredient is within the range of 55±30 wt.-%, more preferably 55±25 wt.-%, still more preferably 55±20 wt.-%, yet more preferably 55±15 wt.-%, most preferably 55±10 wt.-%, and in particular 55±5 wt.-%, based on the total weight of a particle.

The pharmacologically active ingredient that is included in the preparation of the pharmaceutical dosage forms according to the invention preferably has an average particle size of less than 500 microns, still more preferably less than 300 microns, yet more preferably less than 200 or 100 microns. There is no lower limit on the average particle size and it may be, for example, 50 microns. The particle size of pharmacologically active ingredients may be determined by any technique conventional in the art, e.g. laser light scattering, sieve analysis, light microscopy or image analysis. Generally speaking it is preferable that the largest dimension of the pharmacologically active ingredient particle be less than the size of the particles (e.g. less than the smallest dimension of the particles).

In a preferred embodiment, the pharmaceutical dosage form according to the invention, preferably the particles, comprise an opioid (agonist) as well as an opioid antagonist.

Any conventional opioid antagonist may be present, e.g. naltrexone or naloxone or their pharmaceutically acceptable salts. Naloxone, including its salts, is particularly preferred. The opioid antagonist may be present within the particles or within the matrix. Alternatively, opioid antagonist may be provided in separate particles to the pharmacologically active ingredients. The preferred composition of such particles is the same as that described for pharmacologically active ingredient-containing particles.

The ratio of opioid agonist to opioid antagonist in the pharmaceutical dosage forms according to the invention is preferably 1:1 to 3:1 by weight, for example, about 2:1 by weight.

In another preferred embodiment, neither the particles nor the pharmaceutical dosage form comprise any opioid antagonist.

Preferably, the pharmaceutical dosage form according to the invention contains more than 20 wt.-%, more preferably more than 30 wt.-%, still more preferably more than 40 wt.-%, yet more preferably more than 50 wt.-%, most preferably more than 60 wt.-%, and in particular more than 70 wt.-% of compounds which are not or hardly soluble in ethanol with respect to the total weight of the pharmaceutical dosage form.

For the purpose of specification, compounds which are not or hardly soluble in ethanol have a maximum solubility in aqueous ethanol (96%) at room temperature of preferably less than 1000 mg/L, more preferably less than 800 mg/L, even more preferably less than 500 mg/L, most preferably less than 100 mg/L and in particular less than 10 mg/L or less than 1 mg/L.

Preferably, the pharmaceutical dosage form according to the invention contains more than 50 wt.-%, more preferably more than 60 wt.-%, still more preferably more than 70 wt.-%, yet more preferably more than 80 wt.-%, most preferably more than 90 wt.-%, and in particular more than 95 wt.-% of polymers which are not or hardly soluble in ethanol with respect to the overall amount of polymers contained in the pharmaceutical dosage form.

Preferred polymers which are not or hardly soluble in ethanol according to the invention are xanthan, guar gum and some types of HPMC. The skilled person knows what types of HPMC are not or hardly soluble in ethanol within the sense of the invention.

In a particularly preferred embodiment, the entire pharmaceutical dosage form according to the invention contains polymers which are not or hardly soluble in ethanol and polymers which are soluble in ethanol, wherein the amount of polymers which are not or hardly soluble in ethanol relative to the total amount of polymers contained in the dosage form is 30 to 100 wt.-%, more preferably 50 to 100 wt.-%, still more preferably 60 to 95 wt.-% or 100 wt.-%, yet more preferably 70 to 90 wt.-% or 100 wt.-%, most preferably 80 to 90 wt.-% or 90 to 100 wt.-%, and in particular more than 95 wt.-% or more than 99 wt.-%.

Preferred compositions of the pharmaceutical dosage form or, when the pharmaceutical dosage form is multiparticulate, of the particles are summarized as embodiments $B^1$ to $B^6$ in the table here below:

| wt.-% [a] | $B^1$ | $B^2$ | $B^3$ | $B^4$ | $B^5$ | $B^6$ |
|---|---|---|---|---|---|---|
| pharmacologically active ingredient | 40 ± 10 | 40 ± 5 | 35 ± 10 | 33 ± 10 | 33 ± 10 | 33 ± 10 |
| EVA polymer | 40 ± 10 | 40 ± 5 | 50 ± 15 | 57 ± 20 | 60 ± 20 | 67 ± 15 |
| additional prolonged release matrix material | 10 ± 10 | 10 ± 10 | 15 ± 10 | 10 ± 7 | 7.5 ± 5 | 10 ± 10 |
| excipients | 10 ± 10 | 10 ± 10 | 5 ± 5 | 5 ± 5 | 5 ± 5 | 5 ± 5 |

[a] relative to the total weight of the dosage form and particles, respectively.

The subjects to which the pharmaceutical dosage forms according to the invention can be administered are not particularly limited. Preferably, the subjects are animals, more preferably human beings.

The pharmaceutical dosage form according to the invention or, when it is multiparticulate, the particles that contain the pharmacologically active ingredient are preferably thermoformed, preferably by melt-extrusion, although also other methods of thermoforming may be useful, such as press-molding at elevated temperature or heating of compacts that were manufactured by conventional compression in a first step and then heated above the softening temperature of the EVA polymer and the prolonged release matrix material, respectively, in a second step to form break resistant, hardened compacts, i.e. monolithic dosage forms or particles, respectively. In this regard, thermoforming preferably means the forming or molding of a mass after, before or during the application of heat. Preferably, thermoforming is performed by hot-melt extrusion.

In a preferred embodiment, the pharmaceutical dosage form according to the invention is hot-melt extruded.

In a preferred embodiment, hot-melt extrusion is performed by means of a twin-screw-extruder. Melt extrusion preferably provides a melt-extruded strand that is preferably cut into monoliths, which are then optionally compressed and formed. Preferably, compression is achieved by means of a die and a punch, preferably from a monolithic mass obtained by melt extrusion. If obtained via melt extrusion, the compressing step is preferably carried out with a monolithic mass exhibiting ambient temperature, that is, a temperature in the range from 20 to 25° C.

The strands obtained by way of extrusion can either be subjected to the compression step as such or can be cut prior to the compression step. This cutting can be performed by usual techniques, for example using rotating knives or compressed air, at elevated temperature, e.g. when the extruded stand is still warm due to hot-melt extrusion, or at ambient temperature, i.e. after the extruded strand has been allowed to cool down. When the extruded strand is still warm, singulation of the extruded strand into extruded monolithic pharmaceutical dosage forms and particles, respectively, is preferably performed by cutting the extruded strand immediately after it has exited the extrusion die.

However, when the extruded strand is cut in the cooled state, subsequent singulation of the extruded strand is preferably performed by optionally transporting the still hot extruded strand by means of conveyor belts, allowing it to cool down and to congeal, and subsequently cutting it. Alternatively, the shaping can take place as described in EP-A 240 906 by the extrudate being passed between two counter-rotating calender rolls and being shaped directly to pharmaceutical dosage forms and particles, respectively. It is of course also possible to subject the extruded strands to the compression step or to the cutting step when still warm, that is more or less immediately after the extrusion step. The extrusion is preferably carried out by means of a twin-screw extruder.

The pharmaceutical dosage forms and particles, respectively, according to the invention may be produced by different processes, the particularly preferred of which are explained in greater detail below. Several suitable processes have already been described in the prior art. In this regard it can be referred to, e.g., WO 2005/016313, WO 2005/016314, WO 2005/063214, WO 2005/102286, WO 2006/002883, WO 2006/002884, WO 2006/002886, WO 2006/082097, and WO 2006/082099.

In general, the process for the production of the particles according to the invention preferably comprises the following steps:

(a) mixing all ingredients;
(b) optionally pre-forming the mixture obtained from step (a), preferably by applying heat and/or force to the mixture obtained from step (a), the quantity of heat supplied preferably not being sufficient to heat the EVA polymer and the prolonged release matrix material, respectively, up to its softening point;
(c) hardening the mixture by applying heat and force, it being possible to supply the heat during and/or before the application of force and the quantity of heat supplied being sufficient to heat the EVA polymer and the prolonged release matrix material, respectively, at least up to its softening point; and thereafter allowing the material to cool and removing the force
(d) optionally singulating the hardened mixture;
(e) optionally shaping the particles; and
(f) optionally providing a film coating.

Heat may be supplied directly, e.g. by contact or by means of hot gas such as hot air, or with the assistance of ultrasound; or is indirectly supplied by friction and/or shear. Force may be applied and/or the particles may be shaped for example by direct pharmaceutical dosage forming or with the assistance of a suitable extruder, particularly by means of a screw extruder equipped with one or two screws (single-screw-extruder and twin-screw-extruder, respectively) or by means of a planetary gear extruder.

The final shape of the pharmaceutical dosage forms and particles, respectively, may either be provided during the hardening of the mixture by applying heat and force (step (c)) or in a subsequent step (step (e)). In both cases, the mixture of all components is preferably in the plastified state, i.e. preferably, shaping is performed at a temperature at least above the softening point of the EVA polymer and the prolonged release matrix material, respectively. However, extrusion at lower temperatures, e.g. ambient temperature, is also possible and may be preferred.

Shaping can be performed, e.g., by means of a pharmaceutical dosage forming press comprising die and punches of appropriate shape.

Another aspect of the invention relates to a process for the production of a tamper-resistant, oral pharmaceutical dosage form comprising the steps of
(i) mixing a pharmacologically active ingredient, an ethylene-vinyl acetate (EVA) polymer and optionally further excipients; and
(ii) thermoforming the mixture obtained in step (i), wherein said mixture is simultaneously or before or after the application of heat subjected to pressure.

In a preferred embodiment, the tamper-resistant, oral pharmaceutical dosage form which is produced by said process is according to the tamper-resistant, oral pharmaceutical dosage forms described above.

A particularly preferred process for the manufacture of the particles according to the invention involves hot-melt extrusion. In this process, the pharmaceutical dosage forms and particles, respectively, according to the invention are produced by thermoforming with the assistance of an extruder, preferably without there being any observable consequent discoloration of the extrudate.

This process is characterized in that
a) all components are mixed,
b) the resultant mixture is heated in the extruder at least up to the softening point of the EVA polymer and the prolonged release matrix material, respectively, and extruded through the outlet orifice of the extruder by application of force,
c) the still plastic extrudate is singulated and formed into the pharmaceutical dosage forms and particles, respectively, or
d) the cooled and optionally reheated singulated extrudate is formed into the pharmaceutical dosage forms and particles, respectively.

Mixing of the components according to process step a) may also proceed in the extruder.

The components may also be mixed in a mixer known to the person skilled in the art. The mixer may, for example, be a roll mixer, shaking mixer, shear mixer or compulsory mixer.

The, preferably molten, mixture which has been heated in the extruder at least up to the softening point of the EVA polymer and the prolonged release matrix material, respectively, is extruded from the extruder through a die with at least one bore.

The process according to the invention requires the use of suitable extruders, preferably screw extruders. Screw extruders which are equipped with two screws (twin-screw-extruders) are particularly preferred.

In a preferred embodiment, extrusion is performed in the absence of water, i.e., no water is added. However, traces of water (e.g., caused by atmospheric humidity) may be present.

The extruded strand is preferably water-free, which preferably means that the water content of the extruded strand is preferably at most 10 wt.-%, or at most 7.5 wt.-%, or at most 5.0 wt.-%, or at most 4.0 wt.-%, or at most 3.0 wt.-%, or at most 2.0 wt.-%, more preferably at most 1.7 wt.-%, still more preferably at most 1.5 wt.-%, yet more preferably at most 1.3 wt.-%, even more preferably at most 1.0 wt.-%, most preferably at most 0.7 wt.-%, and in particular at most 0.5 wt.-%.

The extruder preferably comprises at least two temperature zones, with heating of the mixture at least up to the softening point of the EVA polymer and the prolonged release matrix material, respectively, proceeding in the first zone, which is downstream from a feed zone and optionally mixing zone. The throughput of the mixture is preferably from 1.0 kg to 15 kg/hour. In a preferred embodiment, the throughput is from 0.2 kg/hour to 3.5 kg/hour. In another preferred embodiment, the throughput is from 4 to 15 kg/hour.

In a preferred embodiment, the die head pressure is within the range of from 0.5 to 200 bar. The die head pressure can be adjusted inter alia by die geometry, temperature profile, extrusion speed, number of bores in the dies, screw configuration, first feeding steps in the extruder, and the like.

In a preferred embodiment, the die head pressure is within the range of from 20±19 bar, more preferably 20±15 bar, and in particular 20±10 bar; or the die head pressure is within the range of from 30±20 bar, more preferably 30±15 bar, and in particular 30±10 bar; or the die head pressure is within the range of from 40±20 bar, more preferably 40±15 bar, and in particular 40±10 bar; or the die head pressure is within the range of from 50±20 bar, more preferably 50±15 bar, and in particular 50±10 bar; or the die head pressure is within the range of from 60±20 bar, more preferably 60±15 bar, and in particular 60±10 bar; or the die head pressure is within the range of from 70±20 bar, more preferably 70±15 bar, and in particular 70±10 bar; or the die head pressure is within the range of from 80±20 bar, more preferably 80±15 bar, and in particular 80±10 bar; or the die head pressure is within the range of from 90±20 bar, more preferably 90±15 bar, and in particular 90±10 bar; or the die head pressure is within the range of from 100±20 bar, more preferably 100±15 bar, and in particular 100±10 bar.

The die geometry or the geometry of the bores is freely selectable. The die or the bores may accordingly exhibit a flat (film), round, oblong or oval cross-section, wherein the round cross-section preferably has a diameter of 0.1 mm to 2 mm for extruded particles and a larger diameter for extruded monolithic pharmaceutical dosage forms. Preferably, the die or the bores have a round cross-section. The casing of the extruder used according to the invention may be heated or cooled. The corresponding temperature control, i.e. heating or cooling, is so arranged that the mixture to be extruded exhibits at least an average temperature (product temperature) corresponding to the softening temperature of the prolonged release matrix material and does not rise above a temperature at which the pharmacologically active ingredient to be processed may be damaged. Preferably, the temperature of the mixture to be extruded is adjusted to below 180° C., preferably below 150° C., but at least to the softening temperature of the EVA polymer and the prolonged release matrix material, respectively. Typical extrusion temperatures are 120° C. and 150° C.

In a preferred embodiment, the extruder torque is within the range of from 30 to 95%. Extruder torque can be adjusted inter alia by die geometry, temperature profile, extrusion speed, number of bores in the dies, screw configuration, first feeding steps in the extruder, and the like.

After extrusion of the molten mixture and optional cooling of the extruded strand or extruded strands, the extrudates are preferably singulated. This singulation may preferably be performed by cutting up the extrudates by means of revolving or rotating knives, wires, blades or with the assistance of laser cutters.

Preferably, intermediate or final storage of the optionally singulated extrudate or the final shape of the pharmaceutical dosage forms and particles, respectively, according to the invention is performed under oxygen-free atmosphere which may be achieved, e.g., by means of oxygen-scavengers.

The singulated extrudate may be press-formed into pharmaceutical dosage forms and particles, respectively, in order to impart the final shape to the pharmaceutical dosage forms and particles, respectively.

The application of force in the extruder onto the at least plasticized mixture is adjusted by controlling the rotational speed of the conveying device in the extruder and the geometry thereof and by dimensioning the outlet orifice in such a manner that the pressure necessary for extruding the plasticized mixture is built up in the extruder, preferably immediately prior to extrusion. The extrusion parameters which, for each particular composition, are necessary to give rise to a pharmaceutical dosage form with desired mechanical properties, may be established by simple preliminary testing.

For example but not limiting, extrusion may be performed by means of a twin-screw-extruder type ZSE 18 or ZSE 27 (Leistritz, Nurnberg, Germany) or Thermo Scientific* Pharma 16 HME, screw diameters of 16, 18 or 27 mm. Screws having eccentric or blunt ends may be used. A heatable die with a round bore or with a multitude of bores each having a diameter of 0.2, 0.3, 0.4, 0.5, 0.6, 0.7, 0.8, 0.9, 1.0, 2.0, 3.0, 4.0, 5.0 or 6.0 mm may be used. The extrusion parameters may be adjusted e.g. to the following values: rotational speed of the screws: 120 Upm; delivery rate 0.5 kg/h for Pharma 16, 2 kg/h for a ZSE 18 or 8 kg/h for a ZSE 27; product temperature: in front of die 100 to 125° C. and behind die 125 to 135° C.; and jacket temperature: 110° C.

Preferably, extrusion is performed by means of twin-screw-extruders or planetary-gear-extruders, twin-screw extruders (co-rotating or contra-rotating) being particularly preferred.

The pharmaceutical dosage forms and particles, respectively, according to the invention are preferably produced by thermoforming with the assistance of an extruder without any observable consequent discoloration of the extrudates.

The process for the preparation of the pharmaceutical dosage forms and particles, respectively, according to the invention is preferably performed continuously. Preferably, the process involves the extrusion of a homogeneous mixture of all components. It is particularly advantageous if the thus obtained intermediate, e.g. the strand obtained by extrusion, exhibits uniform properties. Particularly desirable are uniform density, uniform distribution of the active compound, uniform mechanical properties, uniform porosity, uniform appearance of the surface, etc. Only under these circumstances the uniformity of the pharmacological properties, such as the stability of the release profile, may be ensured and the amount of rejects can be kept low.

Preferably, the pharmaceutical dosage form is multiparticulate and the particles according to the invention can be regarded as "extruded pellets". The term "extruded pellets" has structural implications which are understood by persons skilled in the art. A person skilled in the art knows that pelletized pharmaceutical dosage forms can be prepared by a number of techniques, including:
drug layering on nonpareil sugar or microcrystalline cellulose beads,
spray drying,
spray congealing,
rotogranulation,
hot-melt extrusion,
spheronization of low melting materials, or
extrusion-spheronization of a wet mass.

Accordingly, "extruded pellets" can be obtained either by hot-melt extrusion or by extrusion-spheronization.

"Extruded pellets" can be distinguished from other types of pellets because they are structurally different. For example, drug layering on nonpareils yields multilayered pellets having a core, whereas extrusion typically yields a monolithic mass comprising a homogeneous mixture of all ingredients. Similarly, spray drying and spray congealing typically yield spheres, whereas extrusion typically yields cylindrical extrudates which can be subsequently spheronized.

The structural differences between "extruded pellets" and "agglomerated pellets" are significant because they may affect the release of active substances from the pellets and consequently result in different pharmacological profiles. Therefore, a person skilled in the pharmaceutical formulation art would not consider "extruded pellets" to be equivalent to "agglomerated pellets".

The pharmaceutical dosage forms according to the invention may be prepared by any conventional method. Preferably, however, the pharmaceutical dosage forms are prepared by compression. Thus, particles as hereinbefore defined are preferably mixed, e.g. blended and/or granulated (e.g. wet granulated), with outer matrix material and the resulting mix (e.g. blend or granulate) is then compressed, preferably in molds, to form pharmaceutical dosage forms. It is also envisaged that the particles herein described may be incorporated into a matrix using other processes, such as by melt granulation (e.g. using fatty alcohols and/or water-soluble waxes and/or water-insoluble waxes) or high shear granulation, followed by compression.

When the pharmaceutical dosage forms according to the invention are manufactured by means of an eccentric press, the compression force is preferably within the range of from 5 to 15 kN. When the pharmaceutical dosage forms according to the invention are manufactured by means of a rotating press, the compression force is preferably within the range of from 5 to 40 kN, in certain embodiments >25 kN, in other embodiments about 13 kN.

Another aspect of the invention relates to a tamper-resistant, oral pharmaceutical dosage form which is obtainable by any of the processes described above.

The pharmaceutical dosage form according to the invention is characterized by excellent storage stability. Preferably, after storage for 4 weeks at 40° C. and 75% rel. humidity, the content of pharmacologically active ingredient amounts to at least 98.0%, more preferably at least 98.5%, still more preferably at least 99.0%, yet more preferably at least 99.2%, most preferably at least 99.4% and in particular at least 99.6%, of its original content before storage. Suitable methods for measuring the content of the pharmacologically active ingredient in the pharmaceutical dosage form are known to the skilled artisan. In this regard it is referred to the Eur. Ph. or the USP, especially to reversed phase HPLC analysis. Preferably, the pharmaceutical dosage form is stored in closed, preferably sealed containers.

The pharmaceutical dosage forms according to the invention may be used in medicine, e.g. as an analgesic. The pharmaceutical dosage forms are therefore particularly suitable for the treatment or management of pain. In such pharmaceutical dosage forms, the pharmacologically active ingredient preferably is analgesically effective.

A further aspect of the invention relates to the pharmaceutical dosage form as described above for use in the treatment of pain.

A further aspect of the invention relates to the use of the pharmacologically active ingredient for the manufacture of a pharmaceutical dosage form as described above for treating pain.

A further aspect of the invention relates to a method of treating pain comprising the administration of the pharmaceutical dosage form as described above to a subject in need thereof.

A further aspect according to the invention relates to the use of a pharmaceutical dosage form as described above for providing prolonged release of the pharmacologically active ingredient contained therein.

A further aspect according to the invention relates to the use of a pharmaceutical dosage form as described above for avoiding or hindering the abuse of the pharmacologically active ingredient contained therein.

A further aspect according to the invention relates to the use of a pharmaceutical dosage form as described above for avoiding or hindering the unintentional overdose of the pharmacologically active ingredient contained therein.

In this regard, the invention also relates to the use of a pharmaceutical dosage form as described above for the prophylaxis and/or the treatment of a disorder, thereby preventing an overdose of the pharmacologically active ingredient, particularly due to comminution of the pharmaceutical dosage form by mechanical action.

In a particularly preferred embodiment,
- the pharmaceutical dosage form according to the invention is monolithic or multiparticulate or a MUPS formulation; and/or
- the pharmaceutical dosage form according to the invention is hot-melt extruded; and/or
- the pharmaceutical dosage form according to the invention provides prolonged release of the pharmacologically active ingredient having psychotropic action; and/or
- the pharmacologically active ingredient having psychotropic action is an opioid or a physiologically acceptable salt thereof; and/or
- the content of the pharmacologically active ingredient is within the range of from 1 to 35 wt.-%, based on the total weight of the pharmaceutical dosage form; and/or
- the EVA polymer comprises repetition units derived from ethylene and vinyl acetate and/or vinyl alcohol; and/or
- the EVA polymer contains 60±30 wt.-%, more preferably 60±5 wt.-% of ethylene repetition units, relative to the total weight of the EVA polymer; and/or
- the EVA polymer has a melt flow rate at 190° C. and 2.16 kg of 52±2 g/10 min measured according to ASTM D1238; and/or
- the content of the EVA polymer is within the range of from 45 to 70 wt.-%, relative to the total weight of the pharmaceutical dosage form or, when the pharmaceutical dosage form is multiparticulate, relative to the total weight of the particles that contain the pharmacologically active ingredient; and/or
- the pharmacologically active ingredient is embedded in a prolonged release matrix containing the EVA polymer as prolonged release matrix material and additional prolonged release matrix material; wherein
  - the content of the additional prolonged release matrix material is in the range of 5 to 30 wt.-%, relative to the total weight of the prolonged release matrix; and/or
  - the additional prolonged release matrix material is a polyalkylene oxide, preferably a polyethylene oxide having a weight average molecular weight of at least 5,000,000 g/mol; or
  - the additional prolonged release matrix material is a mixture of polyvinyl pyrrolidone and polyvinyl acetate, wherein said mixture has a K-value in the range of from 60 to 65, measured in a 1% solution in tetrahydrofurane according to the method described in the USP and Ph. Eur. monographs "Povidone", wherein the weight ratio between polyvinyl acetate and polyvinyl pyrrolidone is in the range of 4.5:1 to 3.5:1; or
  - the additional prolonged release matrix material is an anionic acrylic polymer, preferably a polyacrylic acid polymer which is crosslinked with ally pentaerythritol having a viscosity of 4,000 to 11,000 mPa·s, measured with a Brookfield RVT, 20 rpm, spindle no. 5 at 25° C. and 0.5 wt.-% neutralized to pH 7.3-7.8.

EXAMPLES

For manufacturing the pellets, mixtures of the pharmacologically active ingredient, EVA and excipients were produced by weighing the ingredients (batch size 500.0 g), sieving (Mesh size 1.0 mm), blending in a Bohle LM 40 MC 20, followed by extrusion using a Leistritz ZSE 18 melt extruder type MICRO 18 GL-40D Pharma (melt temperature 124° C., screw rotation speed 100 rpm, die diameter 1.0 mm, melt pressure 1-4 bar). The extruded strands were cooled in ambient air and were manually cut yielding pellets.

General procedure 1 (GP1) for manufacturing the cut rods: mixtures of the pharmacologically active ingredient, EVA and excipients were produced by weighing the ingredients (batch size 500.0 g), sieving (Mesh size 1.0 mm), blending in a Bohle LM 40 MC 20, followed by extrusion using a Leistritz Micro 18 HME (melt temperature ca. 124° C., screw rotation speed 50-100 rpm, die diameter 5.0 mm, melt pressure 16-47 bar). The extruded strands were cooled in ambient air and were manually cut with a hot knife into cut rods.

General procedure 2 (GP2) for manufacturing the cut rods: mixtures of the pharmacologically active ingredient, EVA and excipients were produced by weighing the ingredients (batch size 500.0 g), sieving (Mesh size 1.0 mm), blending in a Bohle LM 40 MC 20, followed by extrusion using a Leistritz Micro 27 lab extruder (melt temperature ca. 124° C., screw rotation speed 50-100 rpm, die diameter 5.0 mm, melt pressure 16-47 bar). The extruded strands were cooled in ambient air and were manually cut with a hot knife into cut rods.

The pellets and cut rods, respectively, were subjected to different tests in order to assess the tamper-resistance with respect to the pharmacologically active ingredient contained in the pellets and cut rods, respectively.

Materials
Elvax® 40W ethylene-vinyl acetate copolymer (40 wt.-% vinyl acetate comonomer)
Elvax® 40L-03 ethylene-vinyl acetate copolymer (40 wt.-% vinyl acetate comonomer)
Elvax® 220W ethylene-vinyl acetate copolymer (28 wt.-% vinyl acetate comonomer)
Elvax® 265 ethylene-vinyl acetate copolymer (28 wt.-% vinyl acetate comonomer)
Elvax® 660 ethylene-vinyl acetate copolymer (12 wt.-% vinyl acetate comonomer)

PEO 7 Mio. polyethylene oxide (7 mio)
Kollidon SR mixture of polyvinyl acetate and polyvinyl pyrrolidone
Carbopol 71 G polymer of acrylic acid crosslinked with allyl ethers of pentaerythritol
Xanthan a polysaccharide comprising pentasaccharide repeat units comprising glucose, mannose and glucuronic acid
HPMC hydroxypropylmethylcellulose
Kollicoat IR polyvinyl alcohol-polyethylene glycol graft copolymer

Example 1

Pellets were prepared having the following composition:

| substance | per tablet [mg] | amount [%] |
|---|---|---|
| Tramadol HCl | 122.33 | 34.95 |
| Elvax ® 40W | 175.00 | 50.00 |
| PEO 7 Mio. | 52.67 | 15.05 |
| total | 350.00 | 100.00 |

Pellets were ground with a commercial coffee mill, type Bosch MKM6000, 180W, Typ KM13 for 2 min. Afterwards, the ground pellets were subjected to a sieving analysis. The result of which is summarized in FIG. 1.

Figure 3:
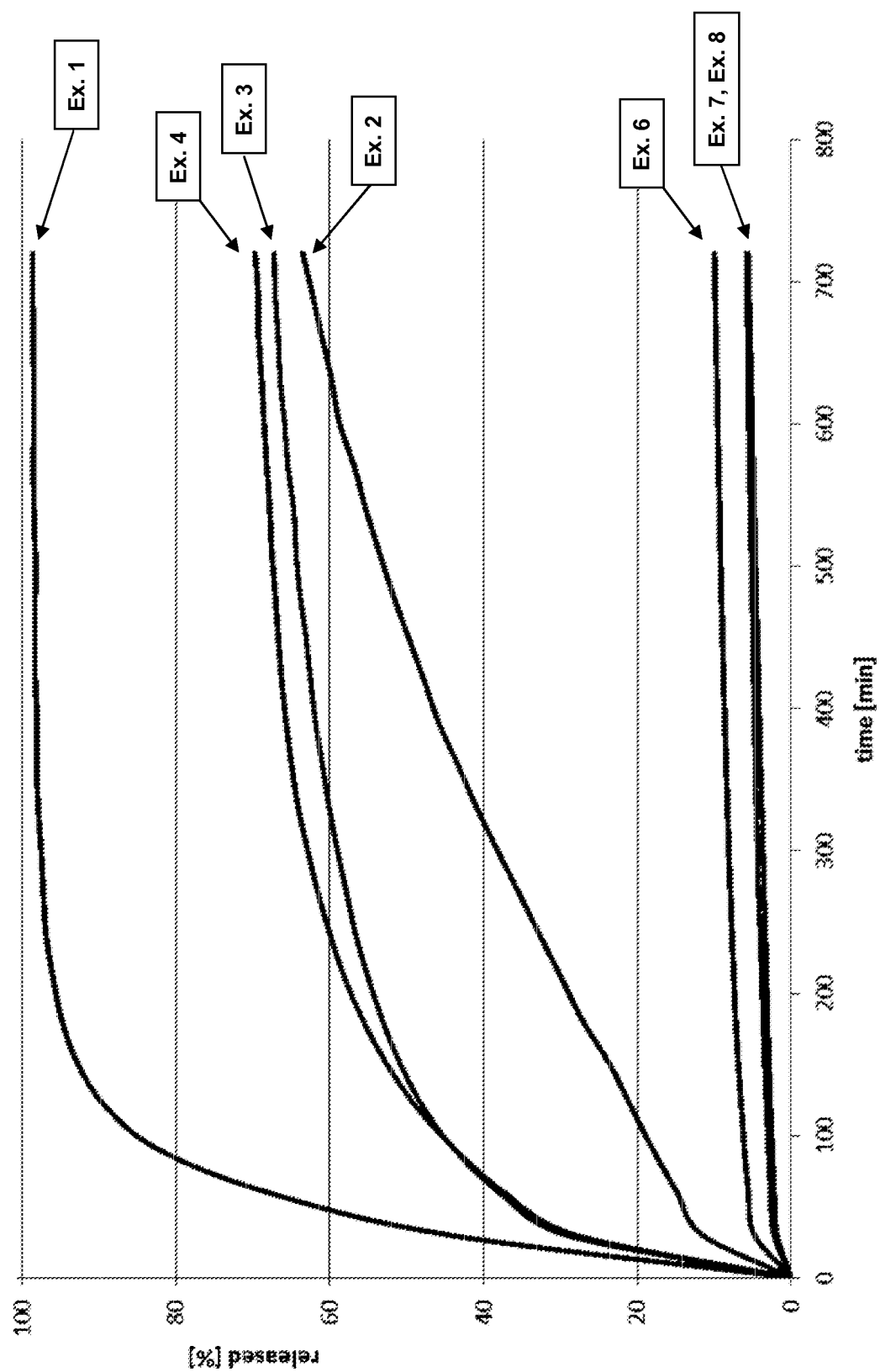
FIG. 3 is a chart showing the release profiles of the indicated exemplified embodiments.

The release profile of tramadol HCl from the pellets was determined under in vitro conditions using the basket method according to Ph. Eur. at 75 rpm in 900 mL of buffered SIF sp (pH 6.8) (without sinker, n=3). The results are summarized in FIG. 3.

Example 2

Pellets were prepared having the following composition:

| substance | per tablet [mg] | amount [%] |
|---|---|---|
| Tramadol HCl | 116.48 | 33.28 |
| Elvax ® 40W | 233.52 | 66.72 |
| total | 350.00 | 100.00 |

Figure 2:
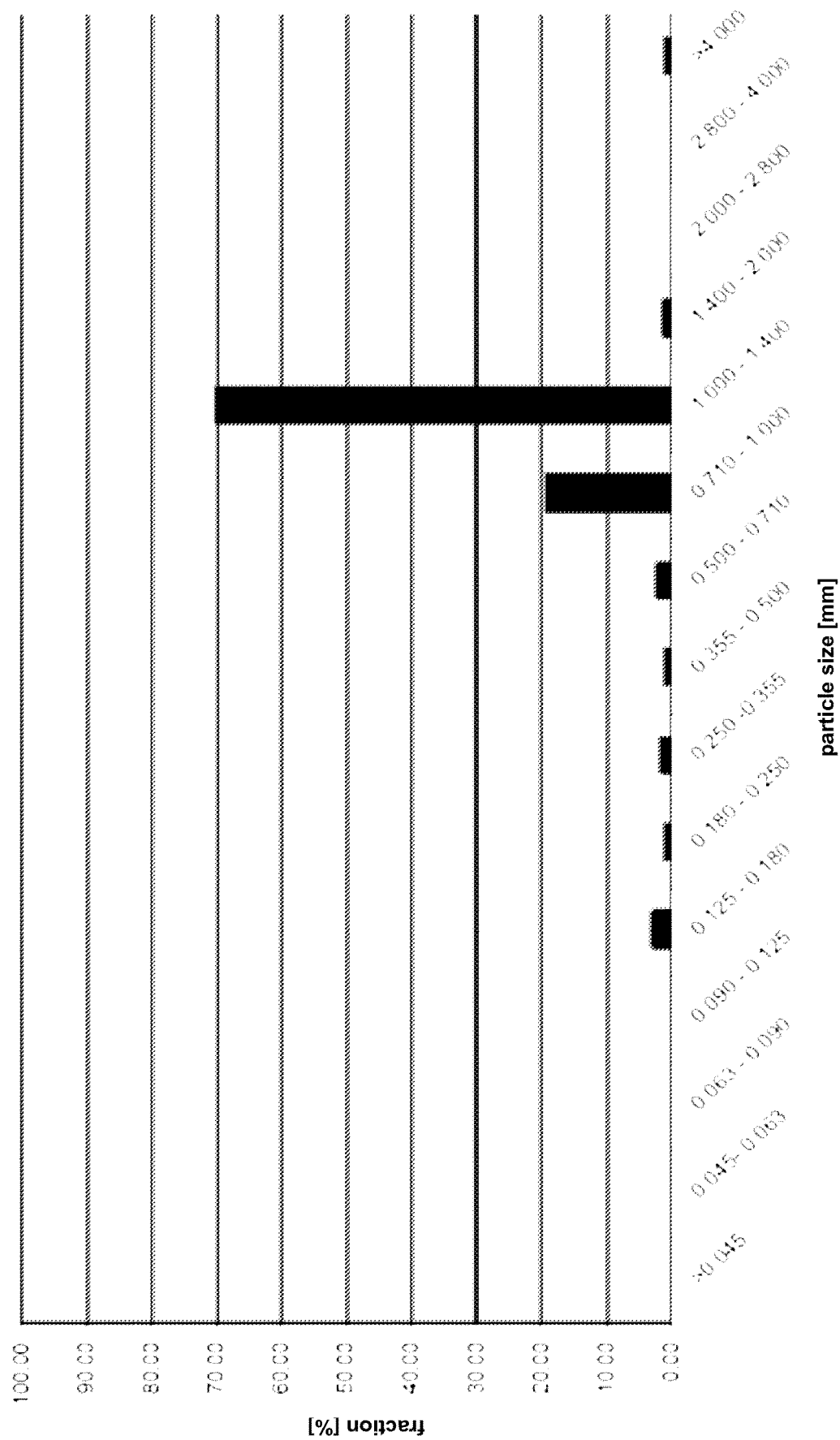
FIG. 2 is a graph depicting the results of the sieving analysis referred to in Example 2.

Pellets were ground with a commercial coffee mill, type Bosch MKM6000, 180W, Typ KM13 for 2 min. Afterwards, the ground pellets were subjected to a sieving analysis. The result of which is summarized in FIG. 2.

To simulate an addict's attempt at preparing an i.v. injection, pellets were ground with a commercial coffee mill, type Bosch MKM6000, 180W, Typ KM13 for 2 min followed by extraction in boiled water for 5 min. The results are summarized in the below table.

TABLE 1 simulated preparation of i.v. injection.

| | | intact | ground |
|---|---|---|---|
| content [%] | 1 | 13.56 | 39.62 |
| (n = 3) | 2 | 13.34 | 29.49 |
| | 3 | 12.48 | 25.98 |
| mean [%] | | 13.13 | 31.70 |

Figure 4:
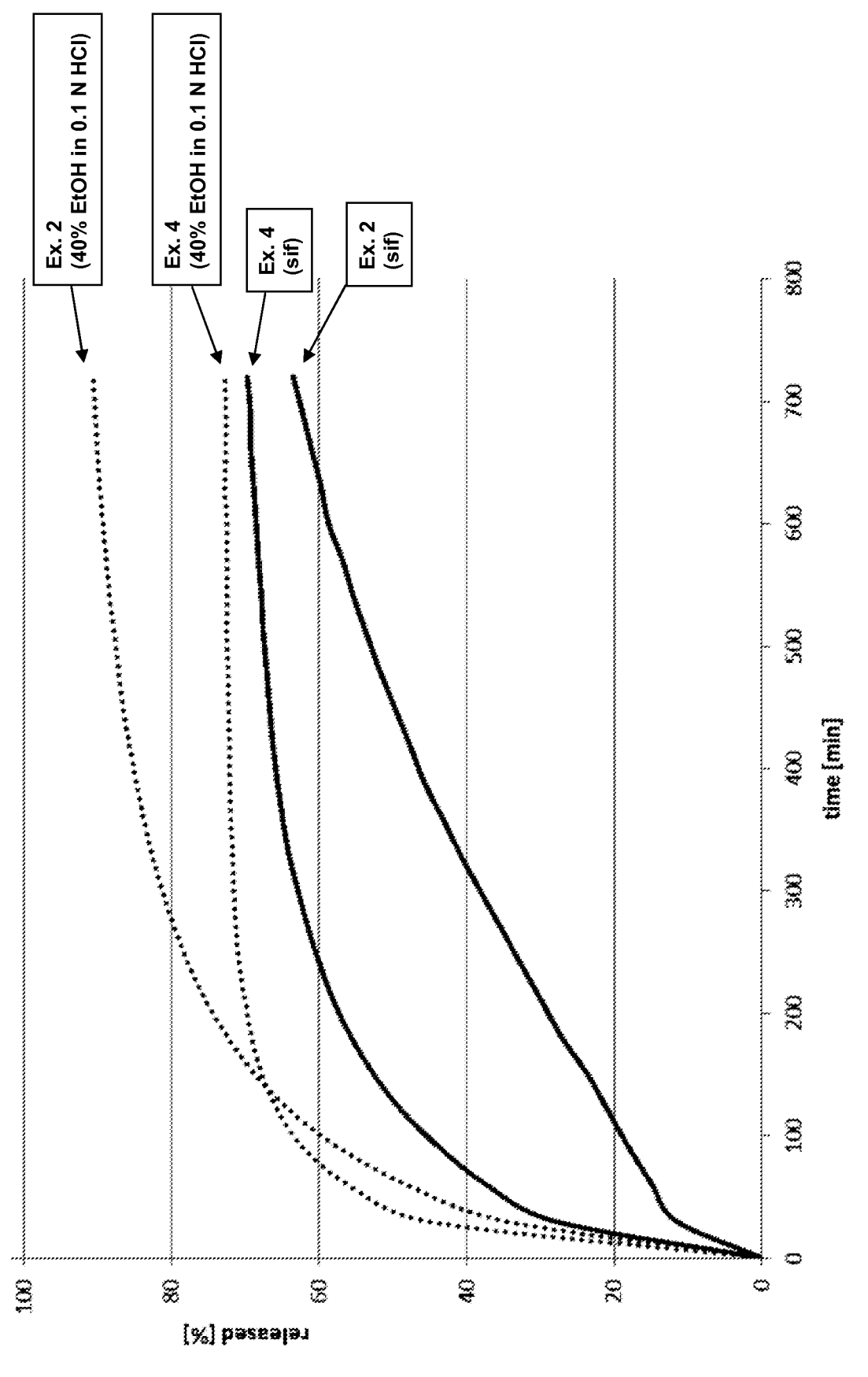
FIG. 4 is a chart showing the release profiles of the indicated exemplified embodiments.

The release profiles of tramadol HCl from the pellets were determined under in vitro conditions using the basket method according to Ph. Eur. at 75 rpm in 900 mL of buffered SIF sp (pH 6.8) and in 900 mL of 40% ethanol in 0.1 N HCl, respectively, (without sinker, n=3). The results are summarized in FIGS. 3 and 4.

Example 3

Pellets were prepared having the following composition:

| substance | per tablet [mg] | amount [%] |
|---|---|---|
| Tramadol HCl | 116.48 | 33.28 |
| Elvax ® 40W | 198.52 | 56.72 |
| Kollidon SR | 35.00 | 10.00 |
| total | 350.00 | 100.00 |

To simulate an addict's attempt at preparing an i.v. injection, pellets were ground with a commercial coffee mill, type Bosch MKM6000, 180W, Typ KM13 for 2 min followed by extraction in boiled water for 5 min. The results are summarized in the below table.

TABLE 2 simulated preparation of i.v. injection.

| | | intact | ground |
|---|---|---|---|
| content [%] | 1 | 16.41 | 23.98 |
| (n = 3) | 2 | 19.58 | 30.52 |
| | 3 | 15.99 | 26.25 |
| mean [%] | | 17.33 | 26.92 |

The release profile of tramadol HCl from the pellets was determined under in vitro conditions using the basket method according to Ph. Eur. at 75 rpm in 900 mL of buffered SIF sp (pH 6.8) (without sinker, n=3). The results are summarized in FIG. 3.

Example 3A

Cut rods were prepared according to GP1 having the same composition as the pellets of Example 3.

Figure 5:
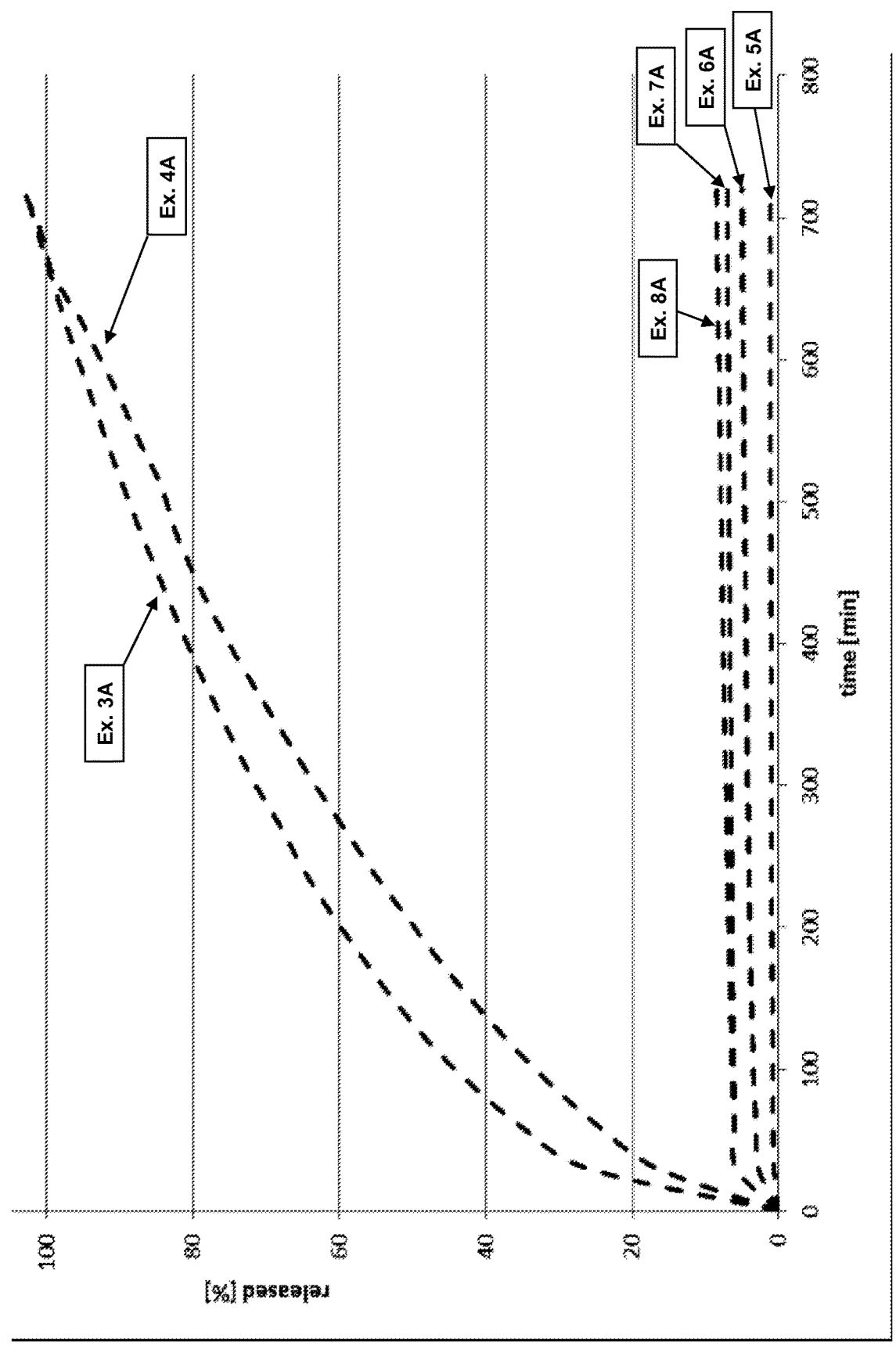
FIG. 5 is a chart showing the release profiles of the indicated exemplified embodiments.

The release profile of tramadol HCl from the cut rods was determined under in vitro conditions using the paddle method according to Ph. Eur. at 50 rpm in 900 mL of buffered SIF sp (pH 6.8) (without sinker, n=3). The results are summarized in FIG. 5.

Example 4

Pellets were prepared having the following composition:

| substance | per tablet [mg] | amount [%] |
|---|---|---|
| Tramadol HCl | 116.48 | 33.28 |
| Elvax ® 40W | 207.27 | 59.22 |
| Carbopol 71G | 26.25 | 7.50 |
| total | 350.00 | 100.00 |

To simulate an addict's attempt at preparing an i.v. injection, pellets were ground with a commercial coffee mill, type Bosch MKM6000, 180W, Typ KM13 for 2 min followed by extraction in boiled water for 5 min. The results are summarized in the below table.

TABLE 3

| simulated preparation of i.v. injection. | | | |
|---|---|---|---|
| | | intact | ground |
| content [%] | 1 | 11.20 | 42.90 |
| (n = 3) | 2 | 21.31 | 44.86 |
| | 3 | 32.67 | 33.42 |
| mean [%] | | 21.73 | 40.39 |

The release profiles of tramadol HCl from the pellets were determined under in vitro conditions using the basket method according to Ph. Eur. at 75 rpm in 900 mL of buffered SIF sp (pH 6.8) and in 900 mL of 40% ethanol in 0.1 N HCl, respectively, (without sinker, n=3). The results are summarized in FIGS. 3 and 4.

Example 4A

Cut rods were prepared according to GP1 having the same composition as the pellets of Example 4.

To simulate an addict's attempt at preparing an i.v. injection, cut rods were ground with a commercial coffee mill, type Bosch MKM6000, 180W, Typ KM13 for 2 min followed by extraction in boiled water for 5 min. The results are summarized in the below table.

TABLE 4

| simulated preparation of i.v. injection. | | | |
|---|---|---|---|
| | | intact | ground |
| content [%] | 1 | 29.70 | 84.71 |
| (n = 3) | 2 | 30.99 | 79.44 |
| | 3 | 38.45 | 53.18 |
| mean [%] | | 33.05 | 72.44 |

The cut rods displayed a breaking strength (resistance to crushing) of 1000 N (average value, n=10) determined with a Zwick Z 2.5 materials tester, $F_{max}$=2.5 kN, maximum draw: 1150 mm.

The release profile of tramadol HCl from the cut rods was determined under in vitro conditions using the paddle method according to Ph. Eur. at 50 rpm in 900 mL of buffered SIF sp (pH 6.8) (without sinker, n=3). The results are summarized in FIG. 5.

Example 5

Pellets were prepared having the following composition:

| substance | per tablet [mg] | amount [%] |
|---|---|---|
| Tramadol HCl | 116.48 | 33.28 |
| Elvax ® 220W | 233.52 | 66.72 |
| total | 350.00 | 100.00 |

Example 5A

Cut rods were according to GP1 prepared having the same composition as the pellets of Example 5.

The release profile of tramadol HCl from the cut rods was determined under in vitro conditions using the paddle method according to Ph. Eur. at 50 rpm in 900 mL of buffered SIF sp (pH 6.8) (without sinker, n=3). The results are summarized in FIG. 5.

Example 6

Pellets were prepared having the following composition:

| substance | per tablet [mg] | amount [%] |
|---|---|---|
| Tramadol HCl | 116.48 | 33.28 |
| Elvax ® 265 | 233.52 | 66.72 |
| total | 350.00 | 100.00 |

To simulate an addict's attempt at preparing an i.v. injection, pellets were ground with a commercial coffee mill, type Bosch MKM6000, 180W, Typ KM13 for 2 min followed by extraction in boiled water for 5 min. The results are summarized in the below table.

TABLE 5

| simulated preparation of i.v. injection. | | | |
|---|---|---|---|
| | | intact | ground |
| content [%] | 1 | 3.06 | 7.45 |
| (n = 3) | 2 | 4.51 | 8.02 |
| | 3 | 4.47 | 8.38 |
| mean [%] | | 4.01 | 7.95 |

The release profile of tramadol HCl from the pellets was determined under in vitro conditions using the basket method according to Ph. Eur. at 75 rpm in 900 mL of buffered SIF sp (pH 6.8) (without sinker, n=3). The results are summarized in FIG. 3.

Example 6A

Cut rods were prepared according to GP1 having the same composition as the pellets of Example 6.

To simulate an addict's attempt at preparing an i.v. injection, cut rods were ground with a commercial coffee mill, type Bosch MKM6000, 180W, Typ KM13 for 2 min followed by extraction in boiled water for 5 min. The results are summarized in the below table.

TABLE 6

| simulated preparation of i.v. injection. | | | |
|---|---|---|---|
| | | intact | ground |
| content [%] | 1 | 2.38 | 38.58 |
| (n = 3) | 2 | 2.51 | 17.47 |
| | 3 | 1.51 | 38.99 |
| mean [%] | | 2.13 | 31.68 |

The cut rods displayed a breaking strength (resistance to crushing) of 1000 N (average value, n=10) determined with a Zwick Z 2.5 materials tester, $F_{max}$=2.5 kN, maximum draw: 1150 mm.

The release profile of tramadol HCl from the cut rods was determined under in vitro conditions using the paddle method according to Ph. Eur. at 50 rpm in 900 mL of buffered SIF sp (pH 6.8) (without sinker, n=3). The results are summarized in FIG. 5.

Example 7

Pellets were prepared having the following composition:

| substance | per tablet [mg] | amount [%] |
|---|---|---|
| Tramadol HCl | 116.48 | 33.28 |
| Elvax ® 40L-03 | 233.52 | 66.72 |
| total | 350.00 | 100.00 |

The release profile of tramadol HCl from the pellets was determined under in vitro conditions using the basket method according to Ph. Eur. at 75 rpm in 900 mL of buffered SIF sp (pH 6.8) (without sinker, n=3). The results are summarized in FIG. 3.

Example 7A

Cut rods were prepared according to GP1 having the same composition as the pellets of Example 7.

The release profile of tramadol HCl from the cut rods was determined under in vitro conditions using the paddle method according to Ph. Eur. at 50 rpm in 900 mL of buffered SIF sp (pH 6.8) (without sinker, n=3). The results are summarized in FIG. 5.

Example 8

Pellets were prepared having the following composition:

| substance | per tablet [mg] | amount [%] |
|---|---|---|
| Tramadol HCl | 116.48 | 33.28 |
| Elvax ® 660 | 233.52 | 66.72 |
| total | 350.00 | 100.00 |

The release profile of tramadol HCl from the pellets was determined under in vitro conditions using the basket method according to Ph. Eur. at 75 rpm in 900 mL of buffered SIF sp (pH 6.8) (without sinker, n=3). The results are summarized in FIG. 3.

Example 8A

Cut rods were prepared according to GP1 having the same composition as the pellets of Example 8.

The release profile of tramadol HCl from the cut rods was determined under in vitro conditions using the paddle method according to Ph. Eur. at 50 rpm in 900 mL of buffered SIF sp (pH 6.8) (without sinker, n=3). The results are summarized in FIG. 5.

In examples 7 and 7A, and in examples 8 and 8A, respectively, the pharmacologically active substance was in both cases tramadol HCl, the releasing polymer was EVA. The composition of both the cut rods (die diameter 1.0 mm) and the pellets (die diameter 5.0 mm) was identical. Considering FIGS. 3 and 5, it becomes evident that the particle size had no influence on the release behavior of EVA, as in both cases a prolonged-release (PR) of tramadol HCl could be observed.

Example 9

Cut rods were prepared according to GP2 having the following composition:

| Substance | per tablet [mg] | amount [%] |
|---|---|---|
| Tramadol HCl | 50.00 | 14.30 |
| Elvax EVA 40W | 212.50 | 60.7 |
| Xanthan | 35.00 | 10.00 |
| HPMC | 17.50 | 5.00 |
| Carbopol | 35.00 | 10.00 |
| total | 350.00 | 100.00 |

Figure 6:
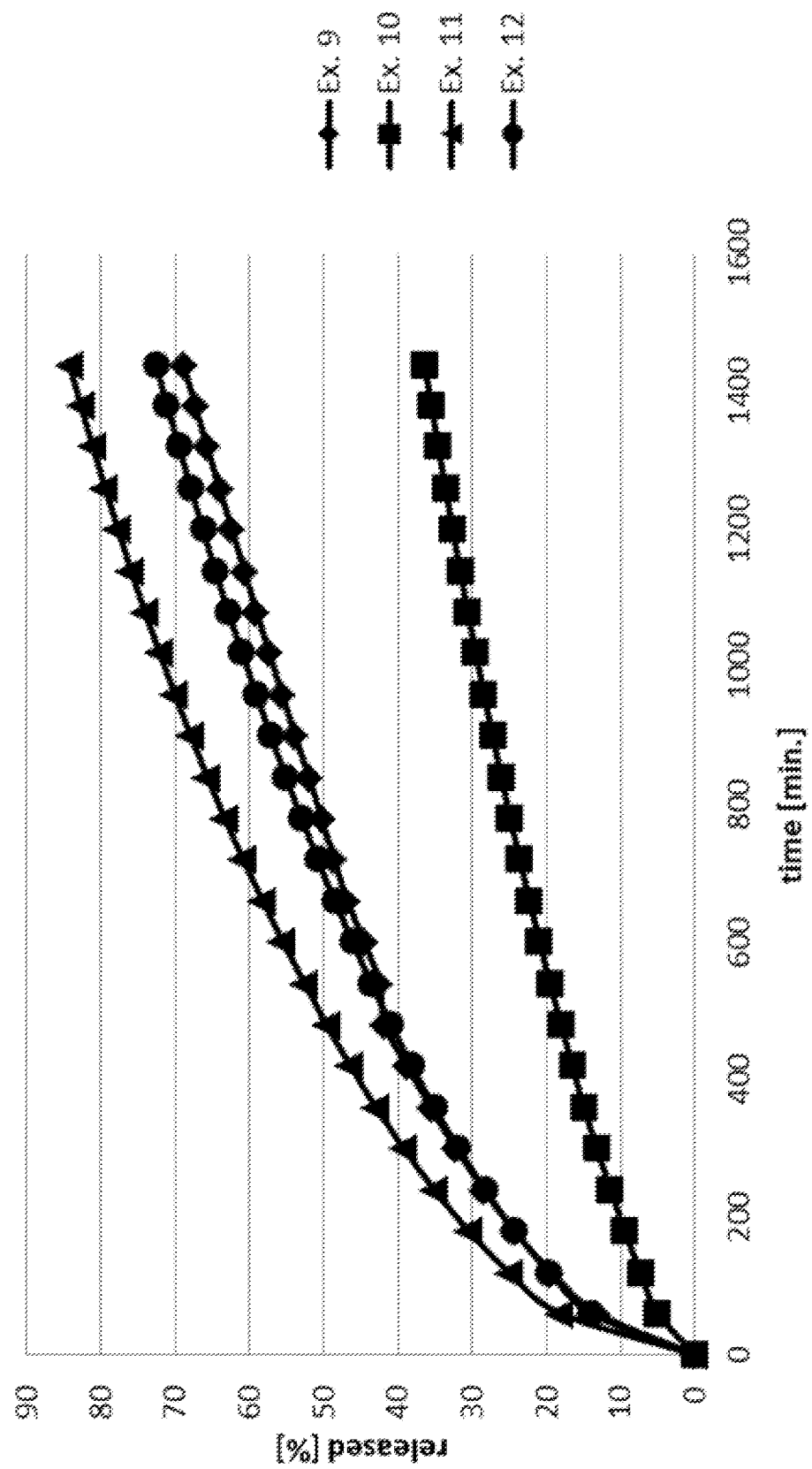
FIG. 6 is a chart showing the release profiles of the indicated exemplified embodiments.

The release profile of tramadol HCl from cut rods was determined under in vitro conditions using the paddle method according to Ph. Eur. at 75 rpm in 600 mL of buffered SIF sp (pH 6.8) with sinker type 1, n=3. The results are shown in FIG. 6.

Figure 7:
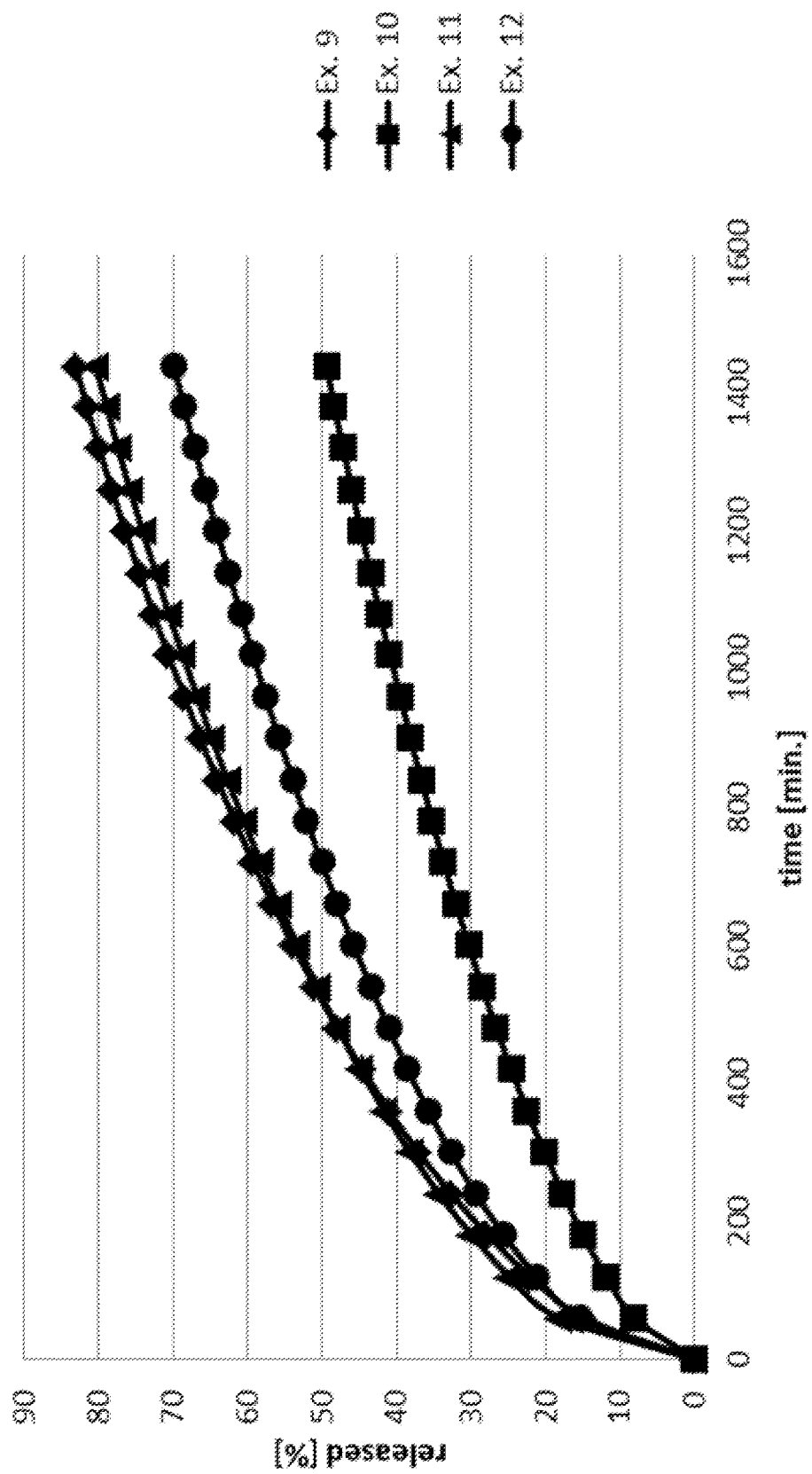
FIG. 7 is a chart showing the release profiles of the indicated exemplified embodiments.

The release profile of tramadol HCl from cut rods was also determined in aqueous ethanol using the paddle method according to Ph. Eur. At 75 rpm in 600 mL of 0.1 N HCl 40% EtOH with sinker type 1, n=3. The results are shown in FIG. 7.

To simulate an addict's attempt at preparing an i.v. injection, an extraction was carried out according to example 2. The results are summarized in the below table.

TABLE 7 simulated preparation of i.v. injection.

| | | intact | manipulated |
|---|---|---|---|
| content [%] (n = 3) | 1 | 3.50 | — |
| | 2 | 1.49 | — |
| | 3 | 3.31 | — |
| mean [%] | | 2.77 | — |

Example 10

Cut rods were prepared according to GP2 having the following composition:

| Substance | per tablet [mg] | amount [%] |
|---|---|---|
| Tramadol HCl | 50.00 | 14.30 |
| Elvax EVA 40W | 107.50 | 30.70 |
| Elvax 265A | 105.00 | 30.00 |
| Xanthan | 35.00 | 10.00 |
| Kollicoat SR | 52.50 | 15.00 |
| total | 350.00 | 100.00 |

The release profile of tramadol HCl from the cut rods was determined under in vitro conditions using the paddle method according to Ph. Eur. at 75 rpm in 600 mL of buffered SIF sp (pH 6.8) with sinker type 1, n=3. The results are summarized in FIG. 6.

The release profile of tramadol HCl from cut rods was also determined in aqueous ethanol using the paddle method according to Ph. Eur. At 75 rpm in 600 mL of 0.1 N HCl 40% EtOH with sinker type 1, n=3. The results are summarized in FIG. 7.

To simulate an addict's attempt at preparing an i.v. injection, an extraction was carried out according to example 2. The results are summarized in the below table.

TABLE 8

| simulated preparation of i.v. injection. | | | |
|---|---|---|---|
| | | intact | manipulated |
| content [%] (n = 3) | 1 | 2.65 | — |
| | 2 | 1.24 | — |
| | 3 | 1.86 | — |
| mean [%] | | 1.92 | — |

Example 11

Cut rods were prepared according to GP2 having the following composition:

| Substance | per tablet [mg] | amount [%] |
|---|---|---|
| Tramadol HCl | 50.00 | 14.30 |
| Elvax 265A | 195.00 | 55.70 |
| Xanthan | 35.00 | 10.00 |
| Kollicoat IR | 70.00 | 20.00 |
| total | 350.00 | 100.00 |

The release profile of tramadol HCl from cut rods was determined under in vitro conditions using the paddle method according to Ph. Eur. at 75 rpm in 600 mL of buffered SIF sp (pH 6.8) with sinker type 1, n=3. The results are summarized in FIG. 6.

The release profile of tramadol HCl from cut rods was also determined in aqueous ethanol using the paddle method according to Ph. Eur. At 75 rpm in 600 mL of 0.1 N HCl 40% EtOH with sinker type 1, n=3. The results are summarized in FIG. 7.

To simulate an addict's attempt at preparing an i.v. injection, an extraction was carried out according to example 2. The results are summarized in the below table.

TABLE 9

| simulated preparation of i.v. injection. | | | |
|---|---|---|---|
| | | intact | manipulated |
| content [%] (n = 3) | 1 | 15.15 | — |
| | 2 | 13.90 | — |
| | 3 | 12.59 | — |
| mean [%] | | 13.26 | — |

Example 12

Cut rods were prepared according to GP2 having the following composition:

| Substance | per tablet [mg] | amount [%] |
|---|---|---|
| Tramadol HCl | 50.00 | 14.30 |
| Elvax 265A | 125.00 | 35.70 |
| Elvax 40W | 70.00 | 20.00 |
| Kollicoat IR | 70.00 | 20.00 |
| Xanthan | 35.00 | 10.00 |
| total | 350.00 | 100.00 |

The release profile of tramadol HCl from cut rods was determined under in vitro conditions using the paddle method according to Ph. Eur. at 75 rpm in 600 mL of buffered SIF sp (pH 6.8) with sinker type 1, n=3. The results are summarized in FIG. 6.

The release profile of tramadol HCl from cut rods was also determined in aqueous ethanol using the paddle method according to Ph. Eur. At 75 rpm in 600 mL of 0.1 N HCl 40% EtOH with sinker type 1, n=3. The results are summarized in FIG. 7.

To simulate an addict's attempt at preparing an i.v. injection, an extraction was carried out according to example 2. The results are summarized in the below table.

TABLE 10

| simulated preparation of i.v. injection. | | | |
|---|---|---|---|
| | | intact | manipulated |
| content [%] (n = 3) | 1 | 15.29 | — |
| | 2 | 15.90 | — |
| | 3 | 8.59 | — |
| mean [%] | | 13.26 | — |

Examples 9-12 demonstrate the resistance of EVA-containing formulations against dose-dumping in aqueous ethanol. Comparing FIGS. 6 and 7, it becomes evident that the dissolution behavior of the corresponding monolithic form (i.e. cut rods with a die diameter of 5 mm) in aqueous ethanol is equal to the dissolution behavior under in vitro conditions. Thus, the controlled release portion of the formulation cannot be defeated by the extraction with ethanol or by the concomitant intake of ethanol.

For all examples 9-12, a manipulation of the cud rods did not allow a winding up of the pharmaceutically active ingredient.

Comparative Example 13

Pellets were prepared having the following composition:

| Substance | per tablet [mg] | amount [%] |
|---|---|---|
| Tapentadol HCl | 116.48 | 33.28 |
| Hypromellose 100000 mPas | 44.0 | 12.57 |
| PEG 6000 | 35.00 | 10.00 |
| alpha Tocopherol | 0.04 | 0.01 |
| PEO 7 Mio | 154.48 | 44.14 |
| total | 350.00 | 100.00 |

The release profiles of tapentadol HCl from pellets was determined under in vitro conditions using the paddle method according to Ph. Eur. at 50 rpm in 900 mL 0.1N HCl (without sinker, n=3). The results are summarized in FIG. 8.

Comparative Example 13A

Cut rods were prepared according to GP1 having the same composition as the pellets of Example 13.

Figure 8:
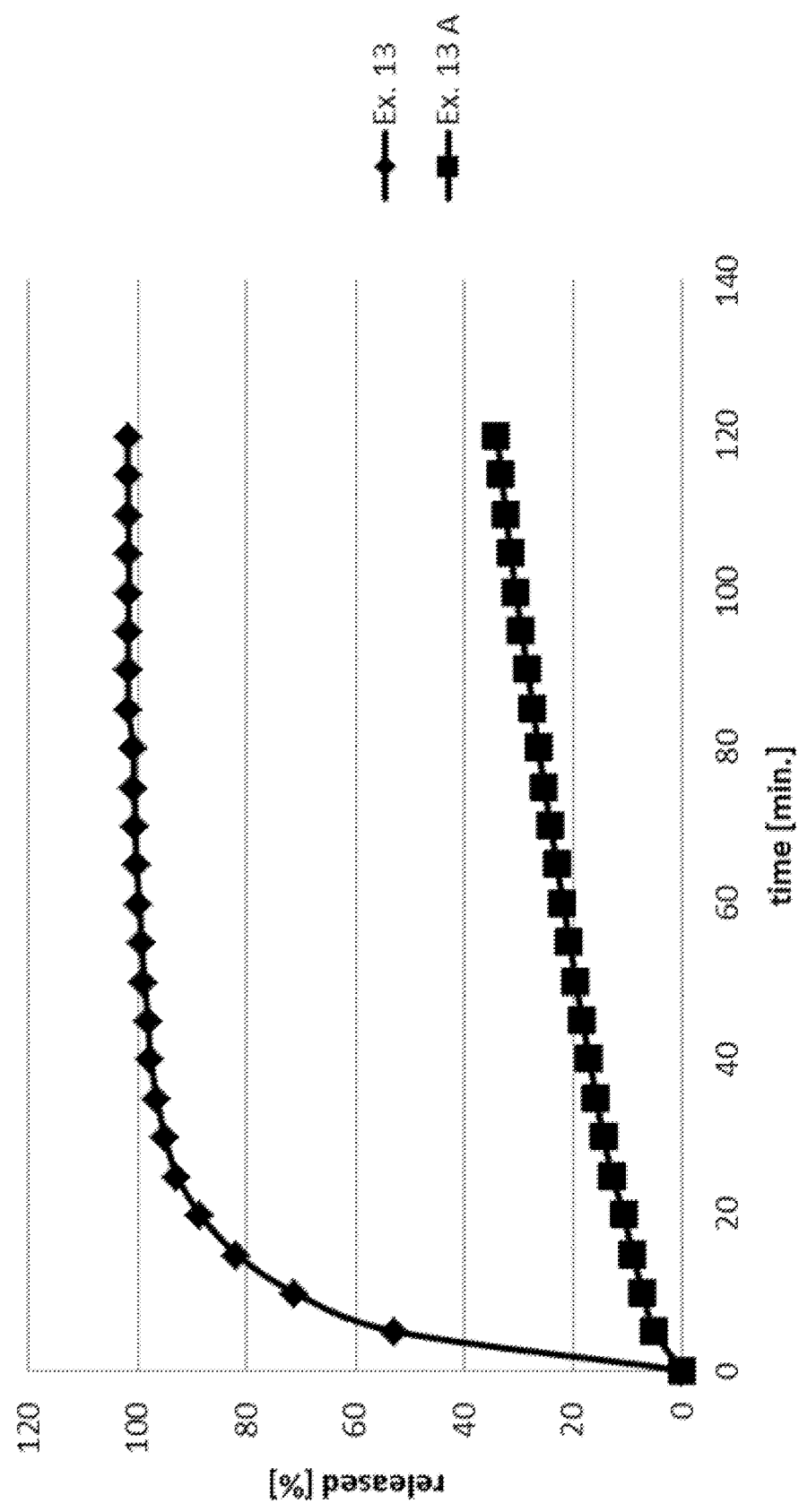
FIG. 8 is a chart showing the release profiles of the indicated exemplified embodiments.

The release profile of tapentadol HCl from cut rods was determined under in vitro conditions using the paddle method according to Ph. Eur. at 50 rpm in 900 mL 0.1N HCl (without sinker, n=3). The results are shown in FIG. 8.

In examples 13 and 13A, the pharmacologically active substance was in both cases tapentadol HCl, the polymer releasing the substance was PEO. The composition of both the cut rods and the pellets was identical. Considering FIG. 8, it becomes evident that for pellets (die diameter 1.0 mm), an immediate-release (IR) of tapentadol HCl could be observed, whereas for cut rods (die diameter 6.0 mm), a prolonged-release (PR) is observed. Thus, for PEO and in contrast to EVA, the particle size has a pronounced influence on the dissolution behavior of the pharmacologically active substance. The smaller the particles, the faster the release.

In the above examples 1-12, the pharmacologically active substance is in all cases tramadol HCl, whereas in examples 13 and 13A, the substance is tapentadol HCl. However, both tapentadol HCl and tramadol HCl show a comparable dissolution behavior and are both water-soluble; the dependency of the dissolution behavior on the particle size is therefore comparable.

The invention claimed is:

1. A tamper-resistant, oral pharmaceutical dosage form comprising a homogeneous mixture of: (A) a pharmacologically active ingredient having psychotropic action and (B) a prolonged release matrix comprising 55 to 80 wt.-% relative to a total weight of the dosage form of an ethylene-vinyl acetate (EVA) polymer, wherein the EVA polymer provides resistance against solvent extraction, resistance against grinding, and resistance against dose-dumping in aqueous ethanol.

2. The pharmaceutical dosage form according to claim 1, wherein the EVA polymer comprises repetition units derived from ethylene and vinyl acetate and/or vinyl alcohol.

3. The pharmaceutical dosage form according to claim 1, wherein the EVA polymer contains at least 50 wt.-% of ethylene repetition units, relative to the total weight of the EVA polymer.

4. The pharmaceutical dosage form according to claim 3, wherein the EVA polymer contains from 50 to 95 wt.-% of ethylene repetition units, relative to the total weight of the EVA polymer.

5. The pharmaceutical dosage form according to claim 1, wherein the EVA polymer has a melt flow rate at 190° C. and 2.16 kg within the range of from 1 to 160 g/10 min measured according to ASTM D1238.

6. The pharmaceutical dosage form according to claim 1, which is monolithic and has a breaking strength of at least 300 N.

7. The pharmaceutical dosage form according to claim 1, which is monolithic and has an extension in any direction of at least 2.0 mm.

8. The pharmaceutical dosage form according to claim 1, wherein the pharmacologically active ingredient is an opioid or a physiologically acceptable salt thereof.

9. The pharmaceutical dosage form according to claim 1, which is hot-melt extruded.

10. A process for the production of the tamper-resistant, oral pharmaceutical dosage form according to claim 1, said process comprising the steps of:
 (i) mixing a pharmacologically active ingredient, 55 to 80 wt.-% relative to a total weight of the dosage form of an ethylene-vinyl acetate (EVA) polymer, and optionally further excipients to form a mixture; and
 (ii) thermoforming the mixture obtained in step (i), wherein said mixture is simultaneously or before or after the application of heat subjected to pressure.

11. A tamper-resistant, oral pharmaceutical dosage form obtained by the process according to claim 10.

12. A method of treating pain in a patient, said method comprising administering to said patient a dosage form according to claim 1 wherein the pharmacologically active ingredient is an opioid or a physiologically acceptable salt thereof.

13. The pharmaceutical dosage form according to claim 1, which is multiparticulate, wherein at least a fraction of individual particles have a breaking strength of at least 300 N.

14. The pharmaceutical dosage form according to claim 1, which is multiparticulate, wherein individual drug-containing particles have an extension in any direction of at least 2.0 mm.

* * * * *